US012616581B2

(12) United States Patent
Davis et al.

(10) Patent No.: US 12,616,581 B2
(45) Date of Patent: May 5, 2026

(54) METHODS FOR RESTORING BILATERAL SPINAL ALIGNMENT AND/OR RANGE OF MOTION

(71) Applicant: 3Spine, Inc., Chattanooga, TN (US)

(72) Inventors: Christian Davis, Cambridge, MA (US); Marc M. Peterman, Duxbury, MA (US); Steven C. Humphreys, Soldotna, AK (US); Scott Hodges, Chattanooga, TN (US); Ron Yarbrough, Round Rock, TX (US)

(73) Assignee: 3SPINE, Inc., Chattanooga, TN (US)

( * ) Notice: Subject to any disclaimer, the term of this patent is extended or adjusted under 35 U.S.C. 154(b) by 90 days.

(21) Appl. No.: 18/371,426

(22) Filed: Sep. 21, 2023

(65) Prior Publication Data

US 2024/0009002 A1     Jan. 11, 2024

Related U.S. Application Data

(63) Continuation of application No. PCT/US2023/023600, filed on May 25, 2023, and a
(Continued)

(51) Int. Cl.
| | |
|---|---|
| A61F 2/44 | (2006.01) |
| A61B 17/56 | (2006.01) |
| A61B 34/10 | (2016.01) |
| A61F 2/46 | (2006.01) |
| G16H 20/40 | (2018.01) |

(52) U.S. Cl.
CPC ............ *A61F 2/4425* (2013.01); *A61B 17/56* (2013.01); *A61B 34/10* (2016.02); *A61F 2/442* (2013.01); *A61F 2/4611* (2013.01); *G16H*

*20/40* (2018.01); *A61B 2017/564* (2013.01); *A61B 2034/105* (2016.02); *A61B 2034/107* (2016.02);
(Continued)

(58) Field of Classification Search
CPC .......... A61F 2/44; A61F 2/442; A61F 2/4425; A61F 2/4611; A61B 17/56; A61B 2017/564
See application file for complete search history.

(56) References Cited

U.S. PATENT DOCUMENTS

| | | | |
|---|---|---|---|
| 3,320,951 A | 5/1967 | Wittebol | |
| 3,510,883 A | 5/1970 | Cathcart, III | |
| | | (Continued) | |

FOREIGN PATENT DOCUMENTS

| | | |
|---|---|---|
| CA | 2552361 A1 | 8/2005 |
| CH | 624573 A5 | 8/1981 |
| | (Continued) | |

OTHER PUBLICATIONS

European Patent Office, Office Action in European Patent Application No. 5705391, Annex to the Communication, European Patent Application No. 5705391, Jun. 2, 2009, 5 pages.
(Continued)

*Primary Examiner* — Ellen C Hammond
(74) *Attorney, Agent, or Firm* — BRAINSPARK ASSOCIATES, LLC

(57) ABSTRACT

Disclosed are devices, systems and methods for restoring spinal alignment and/or maximizing range of motion for patients who suffer from spinal degenerative disorders.

20 Claims, 55 Drawing Sheets

Related U.S. Application Data continuation-in-part of application No. PCT/US2022/074635, filed on Aug. 5, 2022.

(60) Provisional application No. 63/445,954, filed on Feb. 15, 2023, provisional application No. 63/375,379, filed on Sep. 12, 2022, provisional application No. 63/351,568, filed on Jun. 13, 2022, provisional application No. 63/345,560, filed on May 25, 2022.

(52) U.S. Cl.
CPC ... *A61B 2034/108* (2016.02); *A61F 2002/443* (2013.01); *A61F 2002/4633* (2013.01)

(56) References Cited

U.S. PATENT DOCUMENTS

| | | | |
|---|---|---|---|
| 3,740,769 A | 6/1973 | Haboush |
| 3,903,549 A | 9/1975 | Deyerle |
| 4,309,777 A | 1/1982 | Patil |
| 4,349,921 A | 9/1982 | Kuntz |
| 4,470,158 A | 9/1984 | Pappas et al. |
| 4,550,450 A | 11/1985 | Kinnett |
| 4,622,959 A | 11/1986 | Marcus |
| 4,653,487 A | 3/1987 | Maale |
| 4,681,589 A | 7/1987 | Tronzo |
| 4,697,582 A | 10/1987 | William |
| 4,697,586 A | 10/1987 | Gazale |
| 4,702,930 A | 10/1987 | Heide et al. |
| 4,743,262 A | 5/1988 | Tronzo |
| 4,759,766 A | 7/1988 | Buettner-Janz |
| 4,759,769 A | 7/1988 | Hedman et al. |
| 4,805,607 A | 2/1989 | Englehardt et al. |
| 4,836,196 A | 6/1989 | Park et al. |
| 4,874,389 A | 10/1989 | Downey |
| 4,875,474 A | 10/1989 | Border |
| 4,892,545 A | 1/1990 | Day et al. |
| 4,932,975 A | 6/1990 | Main et al. |
| 4,946,378 A | 8/1990 | Hirayama |
| 4,997,432 A | 3/1991 | Keller |
| 5,004,476 A | 4/1991 | Cook |
| 5,037,438 A | 8/1991 | Davidson |
| 5,062,850 A | 11/1991 | Macmillan et al. |
| 5,071,437 A | 12/1991 | Steffee |
| 5,092,866 A | 3/1992 | Breard |
| 5,108,442 A | 4/1992 | Smith |
| 5,122,130 A | 6/1992 | Keller |
| 5,258,031 A | 11/1993 | Salib et al. |
| 5,271,737 A | 12/1993 | Baldwin et al. |
| 5,282,863 A | 2/1994 | Burton |
| 5,282,868 A | 2/1994 | Bahler |
| 5,290,312 A | 3/1994 | Kojimoto et al. |
| 5,314,477 A | 5/1994 | Marnay |
| 5,344,458 A | 9/1994 | Bonutti |
| 5,387,213 A | 2/1995 | Breard et al. |
| 5,401,269 A | 3/1995 | Buttner-Janz et al. |
| 5,415,661 A | 5/1995 | Holmes |
| 5,423,825 A | 6/1995 | Levine |
| 5,425,773 A | 6/1995 | Boyd et al. |
| 5,443,513 A | 8/1995 | Moumene et al. |
| 5,443,515 A | 8/1995 | Cohen et al. |
| 5,507,816 A | 4/1996 | Bullivant |
| 5,509,934 A | 4/1996 | Cohen |
| 5,534,029 A | 7/1996 | Shima |
| 5,534,030 A | 7/1996 | Navarro et al. |
| 5,554,191 A | 9/1996 | Lahille et al. |
| 5,554,194 A | 9/1996 | Sanders |
| 5,556,431 A | 9/1996 | Buttner-Janz |
| 5,562,660 A | 10/1996 | Grob |
| 5,562,737 A | 10/1996 | Graf |
| 5,562,738 A | 10/1996 | Boyd et al. |
| 5,571,109 A | 11/1996 | Bertangoli |
| 5,571,190 A | 11/1996 | Ulrich et al. |
| 5,591,235 A | 1/1997 | Kuslich |
| 5,607,425 A | 3/1997 | Rogozinski |
| 5,609,638 A | 3/1997 | Price et al. |
| 5,658,347 A | 8/1997 | Sarkisian et al. |
| 5,672,175 A | 9/1997 | Martin |
| 5,674,294 A | 10/1997 | Bainville |
| 5,674,296 A | 10/1997 | Bryan et al. |
| 5,676,701 A | 10/1997 | Yuan et al. |
| 5,683,465 A | 11/1997 | Shinn et al. |
| 5,702,450 A | 12/1997 | Bisserie |
| 5,702,469 A | 12/1997 | Whipple et al. |
| 5,728,098 A | 3/1998 | Sherman et al. |
| 5,752,957 A | 5/1998 | Ralph et al. |
| 5,755,811 A | 5/1998 | Tanamal et al. |
| 5,772,661 A | 6/1998 | Michelson |
| 5,800,547 A | 9/1998 | Shafer et al. |
| 5,824,093 A | 10/1998 | Ray et al. |
| 5,824,094 A | 10/1998 | Serhan et al. |
| 5,888,222 A | 3/1999 | Coates et al. |
| 5,895,428 A | 4/1999 | Berry |
| 5,899,941 A | 5/1999 | Nishijima et al. |
| RE36,221 E | 6/1999 | Breard et al. |
| 5,928,284 A | 7/1999 | Mehdizadeh |
| 5,961,516 A | 10/1999 | Graf |
| 6,010,502 A | 1/2000 | Bagby |
| 6,019,792 A | 2/2000 | Cauthen |
| 6,039,763 A | 3/2000 | Shelokov |
| 6,042,582 A | 3/2000 | Ray |
| RE36,758 E | 6/2000 | Fitz |
| 6,096,080 A | 8/2000 | Nicholson et al. |
| 6,102,954 A | 8/2000 | Albrektsson et al. |
| 6,106,557 A | 8/2000 | Robioneck et al. |
| 6,113,637 A | 9/2000 | Gill et al. |
| 6,113,638 A | 9/2000 | Williams et al. |
| 6,132,464 A | 10/2000 | Martin |
| 6,146,421 A | 11/2000 | Gordon et al. |
| 6,156,067 A | 12/2000 | Bryan et al. |
| 6,159,211 A | 12/2000 | Boriani et al. |
| 6,159,214 A | 12/2000 | Michelson |
| 6,159,244 A | 12/2000 | Suddaby |
| 6,174,311 B1 | 1/2001 | Branch et al. |
| 6,179,874 B1 | 1/2001 | Cauthen |
| 6,179,875 B1 | 1/2001 | Strempel |
| 6,190,414 B1 | 2/2001 | Young et al. |
| 6,193,757 B1 | 2/2001 | Foley et al. |
| 6,200,322 B1 | 3/2001 | Branch et al. |
| 6,224,599 B1 | 5/2001 | Baynham et al. |
| 6,224,607 B1 | 5/2001 | Michelson |
| 6,228,118 B1 | 5/2001 | Gordon |
| 6,231,609 B1 | 5/2001 | Mehdizadeh |
| 6,235,059 B1 | 5/2001 | Benezech et al. |
| 6,238,396 B1 | 5/2001 | Lombardo |
| 6,251,112 B1 | 6/2001 | Jackson |
| 6,251,140 B1 | 6/2001 | Marino et al. |
| 6,264,655 B1 | 7/2001 | Pisharodi |
| 6,277,122 B1 | 8/2001 | Mcgahan et al. |
| 6,325,827 B1 | 12/2001 | Lin |
| 6,368,350 B1 | 4/2002 | Erickson et al. |
| 6,368,353 B1 | 4/2002 | Arcand |
| 6,375,681 B1 | 4/2002 | Truscott |
| 6,387,130 B1 | 5/2002 | Stone et al. |
| 6,402,750 B1 | 6/2002 | Atkinson et al. |
| 6,402,785 B1 | 6/2002 | Zdeblick et al. |
| 6,409,766 B1 | 6/2002 | Brett |
| 6,413,278 B1 | 7/2002 | Marchosky |
| 6,419,703 B1 | 7/2002 | Fallin et al. |
| 6,419,705 B1 | 7/2002 | Erickson |
| 6,432,140 B1 | 8/2002 | Lin |
| 6,440,139 B2 | 8/2002 | Michelson |
| 6,440,168 B1 | 8/2002 | Cauthen |
| 6,454,807 B1 | 9/2002 | Jackson |
| 6,471,724 B2 | 10/2002 | Zdeblick et al. |
| 6,514,260 B1 | 2/2003 | Zdeblick et al. |
| 6,517,580 B1 | 2/2003 | Ramadan et al. |
| 6,524,312 B2 | 2/2003 | Landry et al. |
| 6,527,804 B1 | 3/2003 | Gauchet et al. |
| 6,540,747 B1 | 4/2003 | Marino |
| 6,540,785 B1 | 4/2003 | Gill et al. |
| 6,562,074 B2 | 5/2003 | Gerbec et al. |
| 6,565,571 B1 | 5/2003 | Jackowski et al. |
| 6,565,574 B2 | 5/2003 | Michelson |

(56)          References Cited

U.S. PATENT DOCUMENTS

| | | |
|---|---|---|
| 6,565,605 B2 | 5/2003 | Goble et al. |
| 6,572,653 B1 | 6/2003 | Simonson |
| 6,579,319 B2 | 6/2003 | Goble et al. |
| 6,582,466 B1 | 6/2003 | Gauchet |
| 6,582,468 B1 | 6/2003 | Gauchet |
| 6,589,247 B2 | 7/2003 | Mcgahan et al. |
| 6,599,291 B1 | 7/2003 | Foley et al. |
| 6,607,557 B1 | 8/2003 | Brosnahan et al. |
| 6,610,065 B1 | 8/2003 | Branch et al. |
| 6,610,091 B1 | 8/2003 | Reiley |
| 6,610,093 B1 | 8/2003 | Pisharodi |
| 6,641,582 B1 | 11/2003 | Hanson et al. |
| 6,641,614 B1 | 11/2003 | Wagner et al. |
| 6,648,895 B2 | 11/2003 | Burkus et al. |
| 6,669,729 B2 | 12/2003 | Chin |
| 6,679,915 B1 | 1/2004 | Cauthen |
| 6,685,742 B1 | 2/2004 | Jackson |
| 6,692,495 B1 | 2/2004 | Zacouto |
| 6,699,247 B2 | 3/2004 | Zucherman et al. |
| 6,709,458 B2 | 3/2004 | Michelson |
| 6,733,532 B1 | 5/2004 | Gauchet et al. |
| 6,740,118 B2 | 5/2004 | Eisermann et al. |
| 6,743,255 B2 | 6/2004 | Ferree |
| 6,749,635 B1 | 6/2004 | Bryan |
| 6,780,186 B2 | 8/2004 | Errrico et al. |
| 6,805,714 B2 | 10/2004 | Sutcliffe |
| 6,811,567 B2 | 11/2004 | Reily |
| 6,908,484 B2 | 6/2005 | Zubok et al. |
| 6,936,071 B1 | 8/2005 | Marnay et al. |
| 6,949,123 B2 | 9/2005 | Reily |
| 6,958,077 B2 | 10/2005 | Suddaby |
| 6,966,929 B2 | 11/2005 | Mitchell |
| 6,984,245 B2 | 1/2006 | Mcgahan et al. |
| 6,984,246 B2 | 1/2006 | Huang |
| 6,986,772 B2 | 1/2006 | Michelson |
| 6,994,727 B2 | 2/2006 | Khandkar et al. |
| 7,025,787 B2 | 4/2006 | Bryan et al. |
| 7,044,971 B2 | 5/2006 | Suddaby |
| 7,052,515 B2 | 5/2006 | Simonson |
| 7,066,960 B1 | 6/2006 | Dickman |
| 7,070,598 B2 | 7/2006 | Lim et al. |
| 7,074,240 B2 | 7/2006 | Pisharodi |
| 7,083,649 B2 | 8/2006 | Zucherman et al. |
| 7,083,650 B2 | 8/2006 | Moskowitz et al. |
| 7,090,698 B2 | 8/2006 | Goble et al. |
| 7,128,761 B2 | 10/2006 | Kuras et al. |
| 7,137,985 B2 | 11/2006 | Jahng |
| 7,147,665 B1 | 12/2006 | Bryan et al. |
| 7,282,065 B2 | 10/2007 | Kirschman |
| 7,291,150 B2 | 11/2007 | Graf |
| 7,311,732 B2 | 12/2007 | Link et al. |
| 7,338,525 B2 | 3/2008 | Ferree |
| 7,338,527 B2 | 3/2008 | Blatt et al. |
| 7,550,010 B2 | 6/2009 | Humphreys et al. |
| 7,556,651 B2 | 7/2009 | Humphreys et al. |
| 7,635,389 B2 | 12/2009 | Yu et al. |
| 7,660,623 B2 | 2/2010 | Hunter et al. |
| 7,771,479 B2 | 8/2010 | Humphreys et al. |
| 7,811,325 B2 | 10/2010 | Cannon et al. |
| 7,811,326 B2 | 10/2010 | Braddock, Jr. et al. |
| 7,875,077 B2 | 1/2011 | Humphreys et al. |
| 7,901,459 B2 | 3/2011 | Hodges et al. |
| 8,864,832 B2 | 10/2014 | Carls et al. |
| 9,675,272 B2 | 6/2017 | Selover et al. |
| 10,603,185 B2 | 3/2020 | Hovorka et al. |
| 10,751,127 B2 | 8/2020 | Dace et al. |
| 10,821,003 B2 * | 11/2020 | Peterman .............. A61F 2/4405 |
| 11,039,889 B2 | 6/2021 | Frey et al. |
| 11,158,405 B2 | 10/2021 | Benson et al. |
| 11,382,750 B2 | 7/2022 | Perszyk et al. |
| 2001/0005796 A1 | 6/2001 | Zdeblick et al. |
| 2001/0010021 A1 | 7/2001 | Boyd et al. |
| 2001/0016773 A1 | 8/2001 | Serhan et al. |
| 2001/0016774 A1 | 8/2001 | Bresina et al. |
| 2001/0016775 A1 | 8/2001 | Scarborough et al. |
| 2001/0016776 A1 | 8/2001 | Zucherman et al. |
| 2001/0032020 A1 | 10/2001 | Besselink |
| 2001/0034553 A1 | 10/2001 | Michelson |
| 2001/0047207 A1 | 11/2001 | Michelson |
| 2001/0049560 A1 | 12/2001 | Paul et al. |
| 2002/0045943 A1 | 4/2002 | Uk |
| 2002/0049394 A1 | 4/2002 | Roy et al. |
| 2002/0049497 A1 | 4/2002 | Mason |
| 2002/0052656 A1 | 5/2002 | Michelson |
| 2002/0068976 A1 | 6/2002 | Jackson |
| 2002/0068977 A1 | 6/2002 | Jackson |
| 2002/0077702 A1 | 6/2002 | Castro |
| 2002/0095154 A1 | 7/2002 | Atkinson et al. |
| 2002/0095155 A1 | 7/2002 | Michelson |
| 2002/0099444 A1 | 7/2002 | Boyd et al. |
| 2002/0107572 A1 | 8/2002 | Foley et al. |
| 2002/0116065 A1 | 8/2002 | Jackson |
| 2002/0116066 A1 | 8/2002 | Chauvin et al. |
| 2002/0116067 A1 | 8/2002 | Mears et al. |
| 2002/0123806 A1 | 9/2002 | Reiley |
| 2002/0128712 A1 | 9/2002 | Michelson |
| 2002/0128713 A1 | 9/2002 | Ferree |
| 2002/0133155 A1 | 9/2002 | Ferree |
| 2002/0138143 A1 | 9/2002 | Grooms et al. |
| 2002/0138146 A1 | 9/2002 | Jackson |
| 2002/0143399 A1 | 10/2002 | Sutcliffe |
| 2002/0151895 A1 | 10/2002 | Soboleski et al. |
| 2002/0151976 A1 | 10/2002 | Foley et al. |
| 2002/0156528 A1 | 10/2002 | Gau |
| 2002/0161366 A1 | 10/2002 | Robie et al. |
| 2002/0169508 A1 | 11/2002 | Songer et al. |
| 2002/0183756 A1 | 12/2002 | Michelson |
| 2003/0004572 A1 | 1/2003 | Goble et al. |
| 2003/0004575 A1 | 1/2003 | Erickson |
| 2003/0009226 A1 | 1/2003 | Graf |
| 2003/0028250 A1 | 2/2003 | Reiley et al. |
| 2003/0040797 A1 | 2/2003 | Fallin et al. |
| 2003/0045939 A1 | 3/2003 | Casutt |
| 2003/0055427 A1 | 3/2003 | Graf |
| 2003/0074068 A1 | 4/2003 | Errico et al. |
| 2003/0078666 A1 | 4/2003 | Ralph et al. |
| 2003/0100949 A1 | 5/2003 | Michelson |
| 2003/0120348 A1 | 6/2003 | Brosnahan et al. |
| 2003/0135278 A1 | 7/2003 | Eckman |
| 2003/0139812 A1 | 7/2003 | Garcia et al. |
| 2003/0139813 A1 | 7/2003 | Messerli et al. |
| 2003/0153984 A1 | 8/2003 | Khandkar |
| 2003/0171813 A1 | 9/2003 | Kiester |
| 2003/0176923 A1 | 9/2003 | Keller et al. |
| 2003/0191532 A1 | 10/2003 | Goble et al. |
| 2003/0199981 A1 | 10/2003 | Ferree |
| 2003/0199982 A1 | 10/2003 | Bryan |
| 2003/0204259 A1 | 10/2003 | Goble et al. |
| 2003/0204260 A1 | 10/2003 | Ferree |
| 2003/0204261 A1 | 10/2003 | Eisermann et al. |
| 2003/0204271 A1 | 10/2003 | Grinberg et al. |
| 2003/0208273 A1 | 11/2003 | Eisermann et al. |
| 2003/0233146 A1 | 12/2003 | Gringberg et al. |
| 2004/0002712 A1 | 1/2004 | Grinberg et al. |
| 2004/0002761 A1 | 1/2004 | Rogers et al. |
| 2004/0002762 A1 | 1/2004 | Hawkins |
| 2004/0006391 A1 | 1/2004 | Reiley |
| 2004/0024462 A1 | 2/2004 | Ferree et al. |
| 2004/0030390 A1 | 2/2004 | Ferree |
| 2004/0030391 A1 | 2/2004 | Ferree |
| 2004/0034430 A1 | 2/2004 | Falahee |
| 2004/0039385 A1 | 2/2004 | Mazda et al. |
| 2004/0039448 A1 | 2/2004 | Pisharodi |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049279 A1 | 3/2004 | Sevrain |
| 2004/0049281 A1 | 3/2004 | Reiley |
| 2004/0068318 A1 | 4/2004 | Coates et al. |

(56)                    References Cited

U.S. PATENT DOCUMENTS

| | | |
|---|---|---|
| 2004/0073311 A1 | 4/2004 | Ferree |
| 2004/0097931 A1 | 5/2004 | Mitchell |
| 2004/0098131 A1 | 5/2004 | Bryan et al. |
| 2004/0102848 A1 | 5/2004 | Michelson |
| 2004/0111161 A1 | 6/2004 | Trieu |
| 2004/0126407 A1 | 7/2004 | Falahee |
| 2004/0127991 A1 | 7/2004 | Ferree |
| 2004/0133281 A1 | 7/2004 | Khandkar et al. |
| 2004/0138749 A1 | 7/2004 | Zucherman et al. |
| 2004/0143270 A1 | 7/2004 | Zucherman et al. |
| 2004/0143332 A1 | 7/2004 | Krueger et al. |
| 2004/0162562 A1 | 8/2004 | Martz |
| 2004/0162618 A1 | 8/2004 | Mujwid et al. |
| 2004/0176764 A1 | 9/2004 | Dant |
| 2004/0176845 A1 | 9/2004 | Zubok et al. |
| 2004/0176850 A1 | 9/2004 | Zubok et al. |
| 2004/0181284 A1 | 9/2004 | Simonson |
| 2004/0181285 A1 | 9/2004 | Simonson |
| 2004/0186570 A1 | 9/2004 | Rapp |
| 2004/0186576 A1 | 9/2004 | Biscup et al. |
| 2004/0186577 A1 | 9/2004 | Ferree |
| 2004/0193272 A1 | 9/2004 | Zubok et al. |
| 2004/0220567 A1 | 11/2004 | Eisermann et al. |
| 2004/0220670 A1 | 11/2004 | Eisermann et al. |
| 2004/0220672 A1 | 11/2004 | Shadduck |
| 2004/0225370 A1 | 11/2004 | Cruchet |
| 2004/0230307 A1 | 11/2004 | Eisermann |
| 2004/0243240 A1 | 12/2004 | Beaurain et al. |
| 2004/0243241 A1 | 12/2004 | Istephanous et al. |
| 2004/0249461 A1 | 12/2004 | Ferree |
| 2004/0249462 A1 | 12/2004 | Huang |
| 2004/0254643 A1 | 12/2004 | Jackson |
| 2005/0027359 A1 | 2/2005 | Mashburn |
| 2005/0033432 A1 | 2/2005 | Gordon et al. |
| 2005/0033439 A1 | 2/2005 | Gordon et al. |
| 2005/0038511 A1 | 2/2005 | Martz et al. |
| 2005/0043800 A1 | 2/2005 | Paul et al. |
| 2005/0043802 A1 | 2/2005 | Eisermann et al. |
| 2005/0055099 A1 | 3/2005 | Ku |
| 2005/0071008 A1 | 3/2005 | Kirschman |
| 2005/0075644 A1 | 4/2005 | Dipoto et al. |
| 2005/0080488 A1 | 4/2005 | Schultz |
| 2005/0113916 A1 | 5/2005 | Branch, Jr. |
| 2005/0113920 A1 | 5/2005 | Foley et al. |
| 2005/0119747 A1 | 6/2005 | Fabris Monterumici et al. |
| 2005/0119753 A1 | 6/2005 | Mcgahan et al. |
| 2005/0131540 A1 | 6/2005 | Trieu |
| 2005/0143820 A1 | 6/2005 | Zucherman et al. |
| 2005/0149189 A1 | 7/2005 | Mokhtar et al. |
| 2005/0149196 A1 | 7/2005 | Zucherman et al. |
| 2005/0154461 A1 | 7/2005 | Humphreys et al. |
| 2005/0154462 A1 | 7/2005 | Zucherman et al. |
| 2005/0154464 A1 | 7/2005 | Humphreys et al. |
| 2005/0154465 A1 | 7/2005 | Hodges et al. |
| 2005/0154466 A1 | 7/2005 | Humphreys et al. |
| 2005/0154467 A1 | 7/2005 | Peterman et al. |
| 2005/0159818 A1 | 7/2005 | Blain |
| 2005/0165407 A1 | 7/2005 | Diaz |
| 2005/0165484 A1 | 7/2005 | Ferree |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0187625 A1 | 8/2005 | Wolek et al. |
| 2005/0192671 A1 | 9/2005 | Bao et al. |
| 2005/0197702 A1 | 9/2005 | Coppes et al. |
| 2005/0209698 A1 | 9/2005 | Gordon et al. |
| 2005/0216081 A1 | 9/2005 | Taylor |
| 2005/0228500 A1 | 10/2005 | Kim et al. |
| 2005/0234551 A1 | 10/2005 | Fallin et al. |
| 2005/0234555 A1 | 10/2005 | Sutton et al. |
| 2005/0240270 A1 | 10/2005 | Zubock et al. |
| 2005/0251261 A1 | 11/2005 | Peterman |
| 2005/0256578 A1 | 11/2005 | Blatt et al. |
| 2005/0261773 A1 | 11/2005 | Ferree |
| 2005/0261774 A1 | 11/2005 | Trieu |
| 2005/0267581 A1 | 12/2005 | Marnay et al. |
| 2005/0273178 A1 | 12/2005 | Boyan et al. |
| 2005/0277930 A1 | 12/2005 | Parsons |
| 2005/0277938 A1 | 12/2005 | Parsons |
| 2005/0283237 A1 | 12/2005 | Zucherman et al. |
| 2005/0283242 A1 | 12/2005 | Zucherman et al. |
| 2006/0004448 A1 | 1/2006 | Casey |
| 2006/0009849 A1 | 1/2006 | Reiley |
| 2006/0025862 A1 | 2/2006 | Villiers et al. |
| 2006/0036325 A1 | 2/2006 | Paul et al. |
| 2006/0064170 A1 | 3/2006 | Smith et al. |
| 2006/0069437 A1 | 3/2006 | Weber |
| 2006/0069438 A1 | 3/2006 | Zucherman et al. |
| 2006/0069440 A1 | 3/2006 | Zucherman et al. |
| 2006/0085076 A1 | 4/2006 | Krishna et al. |
| 2006/0089717 A1 | 4/2006 | Krishna et al. |
| 2006/0095133 A1 | 5/2006 | Eisermann et al. |
| 2006/0106459 A1 | 5/2006 | Truckai et al. |
| 2006/0116768 A1 | 6/2006 | Krueger et al. |
| 2006/0129160 A1 | 6/2006 | Liu |
| 2006/0142860 A1 | 6/2006 | Navarro et al. |
| 2006/0178744 A1 | 8/2006 | De Villers et al. |
| 2006/0178745 A1 | 8/2006 | Bartish et al. |
| 2006/0241769 A1 | 10/2006 | Gordon et al. |
| 2006/0241771 A1 | 10/2006 | Gordon et al. |
| 2006/0247650 A1 | 11/2006 | Yerby et al. |
| 2006/0247769 A1 | 11/2006 | Molz et al. |
| 2007/0050033 A1 | 3/2007 | Reo |
| 2007/0050037 A1 | 3/2007 | Snell et al. |
| 2007/0055378 A1 | 3/2007 | Ankney et al. |
| 2007/0103459 A1 | 5/2007 | Stoval et al. |
| 2007/0179616 A1 | 8/2007 | Braddock, Jr. et al. |
| 2007/0191945 A1 | 8/2007 | Yu et al. |
| 2007/0270862 A1 | 11/2007 | Yu et al. |
| 2007/0270972 A1 | 11/2007 | Gordon |
| 2008/0015693 A1 | 1/2008 | Le Couedic |
| 2008/0027547 A1 | 1/2008 | Yu et al. |
| 2008/0045968 A1 | 2/2008 | Yu et al. |
| 2008/0300685 A1 | 12/2008 | Carls et al. |
| 2011/0028600 A1 | 2/2011 | Rufner |
| 2011/0077508 A1 | 3/2011 | Simon |
| 2014/0081659 A1 | 3/2014 | Nawana et al. |
| 2014/0100658 A1 | 4/2014 | Schmura et al. |
| 2015/0005884 A1 | 1/2015 | Carls et al. |
| 2020/0337777 A1 | 10/2020 | Liu et al. |
| 2021/0322178 A1 | 10/2021 | Peterman et al. |
| 2021/0378752 A1 | 12/2021 | Paul et al. |

FOREIGN PATENT DOCUMENTS

| | | |
|---|---|---|
| CN | 1713866 A | 12/2005 |
| CN | 1917832 A | 2/2007 |
| CN | 1976651 A | 6/2007 |
| CN | 1925799 B | 10/2010 |
| CN | 101969888 A | 2/2011 |
| CN | 102049782 A | 5/2011 |
| CN | 102049785 A | 5/2011 |
| CN | 103293057 A | 9/2013 |
| CN | 103908359 A | 7/2014 |
| CN | 105877878 A | 8/2016 |
| CN | 106236329 A | 12/2016 |
| CN | 107982582 A | 5/2018 |
| CN | 111973324 A | 11/2020 |
| DE | 2804936 A1 | 8/1979 |
| DE | 3023353 A1 | 4/1983 |
| DE | 20017962 U1 | 1/2001 |
| DE | 10135771 A1 | 2/2003 |
| DE | 202004015198 U1 | 11/2004 |
| EP | 0042271 A1 | 9/1984 |
| EP | 0640326 A1 | 3/1995 |
| EP | 0677277 A2 | 10/1995 |
| EP | 0716840 A2 | 6/1996 |
| EP | 0277282 A1 | 10/1998 |
| EP | 0953317 A1 | 11/1999 |
| EP | 1281361 A1 | 2/2003 |
| EP | 0820731 B1 | 5/2003 |
| EP | 0886506 B1 | 4/2005 |
| EP | 1685811 A | 8/2006 |
| EP | 1685811 A1 | 8/2006 |

(56)  References Cited

FOREIGN PATENT DOCUMENTS

| EP | 1711134 A1 | 10/2006 |
|---|---|---|
| EP | 1711137 A2 | 10/2006 |
| EP | 1711141 B1 | 10/2006 |
| EP | 1711135 B1 | 3/2013 |
| EP | 1711138 B1 | 3/2013 |
| EP | 1711139 B1 | 3/2013 |
| EP | 1711140 B1 | 3/2013 |
| EP | 2247266 B1 | 3/2013 |
| EP | 2793759 A4 | 8/2015 |
| EP | 2890314 A4 | 7/2016 |
| EP | 3357459 A1 | 8/2018 |
| EP | 3463202 A4 | 4/2019 |
| FR | 2676911 A1 | 12/1992 |
| FR | 2724108 A1 | 9/1994 |
| FR | 2718635 A1 | 10/1995 |
| FR | 2742653 A1 | 12/1995 |
| FR | 2723841 A1 | 3/1996 |
| FR | 2799638 A1 | 4/2001 |
| FR | 3075032 A1 | 6/2019 |
| JP | 63145650 A | 6/1988 |
| JP | 2261446 A | 10/1990 |
| JP | 10501705 A | 2/1998 |
| JP | 10286262 A | 10/1998 |
| JP | 2001511392 A | 8/2001 |
| JP | 2002512079 A | 4/2002 |
| JP | 2002521090 A | 7/2002 |
| JP | 2002528223 A | 9/2002 |
| JP | 2002532142 A | 10/2002 |
| JP | 2003512090 A | 4/2003 |
| JP | 2003515381 A | 5/2003 |
| JP | 2003518978 A | 6/2003 |
| JP | 2004514498 A | 5/2004 |
| JP | 2004167254 A | 6/2004 |
| JP | 2005503861 A | 2/2005 |
| JP | 2005515002 A | 5/2005 |
| JP | 2005526550 A | 9/2005 |
| JP | 2006500078 A | 1/2006 |
| JP | 2006502274 A | 1/2006 |
| JP | 2007517607 A | 7/2007 |
| JP | 2007517620 A | 7/2007 |
| JP | 2007517621 A | 7/2007 |
| JP | 2007519488 A | 7/2007 |
| JP | 2008517657 A | 5/2008 |
| JP | 4105721 B2 | 6/2008 |
| JP | 2008532642 A | 8/2008 |
| JP | 2009506843 A | 2/2009 |
| JP | 2011509747 A | 3/2011 |
| JP | 2013538605 A | 10/2013 |
| JP | 2014513579 A | 6/2014 |
| JP | 2014221399 A | 11/2014 |
| JP | 2016509911 A | 4/2016 |
| JP | 2016155023 A | 9/2016 |
| JP | 2019517372 A | 6/2019 |
| KR | 2010100129270 A | 12/2010 |
| MX | 06007862 A | 6/2007 |
| WO | 1993010725 A2 | 6/1993 |
| WO | 1996000049 A1 | 1/1996 |
| WO | 1997035529 A1 | 10/1997 |
| WO | 1998014142 A1 | 4/1998 |
| WO | 1999008627 A1 | 2/1999 |
| WO | 1999053871 A1 | 10/1999 |
| WO | 2000004851 A1 | 2/2000 |
| WO | 2000041654 A2 | 7/2000 |
| WO | 2000069351 A1 | 11/2000 |
| WO | 2001039678 A1 | 6/2001 |
| WO | 2001045576 A1 | 6/2001 |
| WO | 2002011650 A2 | 2/2002 |
| WO | 2002043603 A1 | 6/2002 |
| WO | 2002047586 A1 | 6/2002 |
| WO | 2003026522 A2 | 4/2003 |
| WO | 2003041618 A2 | 5/2003 |
| WO | 2003045262 A2 | 6/2003 |
| WO | 2003059212 A1 | 7/2003 |
| WO | 2003084449 A1 | 10/2003 |
| WO | 2003101350 A1 | 4/2004 |
| WO | 2004034935 A1 | 4/2004 |
| WO | 2004041131 A2 | 5/2004 |
| WO | 2004098465 A1 | 11/2004 |
| WO | 2005011522 A2 | 2/2005 |
| WO | 2005025431 A | 3/2005 |
| WO | 2005070354 A2 | 4/2005 |
| WO | 2005067824 A1 | 7/2005 |
| WO | 2005070278 A2 | 8/2005 |
| WO | 2005070349 A1 | 8/2005 |
| WO | 2005070350 A2 | 8/2005 |
| WO | 2005070352 A2 | 8/2005 |
| WO | 2005070353 A1 | 8/2005 |
| WO | 2005077304 A1 | 8/2005 |
| WO | 2005094736 A1 | 10/2005 |
| WO | 2005112835 A2 | 12/2005 |
| WO | 2005117725 A2 | 12/2005 |
| WO | 2006063354 A1 | 6/2006 |
| WO | 2007028098 A2 | 3/2007 |
| WO | 2007087477 A1 | 8/2007 |
| WO | 2007089972 A2 | 8/2007 |
| WO | 2007124467 A2 | 11/2007 |
| WO | 2008005252 A1 | 1/2008 |
| WO | 2008094881 A1 | 8/2008 |
| WO | 2014018802 A1 | 1/2014 |
| WO | 2018195118 A1 | 10/2018 |
| WO | 2018200767 A1 | 11/2018 |
| WO | 2020097613 A2 | 5/2020 |
| WO | 2022072806 A1 | 4/2022 |

OTHER PUBLICATIONS

European Patent Office, Office Action in European Patent Application No. 5705390, Annex to the Communication, European Patent Application No. 5705390, Jun. 2, 2009, 6 pages.

European Patent Office, Office Action in European Patent Application No. 5705305, Annex to the Communication, European Patent Application No. 5705305, Jun. 2, 2009, 7 pages.

European Patent Office, Office Action in European Patent Application No. 5705392, Annex to the Communication, European Patent Application No. 5705392, Jun. 2, 2009, 7 pages.

European Patent Office, Office Action in European Patent Application No. 9702495, Annex to the Communication, European Patent Application No. 9702495, Mar. 16, 2012, 5 pages.

European Patent Office, Supplementary Search Report and Written Opinion in European Patent Application No. 18787514, Annex to the Communication, European Patent Application No. 18787514, Dec. 23, 2020, 8 pages.

International Searching Authority, United States Patent and Trademark Office, International Search Report and Written Opinion for PCT Appl. No. PCT/US19/060800, Jan. 14, 2020, 9 pgs.

International Searching Authority, United States Patent and Trademark Office, International Search Report and Written Opinion for PCT Appl. No. PCT/US22/074635, Jan. 10, 2023, 15 pgs.

International Searching Authority, United States Patent and Trademark Office, International Search Report and Written Opinion for PCT Appl. No. PCT/US23/018341, Aug. 29, 2023, 16 pgs.

International Searching Authority, United States Patent and Trademark Office, International Search Report and Written Opinion for PCT Appl. No. PCT/US23/023600, Aug. 29, 2023, 19 pgs.

International Searching Authority, United States Patent and Trademark Office, International Search Report and Written Opinion for PCT Appl. No. PCT/US23/032543, Mar. 11, 2024, 15 pgs.

European Patent Office, Supplemental Search Report in European Patent Application No. 3612115, Dec. 20, 2023, 8 pages.

Australian Patent Office, Examination Report No. 1 in Australian Patent Application No. 2018255297, Jan. 30, 2023, 4 pages.

Applicant Communication, Applicant's Response to Examination Report No. 1 in Australian Patent Application No. 2018255297, Oct. 2, 2023, 7 pages.

Australian Patent Office, Notice of Acceptance of Australian Patent Application No. 2018255297, Nov. 7, 2023, 6 pages.

PCT—International Searching Authority, International Search Report and Written Opinion of the International Searching Authority for PCT/US2005/000648, Jun. 6, 2005, 12 pages.

(56)          References Cited

OTHER PUBLICATIONS

PCT—International Searching Authority, International Search Report and Written Opinion of the International Searching Authority for PCT/US2005/000705, Jun. 6, 2005, 13 pages.

PCT—European Patent Office, International Search Report and International Preliminary Examination Report for PCT/US2001/024791, Jun. 20, 2002, 8 pages.

PCT—International Searching Authority, International Search Report and Written Opinion of the International Searching Authority for Application No. PCT/US2005/000586, Dec. 16, 2005, 17 pages.

PCT—International Searching Authority, International Search Report and Written Opinion of the International Searching Authority for PCT/US2005/000706, Sep. 13, 2005, 19 pages.

PCT—International Searching Authority, International Search Report and Written Opinion of the International Searching Authority for PCT/US2007/060491, Apr. 25, 2007, 8 pages.

PCT—International Searching Authority, International Search Report and Written Opinion of the International Searching Authority for Application No. PCT/US2005/000656, Aug. 23, 2005, 12 pages.

PCT—International Searching Authority, International Search Report and Written Opinion of the International Searching Authority for Application No. PCT/US2005/000704, Aug. 23, 2005, 17 pages.

PCT—International Searching Authority, International Search Report and Written Opinion of the International Searching Authority for Application No. PCT/US2005/000585, Jun. 8, 2005, 12 pages.

TH. Marnay—Orthopedic Surgeon, Lumbar Intervertebral Arthroplasty—Jun.-Sep. 1991, 15 pages, Kennedy Clinic, U.S.A. (See French article in line item 11).

TH. Marnay—La Revue De Medecine Orthopedique, L'Arthoplatie Intervertebral Lombaire, No. 25, Jun.-Sep. 1991, 9 pages, Kennedy Clinic, France.

Ab Swanson, et al.—The Journal of Bone and Joint Surgery, Unicompartmental and Biocompartmental Arthroplasty of the Knee with a Finned Metal Tibial-Plateau Implant, Oct. 1985, 9 pages, J Bone Joint Surg Am. 1985;67:1175-1182, Needham, MA.

David S. Hungerford, M.D., Kenneth A. Krackow, M.D., Robert V. Kenna—Total Knee Arthroplasty: A Comprehensive Approach, 1984, 20 pages, Publisher Williams and Wilkins, Baltimore, MD.

David S. Hungerford, M.D., and Robert V. Kenna—Preliminary Experience with a Total Knee Prosthesis with Pourous Coating Used Without Cement, Jun. 1983, 13 pages, J.B.Lippincott, Co., No. 176, U.S.A.

T. Hoogland, A.D. Steffe, J.D. Black, A.S. Greenwald—Total Lumbar Intervertebral Disc Replacement: Testing of a New Articulating Spacer in Human Cadaver Spines, Feb. 21-23, 1978, 1 page, Cleveland Clinic Foundation, 24th Annual ORS, Dallas, TX.

Jeanette E. Ahrens, PHD, Alexis P Shelokov, MD, Jeffrey L. Carver, BS—Normal Joint Mobility is Maintained with an Artificial Disc Prosthesis, 1999, 4 pages, Texas Health Research Institute, Plano, Texas.

Zimmer—The Journal of Bone and Joint Surgery, Jul. 1970, 2 pages, American Volume, vol. 52-A, No. 5, Boston, MA.

Viscoglioski Bro., LLC, Spine Arthroplasty: Market Potential & Technology Update, Spine Industry Analysis Series, Nov. 2001, 202 pages, U.S.A.

A.H. Crenshaw—Campbell's Operative Orthopedics, 1987, 11 pages, Seventh Edition, vol. 2, The C.V. Mosby Company, 1987.

Zimmer—The Journal of Bone and Joint Surgery, Sep. 1971, 2 pages, American Volume, vol. 53-A, No. 6, Boston, MA.

International Search Authority, European Patent Office, International Search Report and Written Opinion for PCT Appl. No. PCT/US2008/065504, Dec. 1, 2009, 1-11 pgs.

Australian Patent Office, Patent Examination Report No. 1 for Pat. Appl. 2008259888, dated Sep. 28, 2012, 1-4 pgs.

European Patent Office, European Search Report for Pat. Appl. No. 18787514.1, Dec. 23, 2020, pp. 1-8.

International Search Authority, United States Patent & Trademark Office, International Search Report and Written Opinion for PCT Appl. No. PCT/US2018/028028, Jun. 27, 2018, pp. 1-8.

* cited by examiner

PREOPERATIVE METHOD

110 — Completing a Drug History & Drug Management Protocol

120 — Conducting a Health Behavior Assessment

130 — Completing the Enhanced Recovery After Surgery (ERAS) Protocol

140 — Acquiring At Least One Image Using the Imaging Protocol

FIG. 1

PREOPERATIVE IMAGING PROTOCOL

210 — Acquiring at Least One Image Using a First Imaging Technique

220 — Acquiring at Least One Image Using a Second Imaging Technique

230 — Acquiring at Least One Image Using a Third Imaging Technique

FIG. 2A

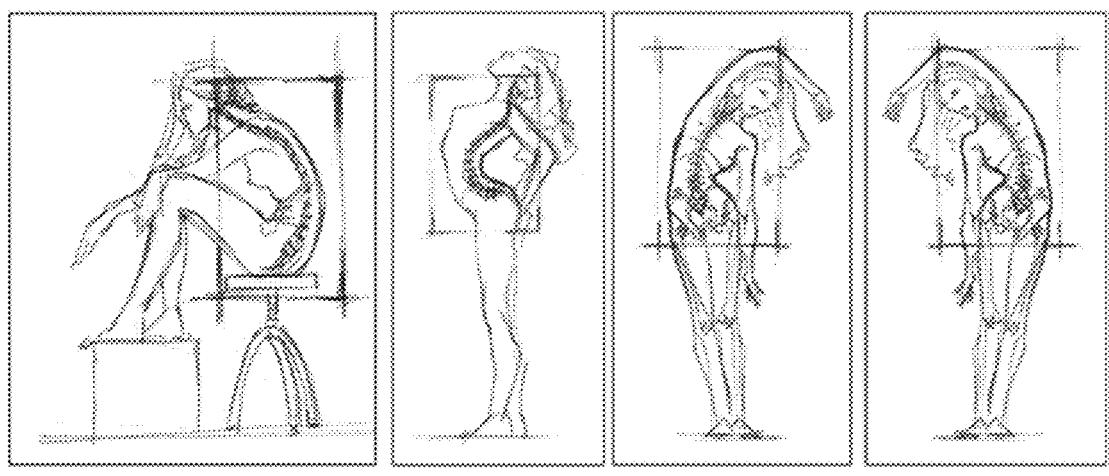

FIG. 2B

INTRAOPERATIVE PROCEDURE
(Alignment & Motion Restoration)

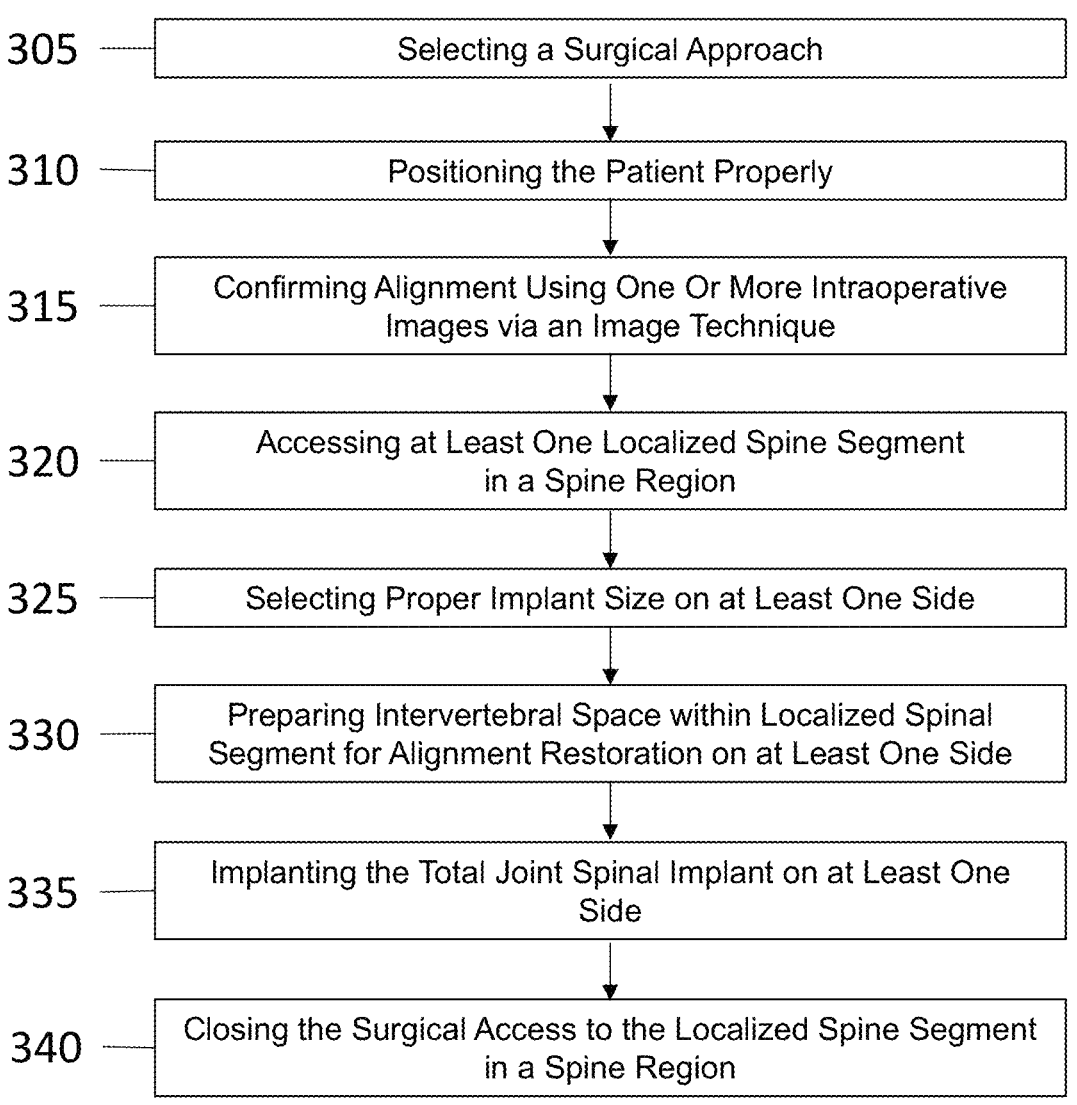

305 —— Selecting a Surgical Approach

310 —— Positioning the Patient Properly

315 —— Confirming Alignment Using One Or More Intraoperative Images via an Image Technique 320 —— Accessing at Least One Localized Spine Segment in a Spine Region 325 —— Selecting Proper Implant Size on at Least One Side 330 —— Preparing Intervertebral Space within Localized Spinal Segment for Alignment Restoration on at Least One Side 335 —— Implanting the Total Joint Spinal Implant on at Least One Side 340 —— Closing the Surgical Access to the Localized Spine Segment in a Spine Region

FIG. 3A

INTRAOPERATIVE PROCEDURE

ALIF
440

OLIF
ATP     430

XLIF
LLIF    420

TLIF
410

PLIF
400

PLIF

TLIF

LLIF

OLIF

ALIF

ACCESSING THE LOCALIZED SPINE SEGMENT
IN A SPINE REGION

500 — Completing Incision to Access Targeted Intervertebral Space
of a Spinal Segment with a Spinal Region 510 — Completing at Least One Decompression Technique on at
least One Side

COMPLETING AT LEAST ONE DECOMPRESSION
TECHNIQUE

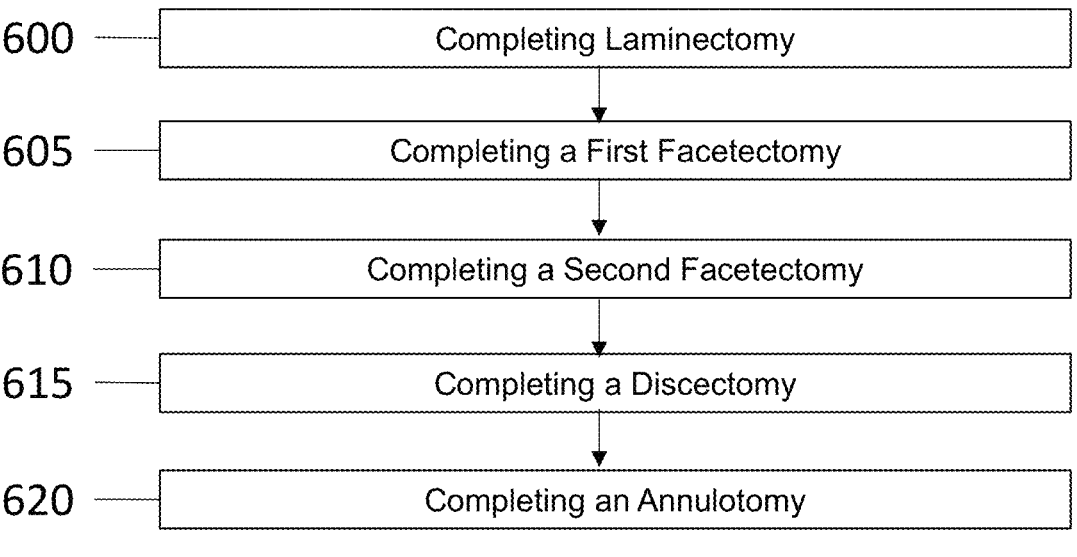

600 —— Completing Laminectomy

605 —— Completing a First Facetectomy

610 —— Completing a Second Facetectomy

615 —— Completing a Discectomy

620 —— Completing an Annulotomy

FIG. 6A

630 —— Completing Laminectomy

635 —— Completing a First Facetectomy

640 —— Completing a Second Facetectomy

645 —— Completing a First Discectomy

650 —— Completing a Second Discectomy

655 —— Completing a First Annulotomy

660 —— Completing a Second Annulotomy

FIG. 6B

SELECTING A PROPER SPINAL IMPLANT SIZE

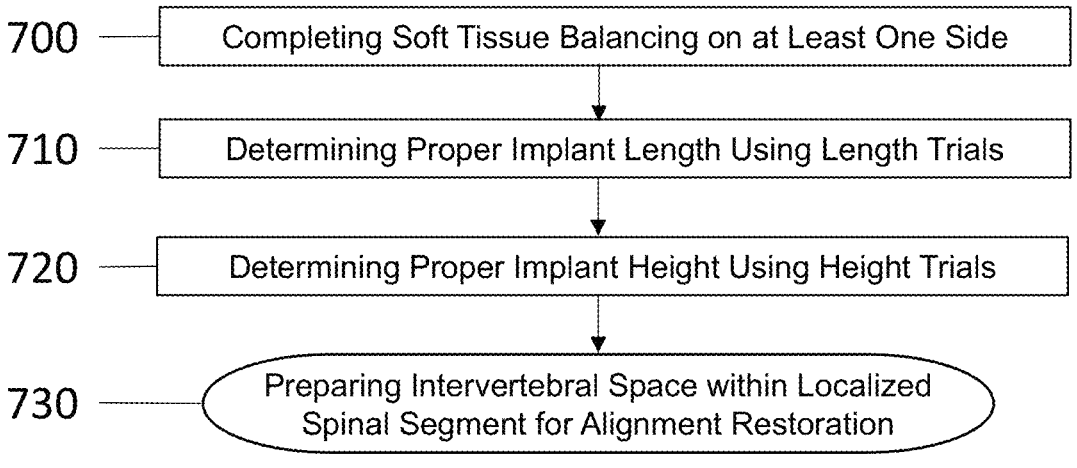

700 —— Completing Soft Tissue Balancing on at Least One Side

710 —— Determining Proper Implant Length Using Length Trials

720 —— Determining Proper Implant Height Using Height Trials

730 —— Preparing Intervertebral Space within Localized Spinal Segment for Alignment Restoration

FIG. 7A

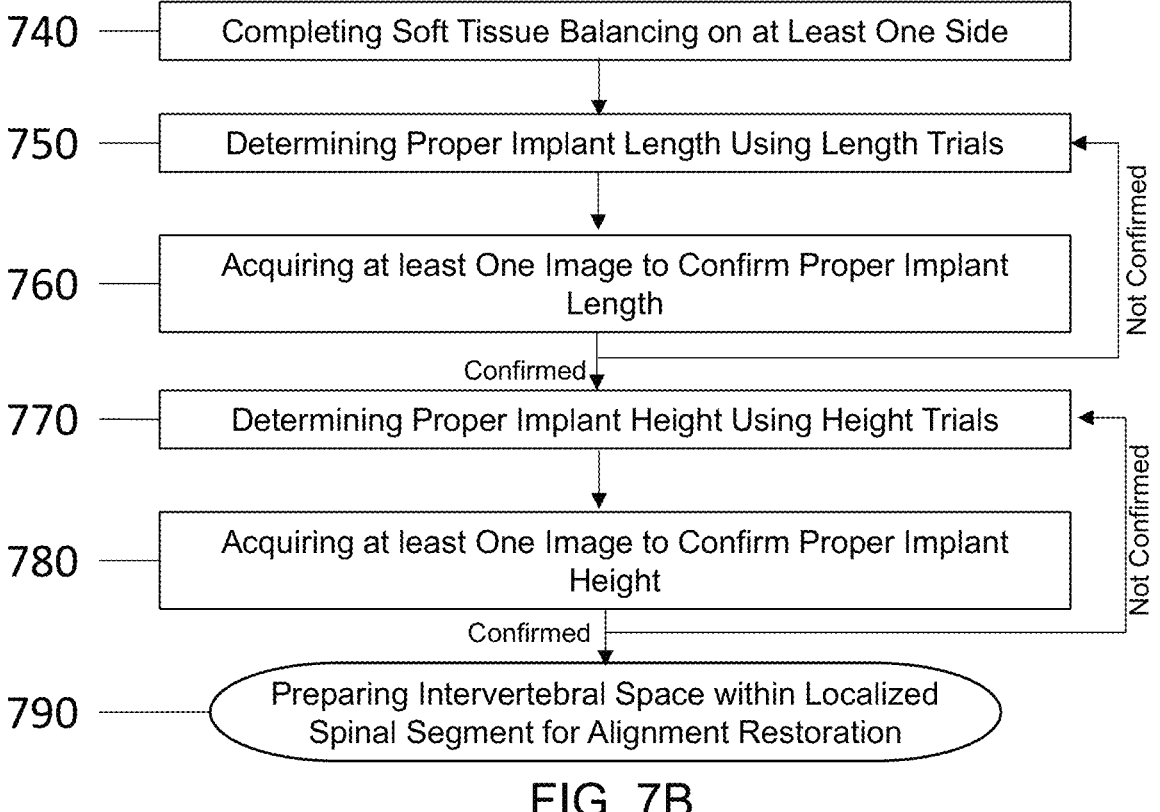

740 —— Completing Soft Tissue Balancing on at Least One Side

750 —— Determining Proper Implant Length Using Length Trials

760 —— Acquiring at least One Image to Confirm Proper Implant Length

Not Confirmed

Confirmed

770 —— Determining Proper Implant Height Using Height Trials

780 —— Acquiring at least One Image to Confirm Proper Implant Height

Not Confirmed

Confirmed

790 —— Preparing Intervertebral Space within Localized Spinal Segment for Alignment Restoration

FIG. 7B

DETERMINING PROPER SPINAL IMPLANT LENGTH

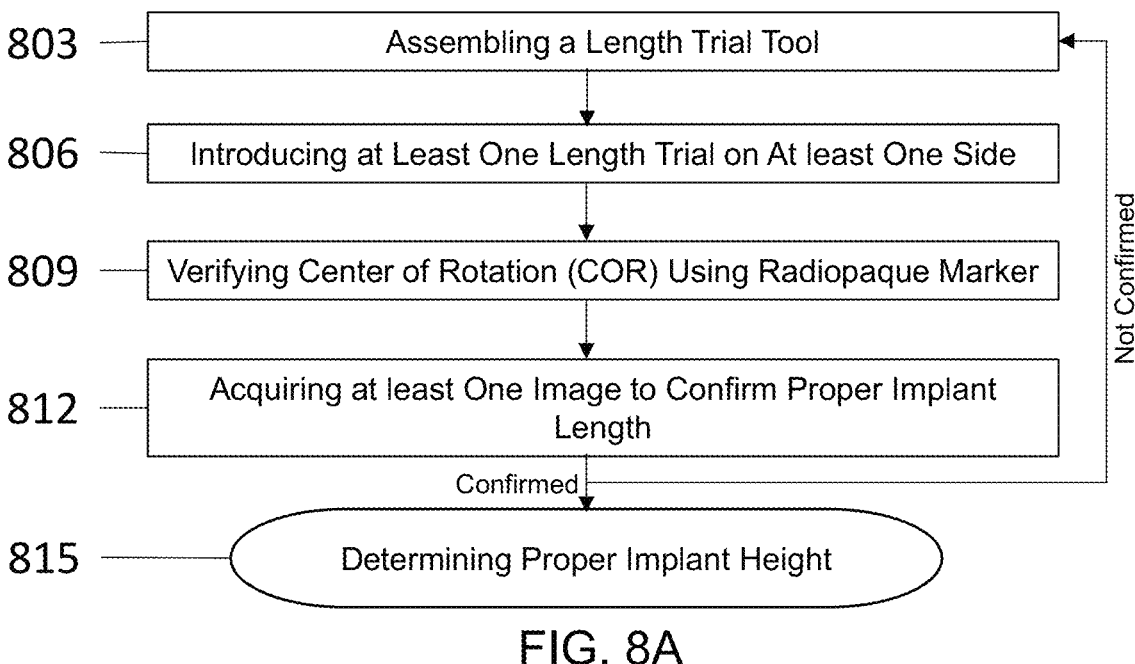

803 — Assembling a Length Trial Tool

806 — Introducing at Least One Length Trial on At least One Side

809 — Verifying Center of Rotation (COR) Using Radiopaque Marker

812 — Acquiring at least One Image to Confirm Proper Implant Length

Not Confirmed

Confirmed

815 — Determining Proper Implant Height

FIG. 8A

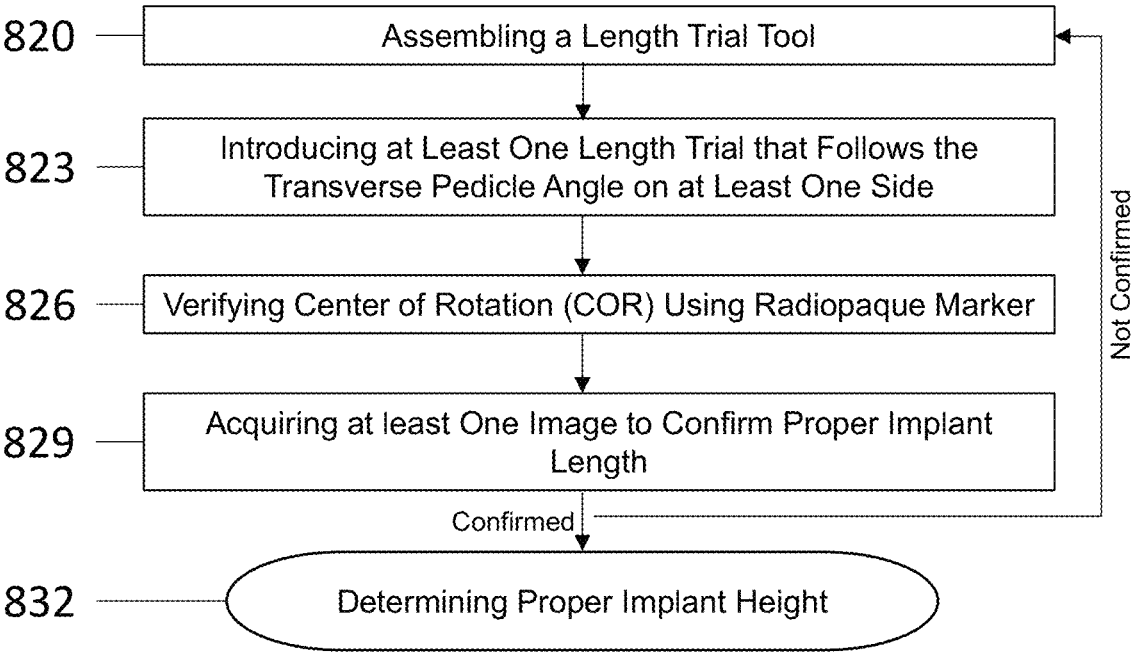

820 — Assembling a Length Trial Tool

823 — Introducing at Least One Length Trial that Follows the Transverse Pedicle Angle on at Least One Side 826 — Verifying Center of Rotation (COR) Using Radiopaque Marker 829 — Acquiring at least One Image to Confirm Proper Implant Length Not Confirmed Confirmed 832 — Determining Proper Implant Height

FIG. 8B

DETERMINING PROPER SPINAL IMPLANT LENGTH

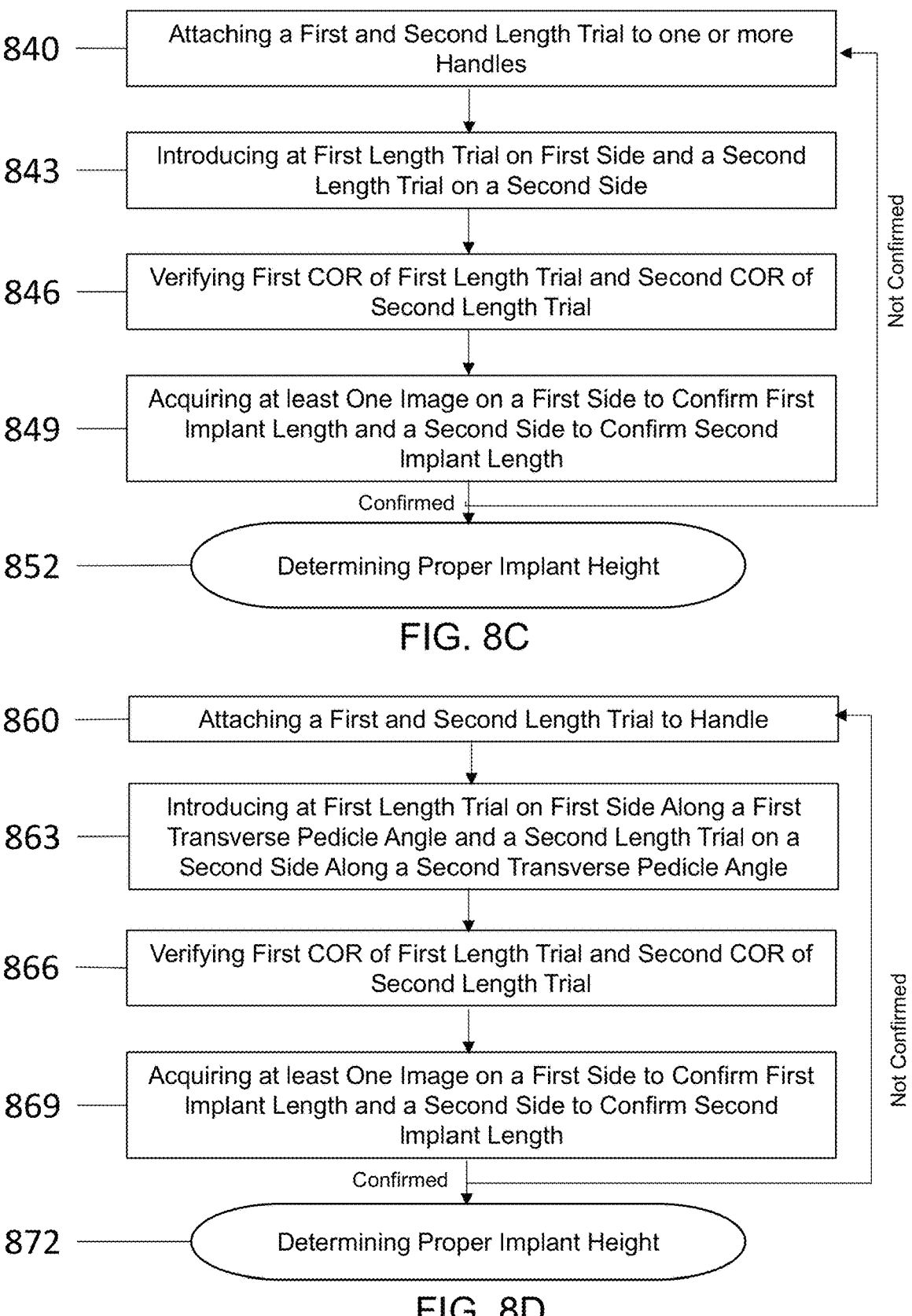

840 — Attaching a First and Second Length Trial to one or more Handles

843 — Introducing at First Length Trial on First Side and a Second Length Trial on a Second Side 846 — Verifying First COR of First Length Trial and Second COR of Second Length Trial 849 — Acquiring at least One Image on a First Side to Confirm First Implant Length and a Second Side to Confirm Second Implant Length Not Confirmed Confirmed 852 — Determining Proper Implant Height

FIG. 8C

860 — Attaching a First and Second Length Trial to Handle

863 — Introducing at First Length Trial on First Side Along a First Transverse Pedicle Angle and a Second Length Trial on a Second Side Along a Second Transverse Pedicle Angle 866 — Verifying First COR of First Length Trial and Second COR of Second Length Trial 869 — Acquiring at least One Image on a First Side to Confirm First Implant Length and a Second Side to Confirm Second Implant Length Not Confirmed Confirmed 872 — Determining Proper Implant Height

DETERMINING PROPER IMPLANT HEIGHT

DETERMINING PROPER IMPLANT HEIGHT

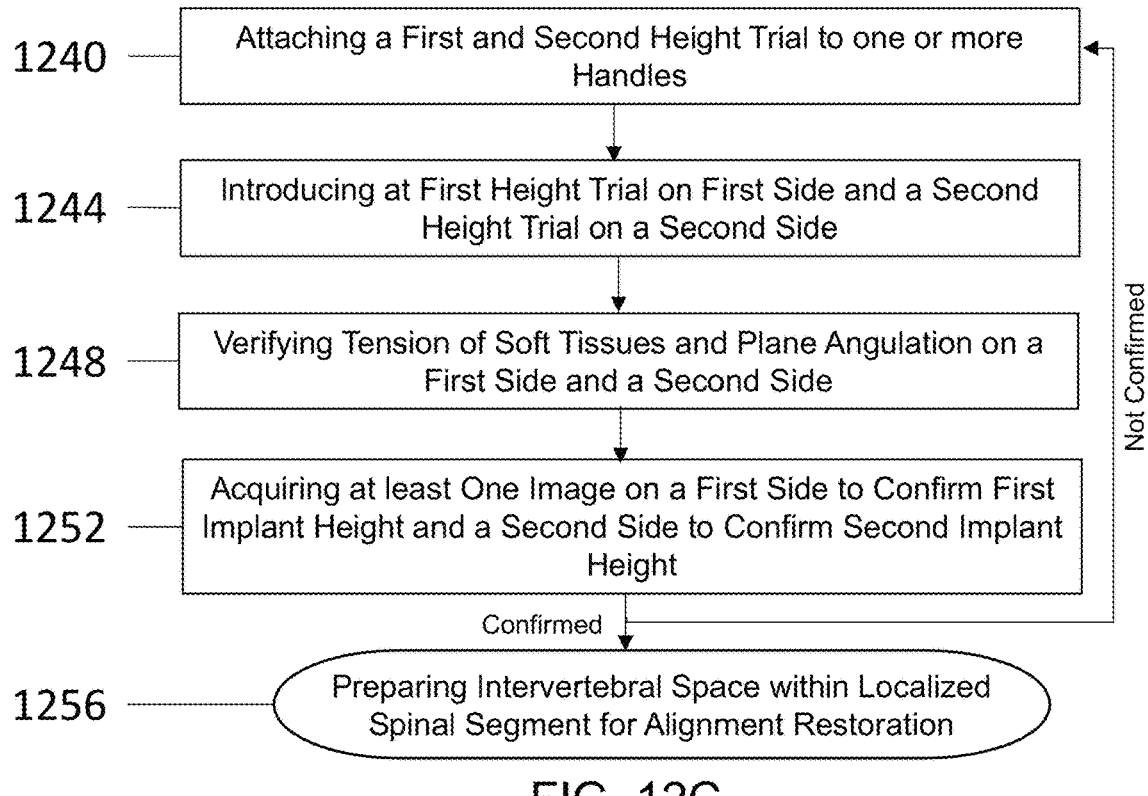

1240 — Attaching a First and Second Height Trial to one or more Handles

1244 — Introducing at First Height Trial on First Side and a Second Height Trial on a Second Side 1248 — Verifying Tension of Soft Tissues and Plane Angulation on a First Side and a Second Side 1252 — Acquiring at least One Image on a First Side to Confirm First Implant Height and a Second Side to Confirm Second Implant Height Not Confirmed Confirmed 1256 — Preparing Intervertebral Space within Localized Spinal Segment for Alignment Restoration

FIG. 12C

1260 — Attaching a First and Second Height Trial to Handle

1264 — Introducing at First Height Trial on First Side Along a First Transverse Pedicle Angle and a Second Height Trial on a Second Side Along a Second Transverse Pedicle Angle 1268 — Verifying Tension of Soft Tissues and Plane Angulation on a First Side and a Second Side 1272 — Acquiring at least One Image on a First Side to Confirm First Implant Length and a Second Side to Confirm Second Implant Length Not Confirmed Confirmed 1276 — Preparing Intervertebral Space within Localized Spinal Segment for Alignment Restoration

FIG. 12D

1300
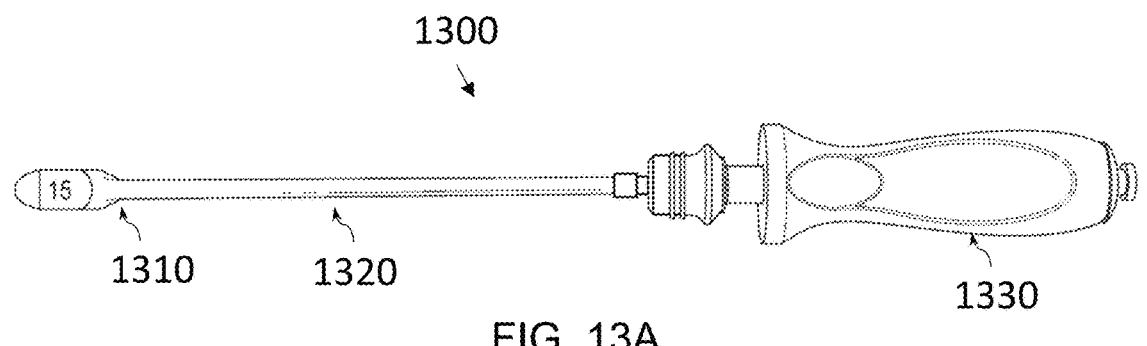
1310          1320
1330
FIG. 13A
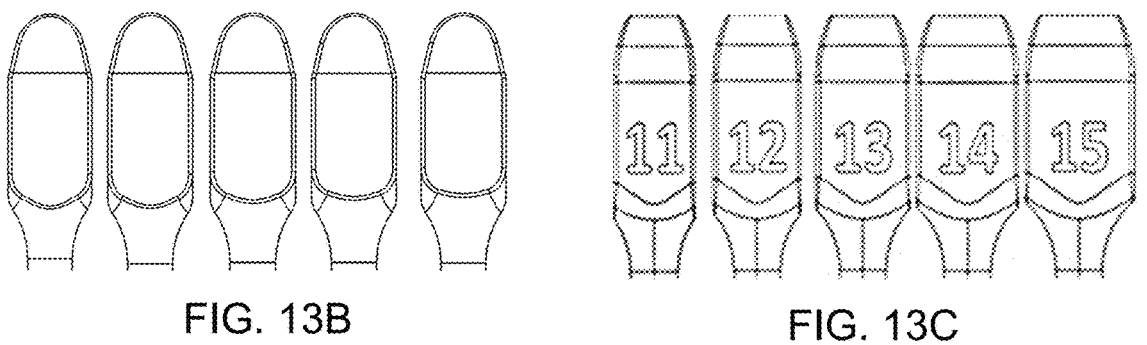
FIG. 13B
FIG. 13C
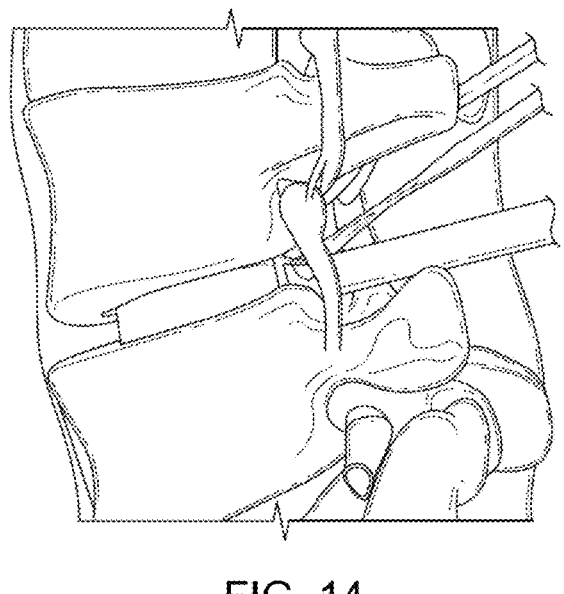
FIG. 14

PREPARING INTERVERTEBRAL SPACE WITHIN LOCALIZED
SPINAL SEGMENT FOR ALIGNMENT & MOTION RESTORATION

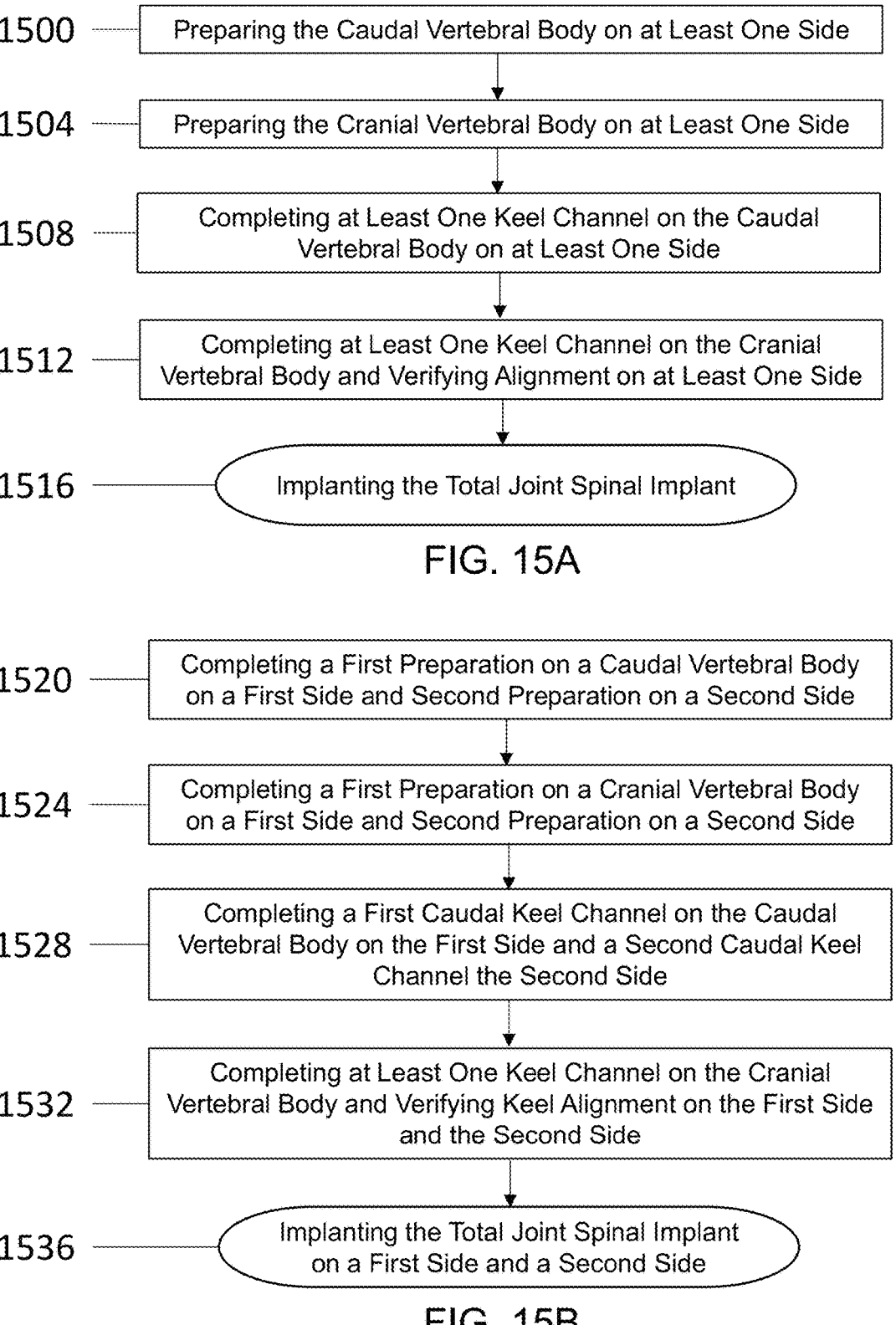

1500 —— Preparing the Caudal Vertebral Body on at Least One Side

1504 —— Preparing the Cranial Vertebral Body on at Least One Side

1508 —— Completing at Least One Keel Channel on the Caudal Vertebral Body on at Least One Side 1512 —— Completing at Least One Keel Channel on the Cranial Vertebral Body and Verifying Alignment on at Least One Side 1516 —— Implanting the Total Joint Spinal Implant

FIG. 15A

1520 —— Completing a First Preparation on a Caudal Vertebral Body on a First Side and Second Preparation on a Second Side 1524 —— Completing a First Preparation on a Cranial Vertebral Body on a First Side and Second Preparation on a Second Side 1528 —— Completing a First Caudal Keel Channel on the Caudal Vertebral Body on the First Side and a Second Caudal Keel Channel the Second Side 1532 —— Completing at Least One Keel Channel on the Cranial Vertebral Body and Verifying Keel Alignment on the First Side and the Second Side 1536 —— Implanting the Total Joint Spinal Implant on a First Side and a Second Side

FIG. 15B

PREPARING INTERVERTEBRAL SPACE WITHIN LOCALIZED
SPINAL SEGMENT FOR ALIGNMENT & MOTION RESTORATION

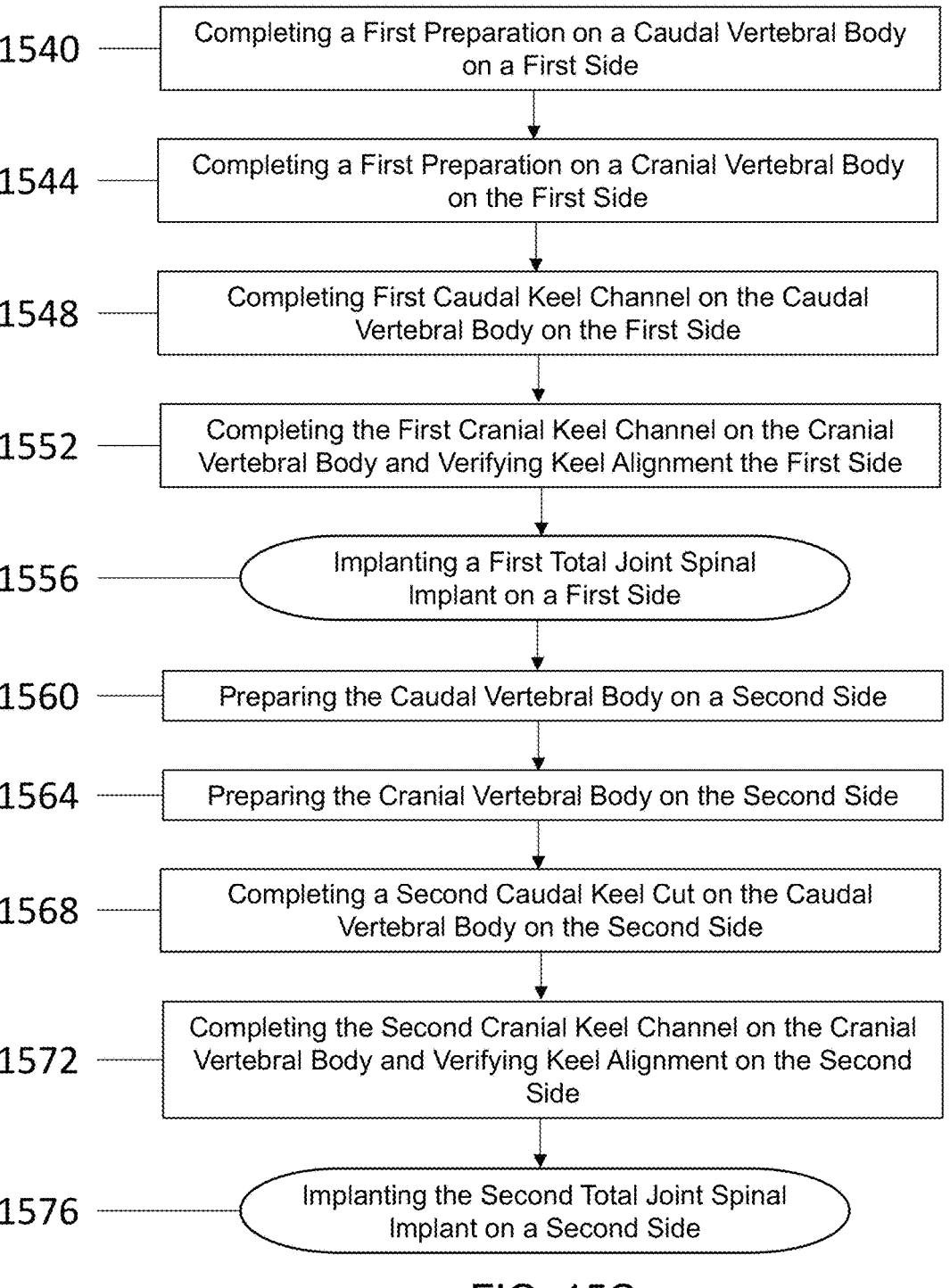

1540 — Completing a First Preparation on a Caudal Vertebral Body on a First Side 1544 — Completing a First Preparation on a Cranial Vertebral Body on the First Side 1548 — Completing First Caudal Keel Channel on the Caudal Vertebral Body on the First Side 1552 — Completing the First Cranial Keel Channel on the Cranial Vertebral Body and Verifying Keel Alignment the First Side 1556 — Implanting a First Total Joint Spinal Implant on a First Side 1560 — Preparing the Caudal Vertebral Body on a Second Side 1564 — Preparing the Cranial Vertebral Body on the Second Side 1568 — Completing a Second Caudal Keel Cut on the Caudal Vertebral Body on the Second Side 1572 — Completing the Second Cranial Keel Channel on the Cranial Vertebral Body and Verifying Keel Alignment on the Second Side 1576 — Implanting the Second Total Joint Spinal Implant on a Second Side

FIG. 15C

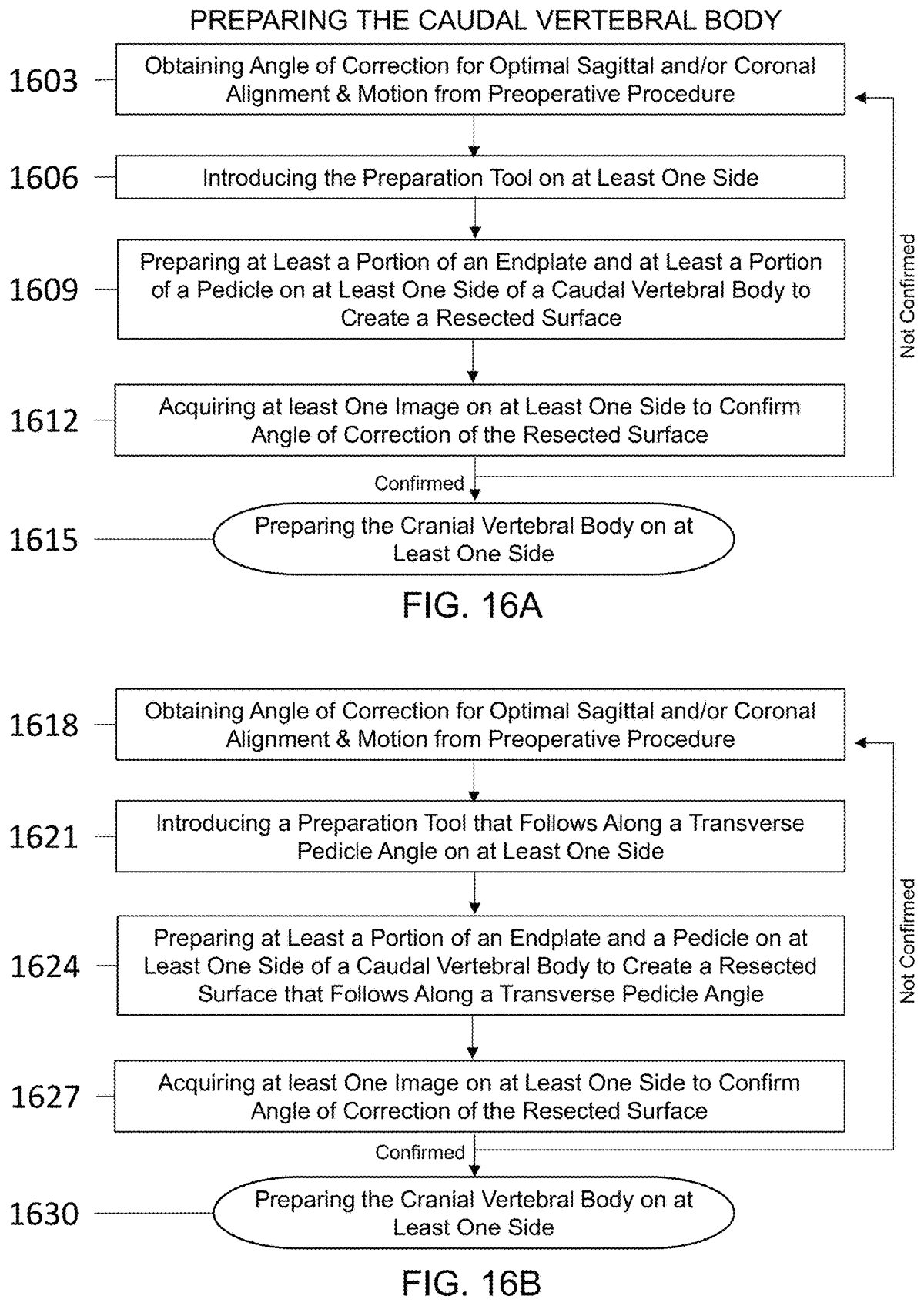

PREPARING THE CAUDAL VERTEBRAL BODY

1603 — | Obtaining Angle of Correction for Optimal Sagittal and/or Coronal Alignment & Motion from Preoperative Procedure |

1606 — | Introducing the Preparation Tool on at Least One Side |

1609 — | Preparing at Least a Portion of an Endplate and at Least a Portion of a Pedicle on at Least One Side of a Caudal Vertebral Body to Create a Resected Surface |

1612 — | Acquiring at least One Image on at Least One Side to Confirm Angle of Correction of the Resected Surface |

Not Confirmed

Confirmed

1615 — ( Preparing the Cranial Vertebral Body on at Least One Side )

FIG. 16A

1618 — | Obtaining Angle of Correction for Optimal Sagittal and/or Coronal Alignment & Motion from Preoperative Procedure |

1621 — | Introducing a Preparation Tool that Follows Along a Transverse Pedicle Angle on at Least One Side |

1624 — | Preparing at Least a Portion of an Endplate and a Pedicle on at Least One Side of a Caudal Vertebral Body to Create a Resected Surface that Follows Along a Transverse Pedicle Angle |

1627 — | Acquiring at least One Image on at Least One Side to Confirm Angle of Correction of the Resected Surface |

Not Confirmed

Confirmed

1630 — ( Preparing the Cranial Vertebral Body on at Least One Side )

FIG. 16B

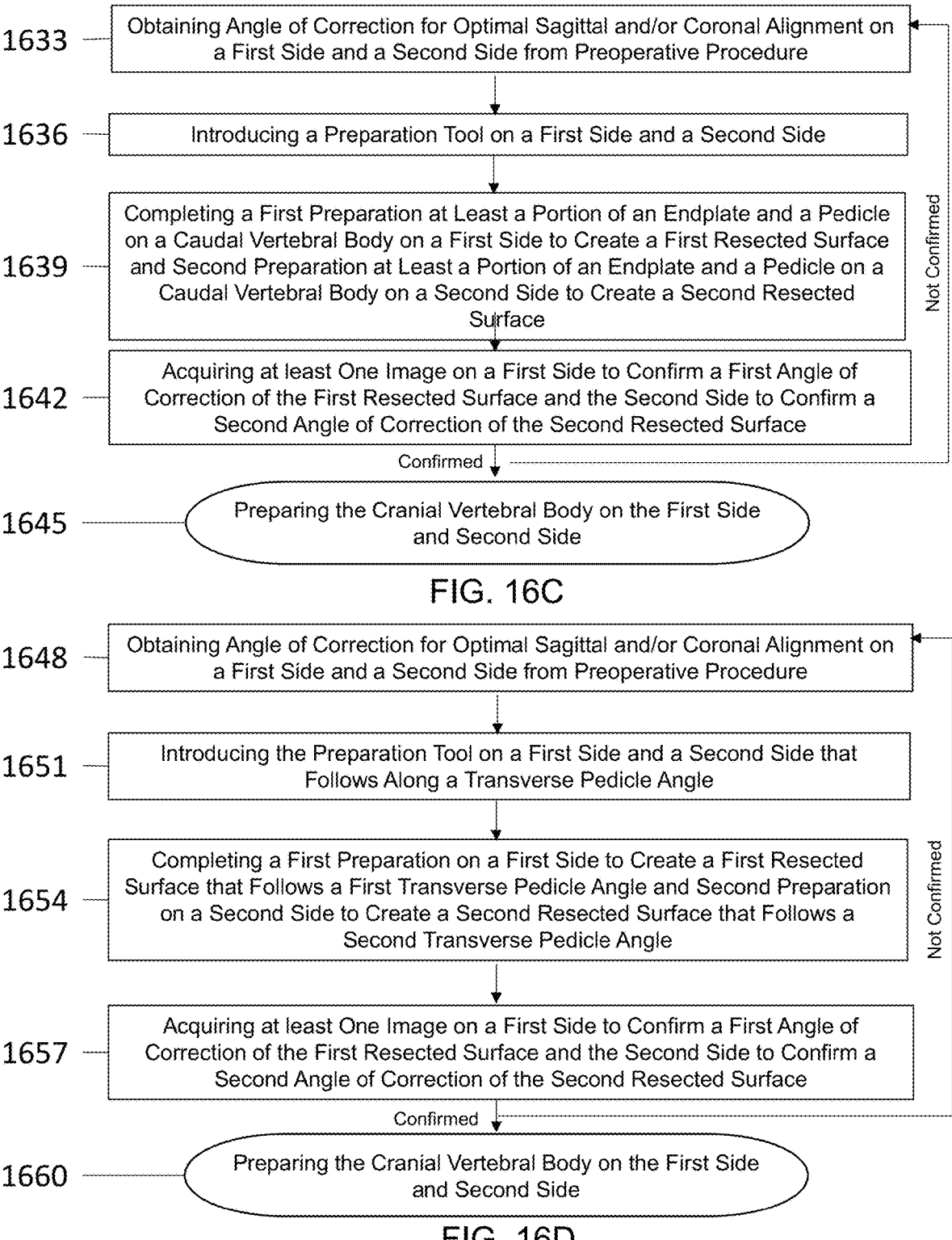

PREPARING THE CAUDAL VERTEBRAL BODY

1633 — Obtaining Angle of Correction for Optimal Sagittal and/or Coronal Alignment on a First Side and a Second Side from Preoperative Procedure 1636 — Introducing a Preparation Tool on a First Side and a Second Side 1639 — Completing a First Preparation at Least a Portion of an Endplate and a Pedicle on a Caudal Vertebral Body on a First Side to Create a First Resected Surface and Second Preparation at Least a Portion of an Endplate and a Pedicle on a Caudal Vertebral Body on a Second Side to Create a Second Resected Surface 1642 — Acquiring at least One Image on a First Side to Confirm a First Angle of Correction of the First Resected Surface and the Second Side to Confirm a Second Angle of Correction of the Second Resected Surface Not Confirmed Confirmed 1645 — Preparing the Cranial Vertebral Body on the First Side and Second Side

FIG. 16C

1648 — Obtaining Angle of Correction for Optimal Sagittal and/or Coronal Alignment on a First Side and a Second Side from Preoperative Procedure 1651 — Introducing the Preparation Tool on a First Side and a Second Side that Follows Along a Transverse Pedicle Angle 1654 — Completing a First Preparation on a First Side to Create a First Resected Surface that Follows a First Transverse Pedicle Angle and Second Preparation on a Second Side to Create a Second Resected Surface that Follows a Second Transverse Pedicle Angle 1657 — Acquiring at least One Image on a First Side to Confirm a First Angle of Correction of the First Resected Surface and the Second Side to Confirm a Second Angle of Correction of the Second Resected Surface Not Confirmed Confirmed 1660 — Preparing the Cranial Vertebral Body on the First Side and Second Side

FIG. 16D

PREPARING THE CAUDAL VERTEBRAL BODY

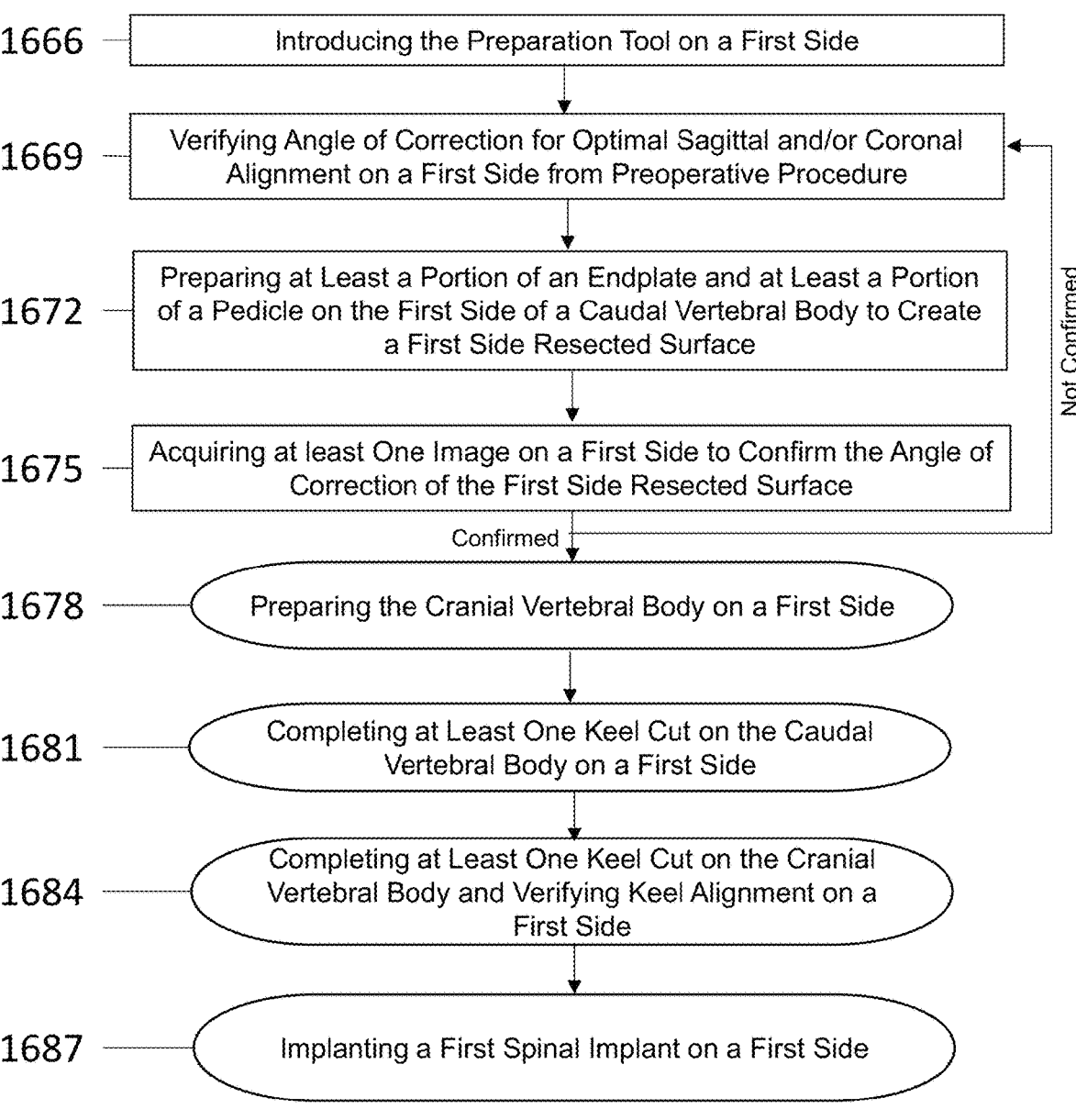

1666 — Introducing the Preparation Tool on a First Side

1669 — Verifying Angle of Correction for Optimal Sagittal and/or Coronal Alignment on a First Side from Preoperative Procedure 1672 — Preparing at Least a Portion of an Endplate and at Least a Portion of a Pedicle on the First Side of a Caudal Vertebral Body to Create a First Side Resected Surface 1675 — Acquiring at least One Image on a First Side to Confirm the Angle of Correction of the First Side Resected Surface Not Confirmed Confirmed 1678 — Preparing the Cranial Vertebral Body on a First Side 1681 — Completing at Least One Keel Cut on the Caudal Vertebral Body on a First Side 1684 — Completing at Least One Keel Cut on the Cranial Vertebral Body and Verifying Keel Alignment on a First Side 1687 — Implanting a First Spinal Implant on a First Side

AOC

1720

1720

PREPARING THE CRANIAL VERTEBRAL BODY

PREPARING THE CRANIAL VERTEBRAL BODY

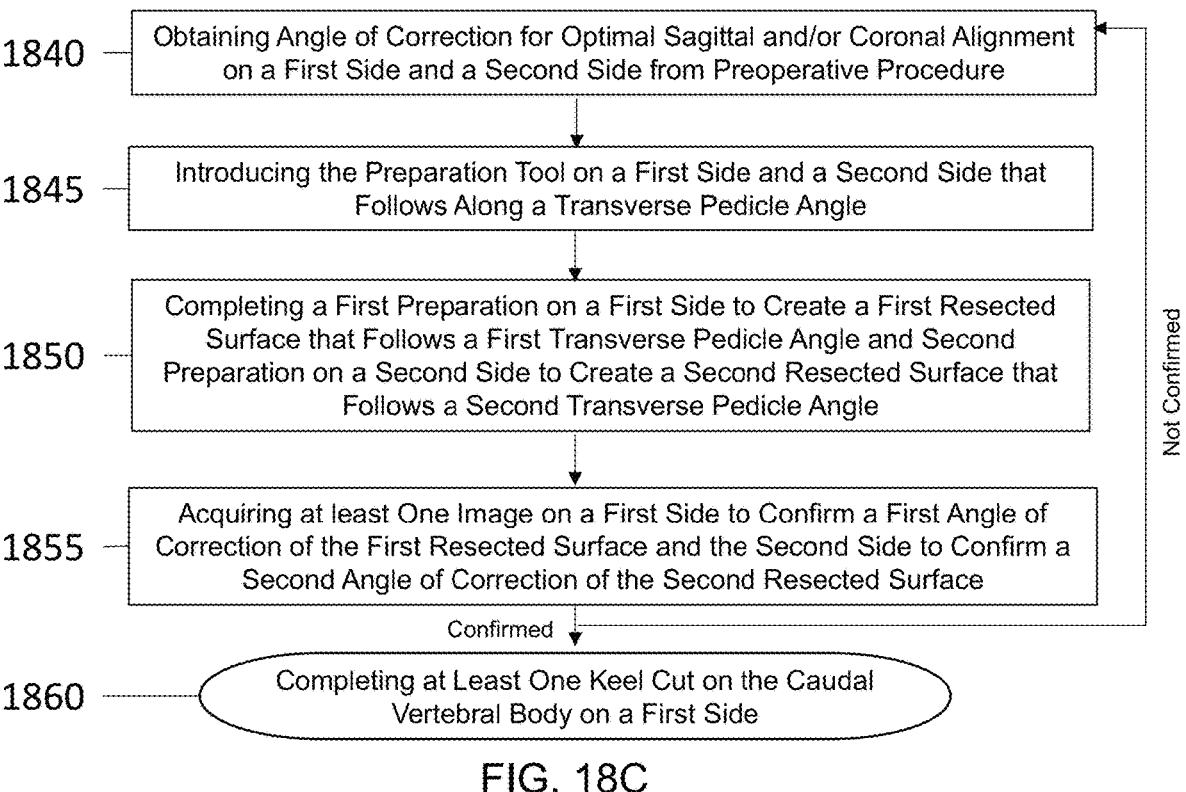

1840 — Obtaining Angle of Correction for Optimal Sagittal and/or Coronal Alignment on a First Side and a Second Side from Preoperative Procedure 1845 — Introducing the Preparation Tool on a First Side and a Second Side that Follows Along a Transverse Pedicle Angle 1850 — Completing a First Preparation on a First Side to Create a First Resected Surface that Follows a First Transverse Pedicle Angle and Second Preparation on a Second Side to Create a Second Resected Surface that Follows a Second Transverse Pedicle Angle 1855 — Acquiring at least One Image on a First Side to Confirm a First Angle of Correction of the First Resected Surface and the Second Side to Confirm a Second Angle of Correction of the Second Resected Surface Not Confirmed Confirmed 1860 — Completing at Least One Keel Cut on the Caudal Vertebral Body on a First Side

FIG. 18C

PREPARING THE CRANIAL VERTEBRAL BODY 1910
1930
1920
1900

1950
1940

1970 1960

COMPLETING AT LEAST ONE KEEL CHANNEL
ON THE CAUDAL VERTEBRAL BODY

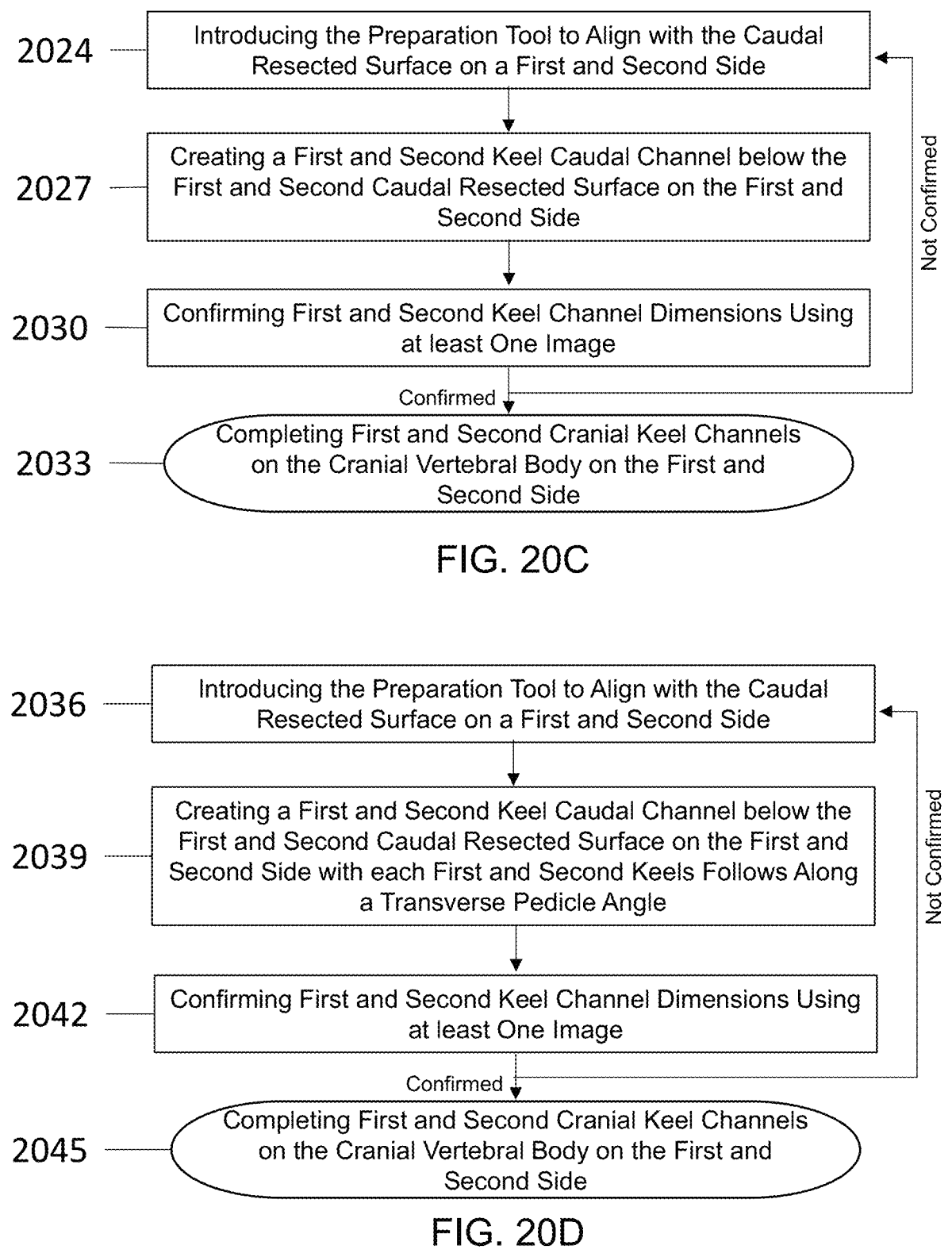

2024 —— Introducing the Preparation Tool to Align with the Caudal Resected Surface on a First and Second Side 2027 —— Creating a First and Second Keel Caudal Channel below the First and Second Caudal Resected Surface on the First and Second Side 2030 —— Confirming First and Second Keel Channel Dimensions Using at least One Image Not Confirmed Confirmed 2033 —— Completing First and Second Cranial Keel Channels on the Cranial Vertebral Body on the First and Second Side

FIG. 20C

2036 —— Introducing the Preparation Tool to Align with the Caudal Resected Surface on a First and Second Side 2039 —— Creating a First and Second Keel Caudal Channel below the First and Second Caudal Resected Surface on the First and Second Side with each First and Second Keels Follows Along a Transverse Pedicle Angle 2042 —— Confirming First and Second Keel Channel Dimensions Using at least One Image Not Confirmed Confirmed 2045 —— Completing First and Second Cranial Keel Channels on the Cranial Vertebral Body on the First and Second Side

FIG. 20D

COMPLETING AT LEAST ONE KEEL CHANNEL ON THE
CAUDAL VERTEBRAL BODY

COMPLETING AT LEAST ONE KEEL CHANNEL
ON THE CRANIAL VERTEBRAL BODY

COMPLETING AT LEAST ONE KEEL CHANNEL ON THE CRANIAL VERTEBRAL BODY

COMPLETING AT LEAST ONE KEEL CHANNEL ON THE
CRANIAL VERTEBRAL BODY

2220

2200

2210

2230

2200

2230

2410          2400

24C

24E

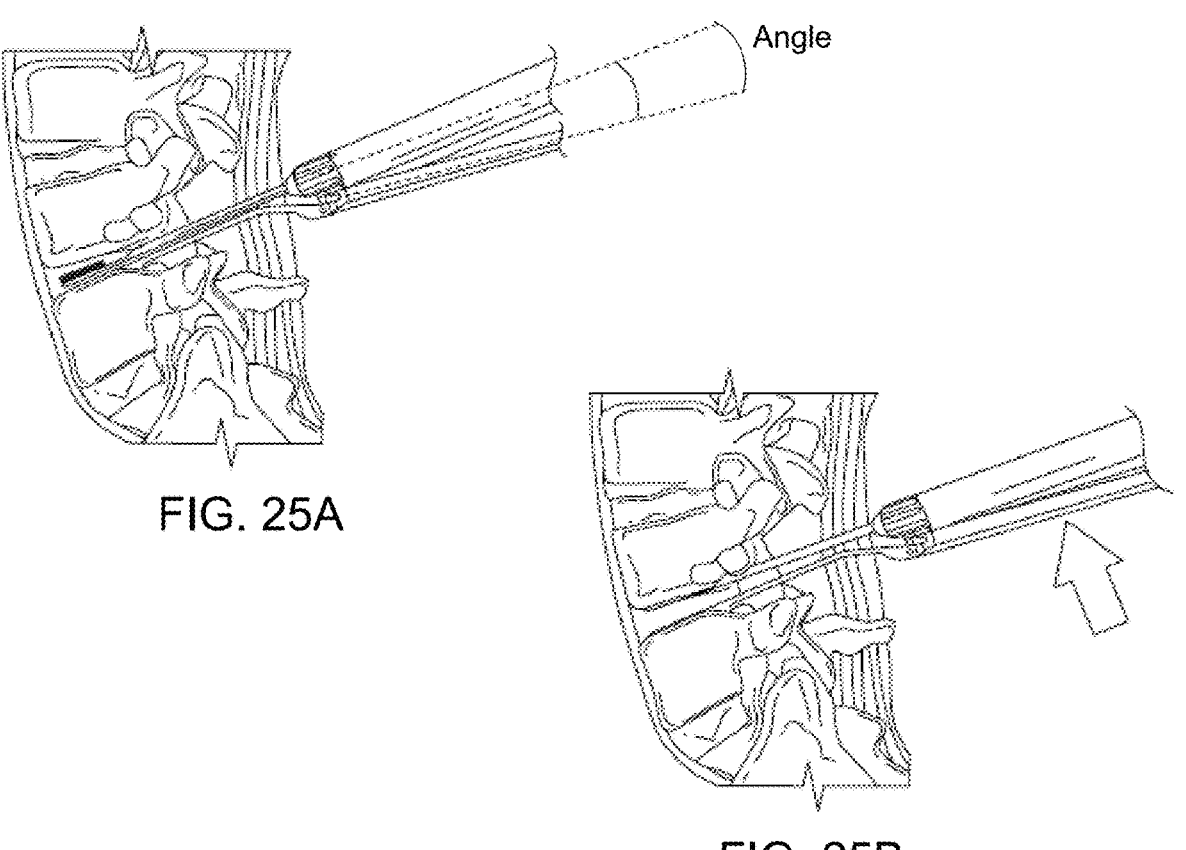
Angle
FIG. 25A
FIG. 25B
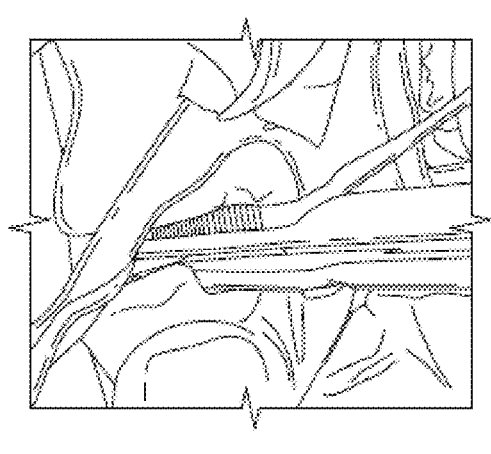
FIG. 25C
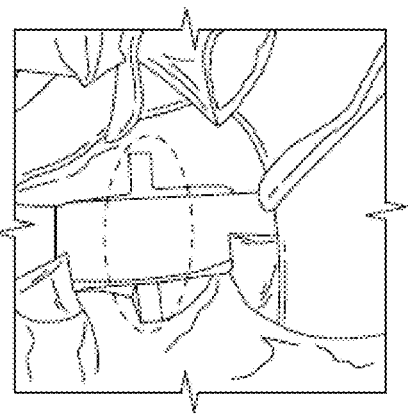
FIG. 25D

IMPLANTING A SPINAL IMPLANT ON THE AT LEAST ONE SIDE

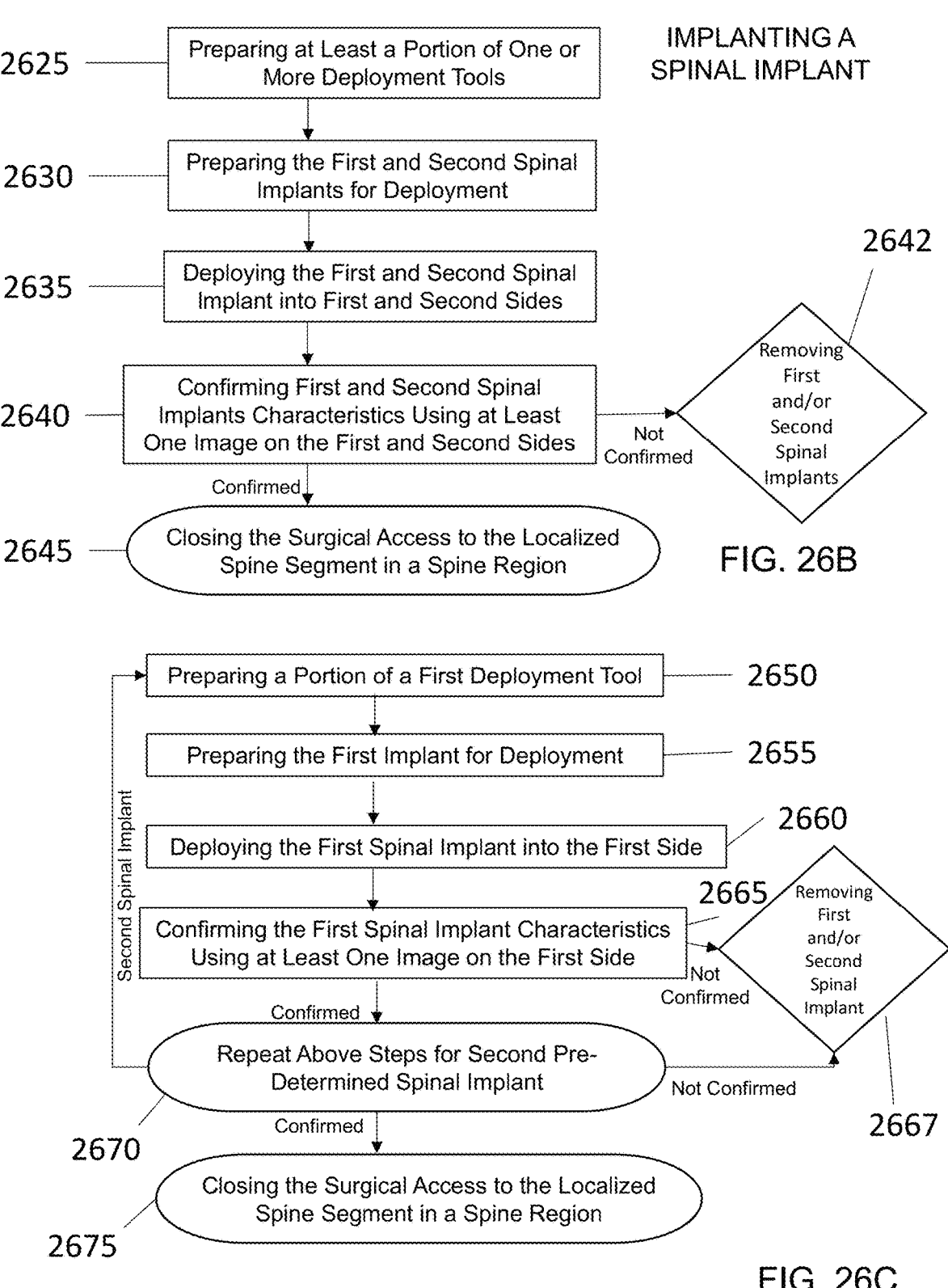

2625 — Preparing at Least a Portion of One or More Deployment Tools

IMPLANTING A SPINAL IMPLANT

2630 — Preparing the First and Second Spinal Implants for Deployment

2635 — Deploying the First and Second Spinal Implant into First and Second Sides

2642

2640 — Confirming First and Second Spinal Implants Characteristics Using at Least One Image on the First and Second Sides Not Confirmed → Removing First and/or Second Spinal Implants Confirmed 2645 — Closing the Surgical Access to the Localized Spine Segment in a Spine Region

FIG. 26B

Preparing a Portion of a First Deployment Tool — 2650

Preparing the First Implant for Deployment — 2655

Deploying the First Spinal Implant into the First Side — 2660

Second Spinal Implant

Confirming the First Spinal Implant Characteristics Using at Least One Image on the First Side 2665 → Removing First and/or Second Spinal Implant Not Confirmed Confirmed Repeat Above Steps for Second Pre-Determined Spinal Implant

2670

Not Confirmed

2667

Confirmed

2675 — Closing the Surgical Access to the Localized Spine Segment in a Spine Region

FIG. 26C

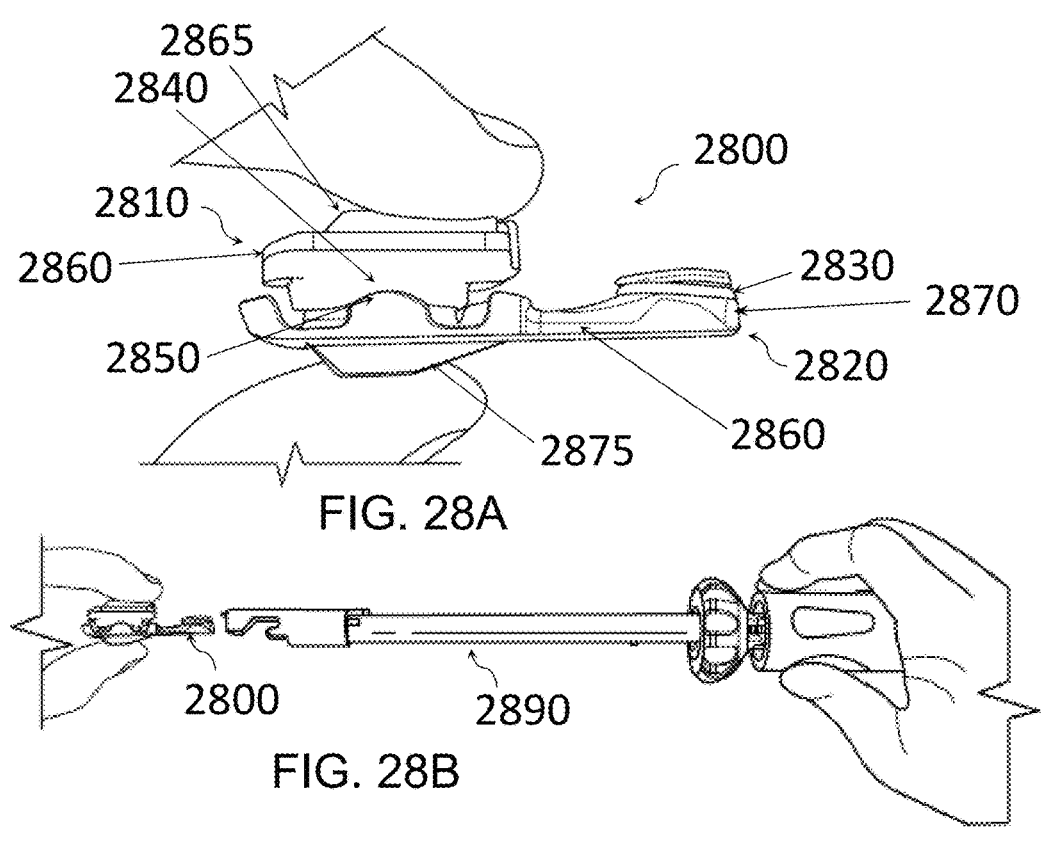
FIG. 28A
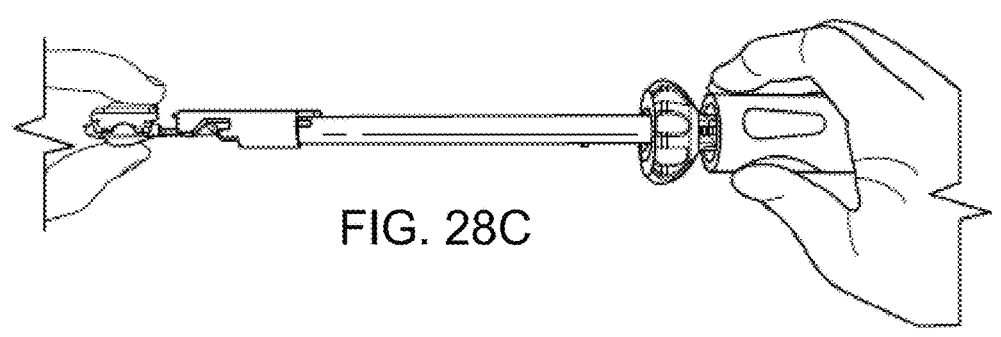
FIG. 28B
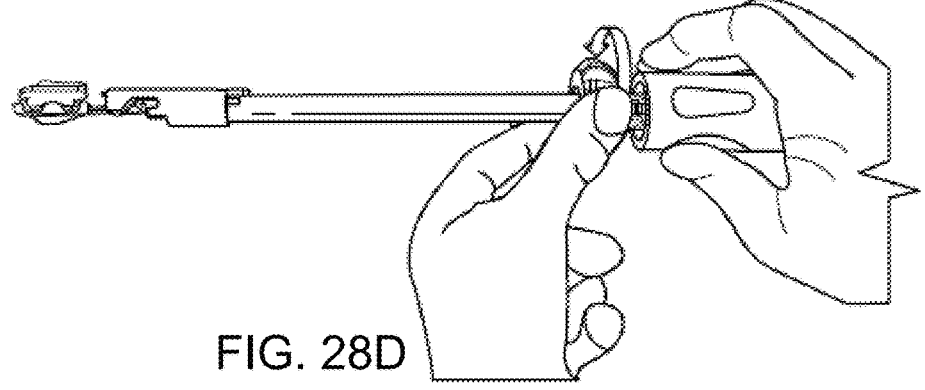
FIG. 28C
FIG. 28D 2800    2890    FIG. 29A 2920    2910    2900    FIG. 29B 2905    2907

2909

REMOVING AT LEAST ONE SPINAL IMPLANT

3300
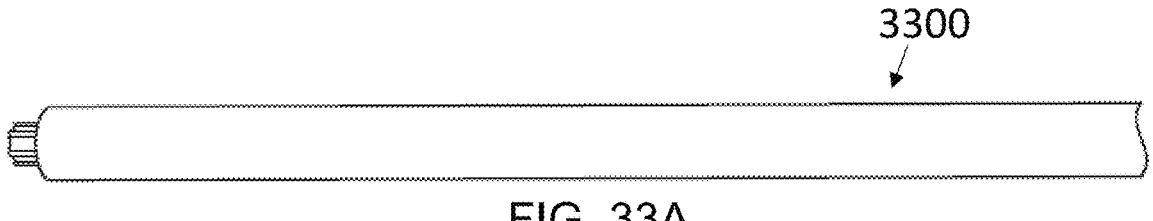
FIG. 33A
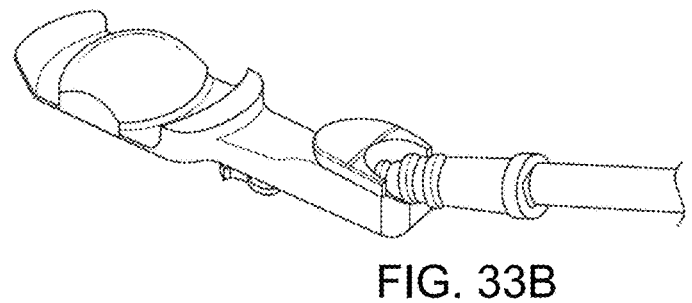
FIG. 33B
3400
3420
3410
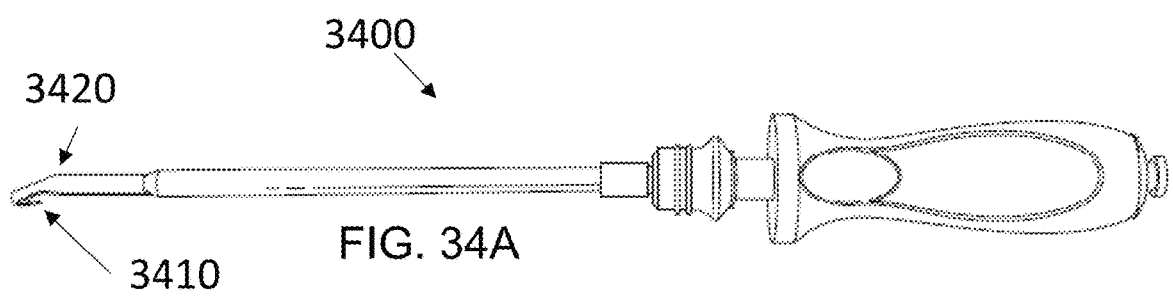
FIG. 34A
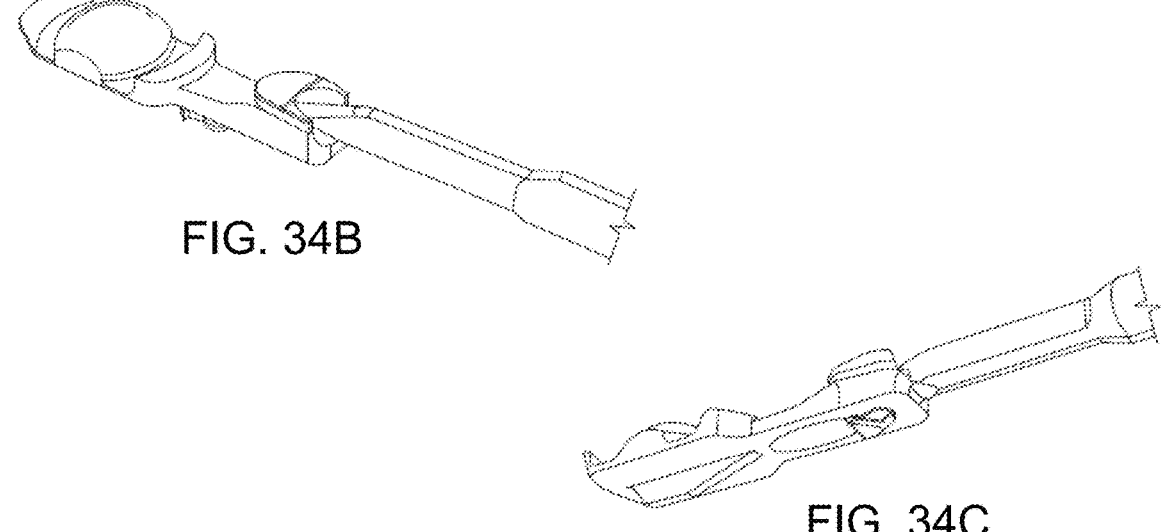
FIG. 34B
FIG. 34C

| Numerical Measurement | Purpose and/or Definition |
|---|---|
| Pelvic Incidence (PI) | Characterization of portion of lumbar lordosis in the lower spine. It is the angle between the superior sacral endplate and a horizontal reference line. Sacral slope determines the position of lumbar spine, since the sacral plateau forms the base of the spine. |
| Pelvic Tilt (PT) | Measure of how the pelvis moves relative to femoral head. It is the angle between the line connecting the midpoint of the superior sacral plate to the center axis of the femoral heads and a vertical reference line. It denotes the spatial orientation of the pelvis. |
| Sacral Slope (SS) | Measure of how the sacrum moves. It is the angle between the superior sacral endplate and a horizontal reference line. Sacral slope determines the position of lumbar spine, since the sacral plateau forms the base of the spine. |
| L1 Pelvic Angle (L1PA) | Measure of lumbar lordosis and pelvic movement |
| Sagittal Vertical Axis (SVA) | Measure of the horizontal distance between the postero-superior corner of the sacrum and the C7 plumb line. |
| Instantaneous Center of Rotation (ICOR) | Measure of how the longitudinal axis of the vertebra passes through part of the vertebral body in order to restore proper load distribution. |
| Lumbar Lordosis (LL) | Measure of the angle between the upper plate of the first lumbar and first sacral vertebral bodies. |
| Segmental Lordosis | Measure of lordosis of each spine segment |
| Regional Lordosis | Measure of L1-S1 lordosis |
| Wedge Angle, Vertebral Body | Characterization of bony anatomy |
| Wedge Angle, Disc | Characterization of disc anatomy |
| Osteotomy Sagittal Angle | Measurement of the sagittal trajectory for a wedge osteotomy. It is the wedge angle derived from understanding how much wedge angle has been lost from the aging of the disc and to restore sagittal balance. |
| Osteotomy Transverse Trajectory | Planning for osteotomy to match or substantially match the transverse pedicle angle, which is the angle of the longitudinal or transverse axis of the pedicle. |
| Osteotomy Coronal Trajectory | Measurement of the medial or lateral coronal trajectory of the osteotomy. |
| Convergence Angle or Transverse Pedicle Angle | Measure of the angle of the longitudinal or transverse axis of the pedicle. |
| A/P Distance | Measure of how one or more implants are positioned between the anterior and posterior border of a vertebral body. It is the distance of the anterior end of one or more implants relative the anterior end of a vertebral body. |
| Neutral Alignment | Measure of angled position of one or more deployed spinal implants between a prepared intervertebral space. The measurement of angle of the spinal implant relative to the inferior and superior vertebral body. |
| Implant & Trial Tools Sizes | The implant and/or trial tool width, length and height may be approximated within the prepared intervertebral disc space. |

FIG. 35

Cobb's method                    Anterior Tangent method

Index:

P-posterior height
A-anterior height
L-vertebral length
Y-difference between P and A

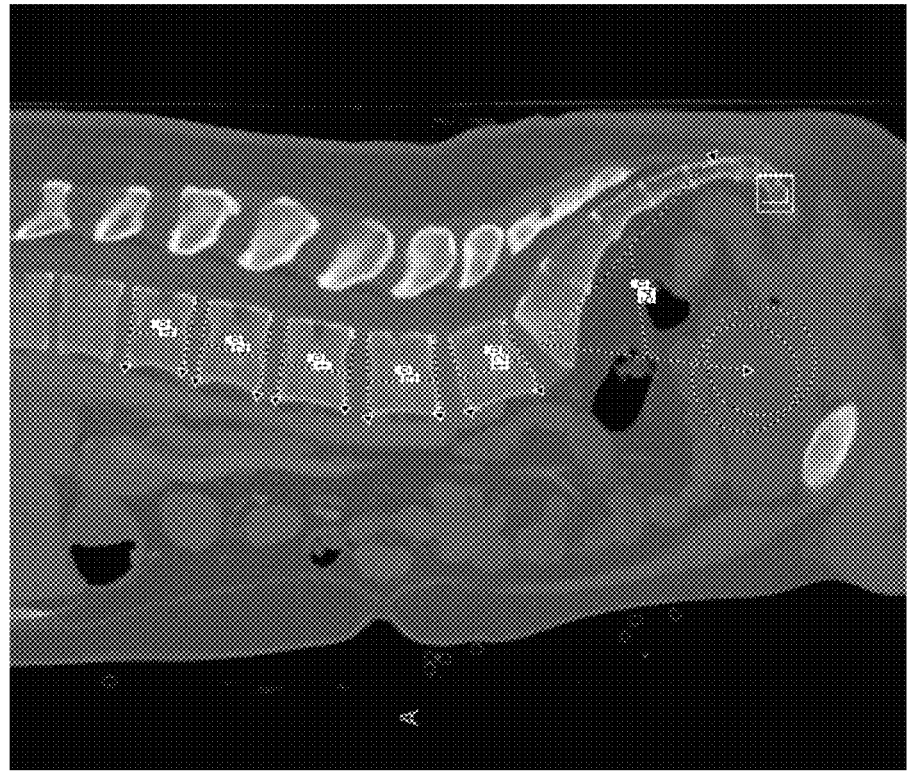
FIG. 36L

METHODS FOR RESTORING BILATERAL SPINAL ALIGNMENT AND/OR RANGE OF MOTION

CROSS-REFERENCE TO RELATED APPLICATIONS

This application is a continuation of PCT Application No. PCT/US23/23600 entitled "Total Spinal Joint Replacement Methods & Instrumentation," filed May 25, 2023, which claims the benefit of U.S. Provisional Application No. 63/345,560 entitled "Total Spinal Joint Replacement Methods & Instrumentation," filed May 25, 2022, U.S. Provisional Application No. 63/375,379 entitled "Surgical Instrumentation for Total Spinal Joint Replacement," filed Sep. 12, 2022, U.S. Provisional Application No. 63/445,954 entitled "Fusion Spinal Implant Systems," filed Feb. 15, 2023, and U.S. Provisional Application No. 63/351,568 entitled "Robotic & Navigation Assisted Total Spinal Joint Methods," filed Jun. 13, 2022, the disclosures of which are incorporated by reference herein in their entireties This application further claims the benefit of and priority to Patent Cooperation Treaty Application No. PCT/US22/74635, entitled "Robotic & Navigation Assisted Total Spinal Joint Methods," filed Aug. 5, 2022, the disclosure of which is incorporated by reference herein in its entirety.

TECHNICAL FIELD

The disclosure relates to the field of medical devices for restoration of spinal alignment and maximize range of motion for patients who suffer from spinal degenerative disorders. More specifically, the disclosure further relates to instruments that are configurable for use with a patient in a surgical environment and a method for restoring spinal alignment and range of motion.

BACKGROUND OF THE INVENTION

Spinal pathologies and disorders such as degenerative disc disease, disc herniation, osteoporosis, spondylolisthesis, stenosis, scoliosis and other curvature abnormalities, kyphosis, tumor, and/or fractures may result from a wife variety of factors, including (but not limited to) trauma, disease and/or degenerative conditions often exacerbated by injury and aging. Spinal disorders typically result in symptoms including deformity, pain, nerve damage, and partial or complete loss of mobility that may be treated with surgical and non-surgical options.

Non-surgical treatments, such as medication, rehabilitation and exercise can be effective, however, many of these treatments ultimately fail to relieve the symptoms associated with these disorders. Surgical options for these spinal disorders may entail methods, devices and techniques for implanting prosthetics that seek to restore the mechanical support function of vertebrae, but such devices are often unsuccessful in restoring alignment and/or range of motion to the patient's anatomy. Thus, improvements in surgical procedures for addressing spinal injuries and/or pathologies is needed, including devices, methods and techniques for restoring alignment and/or range of motion to a patient's spine.

BRIEF DESCRIPTION OF THE SEVERAL VIEWS OF THE DRAWINGS

FIG. 1 graphically illustrates one embodiment of a preoperative method for a total joint replacement spinal implant system;

FIG. 2A graphically illustrates one embodiment of an imaging protocol of FIG. 1;

FIG. 2B depicts one embodiment of different static and/or dynamic patient positions for the imaging protocol;

FIGS. 3A-3B graphically illustrates different embodiments of an intraoperative method for a total joint spinal implant system;

FIGS. 6A-6B graphically illustrates different embodiments for one or more decompression techniques for the total joint replacement spinal implant system;

FIGS. 7A-7B graphically illustrates one embodiment for a method of selecting the proper spinal implant size;

FIGS. 8A-8D graphically illustrates different embodiments of a method of determining the proper spinal implant length using length trials;

FIGS. 12A-12D graphically illustrates different embodiments of a method of determining the proper spinal implant height using height trials;

FIGS. 13A-13C depict different views of one embodiment of a height trial;

FIG. 14 depict a sagittal view of the height trial within an intravertebral space within a spine region;

FIGS. 15A-15C graphically illustrates different embodiments of a method of preparing an intravertebral space within a localized spine segment for alignment restoration;

FIGS. 16A-16E graphically illustrates different embodiments of a method of preparing the caudal vertebral body;

FIGS. 18A-18D graphically illustrates different embodiments of a method of preparing the cranial vertebral body;

FIGS. 20A-20E graphically illustrates different embodiments of a method of completing at least one keel cut on the caudal vertebral body;

FIGS. 25A-25D depicts sagittal views and magnified views of the keel alignment tool within the prepared intravertebral space to create at least one cranial keel channel;

FIGS. 26A-26C graphically illustrates different embodiments of a method of implanting a total joint replacement spinal implant;

FIGS. 28A-28D depicts different views of preparing a spinal implant for deployment;

FIGS. 29A-29E depicts cross-sectional and magnified views of FIGS. 28A-28D of preparing a spinal implant for deployment;

FIGS. 33A-33B depicts a side view of one embodiment of a removal tool and its insertion location on the spinal implant;

FIGS. 34A-34C depicts a side and isometric view of one embodiment of spinal implant removal tool and its insertion location on the spinal implant;

FIG. 35 displays a table of the different selected surgical measurements (SSMs)

DETAILED DESCRIPTION OF THE INVENTION

Figure 3B:
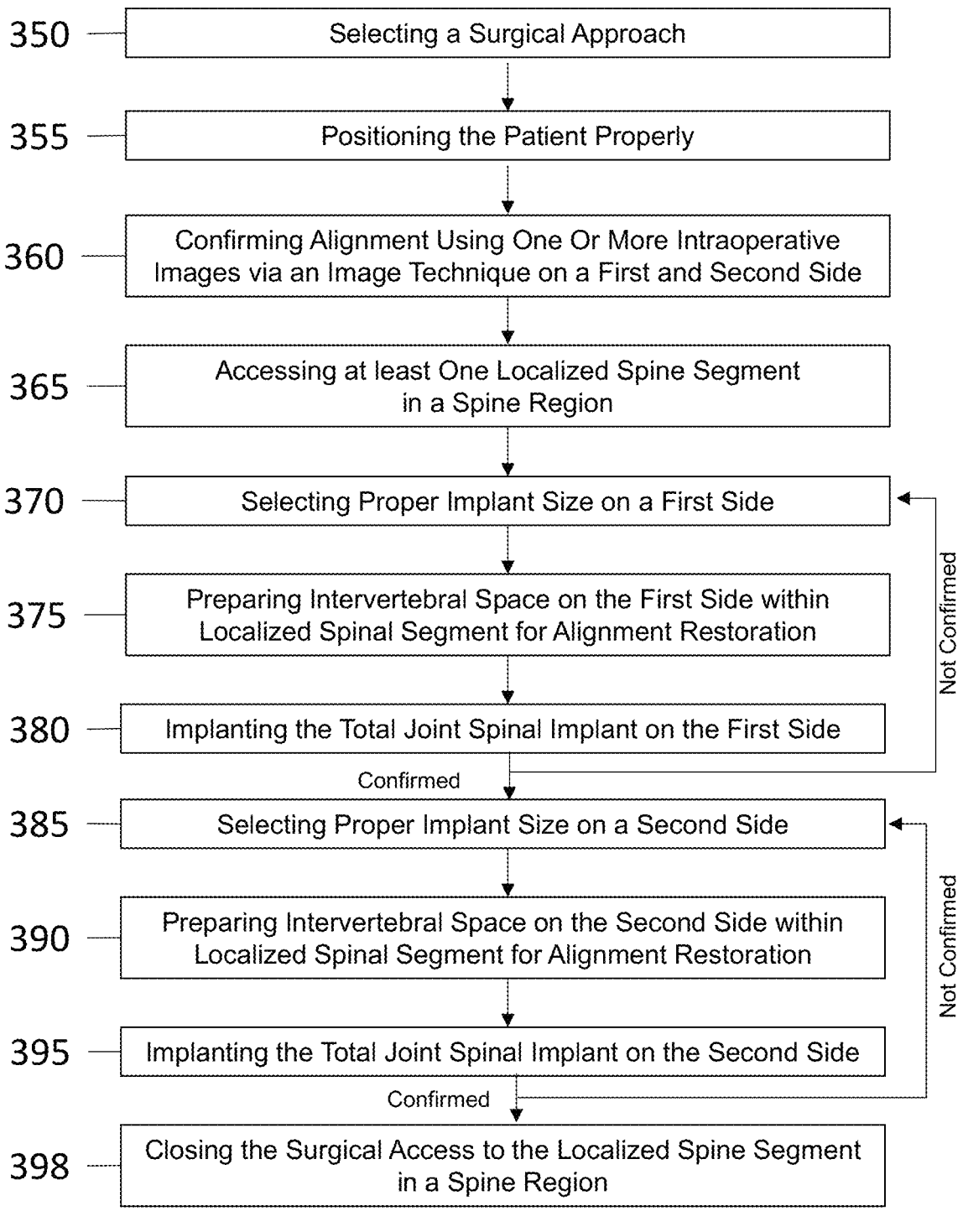

Over the past few decades, remarkable advancements in the understanding of spinal disorders have been achieved. While spinal fusion (or arthrodesis of one of more spinal levels) is currently considered a "gold standard" for surgical correction of a spinal disorder, spinal fusion typically "freezes" the degenerated spinal joint, which does not restore mobility or range of motion to the affected level(s) and rarely addresses any malalignment of the spine. Moreover, spinal fusion has been associated with an accelerated degeneration of adjacent spinal levels.

In contrast to spinal fusion, spinal disc and/or facet joint replacement devices have been more recently developed which strive to repair and/or replace damaged and/or degenerated spinal anatomy, but concurrently seek to avoid fusion, arthrodesis and/or immobilization of a treated spinal segment. Unfortunately, many of these systems are contraindicated for or cannot address and/or repair highly damaged, degenerated and/or misaligned anatomy, and even when successfully implanted these systems can often result in abnormal spinal kinematics and/or hypermobility of the treated spinal levels—which may result increased pain and patient discomfort, abnormal gait, damage to the treated anatomy, implant migration and/or failure and/or accelerated degeneration of adjacent spinal levels. Moreover, spinal disc and/or facet joint replacement devices are often unable to correct malalignment of an individual spinal level and/or the entire spine.

At least a portion of the present invention includes the realization of a need in the art for systems, devices and/or methods for treated degenerated and/or diseased spinal anatomy which provides for restoration of spinal alignment towards a more normal kinematic movement, which may include restoration and/or partial restoration of the normal motion patterns of an individual spinal level as well as those of an entire spine or spinal segment. In some situations, it may be desirous to restore a natural alignment and/or motion pattern between two diseased and/or degenerated adjacent vertebrae, while in other situations it may be more desirous to alter the alignment and/or motion patterns between two diseased and/or degenerated adjacent vertebrae in some manner to achieve a more desirable overall alignment and/or motion pattern of an entire spine or motion segments thereof, which may include altering an treated spinal level to a condition further away from a natural alignment and/or motion pattern (which may compensate for malignment of the spinal at other motion segments, for example).

Another significant feature of the disclosed invention includes the realization that the surgical alteration of degenerated and/or diseased spinal anatomy to a more normal kinematic movement before and/or during implantation of a surgical device can significantly improve implant performance and/or durability, as well as clinical outcomes and patient satisfaction. Accordingly, various embodiments encompass spinal implants that are designed to provide various levels of stabilization of a treated spinal motion segment and/or segments while concurrently restoring spinal alignment, desirably restoring and/or controlling mobility within one or more spinal segments in a spine region. Such stabilization and restoration of normal kinematics can dramatically improve surgical outcomes for both motion and/or fusion implant components, as the restoration of balance and kinematics to the spine or various portions thereof may dramatically reduce loading and/or stresses experienced by the implant components, thereby reducing wear and/or implant migration in many cases.

One exemplary method of restoring alignment and mobility of a spinal segment within a spinal region can comprise the steps of: collecting anatomical data of a patient and completing a preoperative protocol and/or a preoperative method and then performing an intraoperative method of treating the patient. In another exemplary embodiment, the method of restoring alignment and mobility of a spinal segment within a spinal region may further comprise the steps of removing at least one deployed spinal implant. In another embodiment, a method of restoring alignment and mobility of a spinal segment within a spinal region can comprise the steps of completing the intraoperative method. In still another embodiment, a method of restoring alignment and treating a spinal segment within a spinal region can comprise the steps of completing various steps of the intraoperative methods in conjunction with the implantation of one of more spinal fusion devices.

Preoperative Protocol or Preoperative Method

In one exemplary embodiment, a method for restoring alignment and/or motion to a targeted spinal motion segment (and/or to provide arthrodesis and/or fusion to one or more locations of the spine) can comprise the steps of collecting preoperative data (e.g., two-dimensional and/or three-dimensional data) regarding the anatomy of a patient during a preoperative protocol and/or a pre-operative method, and then analyzing this data in various ways to create a surgical plan for intraoperative repair of the patient's anatomy. The ultimate goals of such a preoperative protocol can be to analyze, estimate and/or predict motion of the patient's spine and/or spinal motion segment(s) and to plan a surgical correction which alters various aspects of the spinal motion and/or alignment to desirably restore more normal kinematics to some or all of the patient's spine and/or targeted spinal motion segments thereof, with an objective of improving patient outcomes and/or reducing the occurrence of intra-operative/postoperative morbidity or mortality, as well as reduce the overall risk to the patient. More specifically, the detailed goals of the preoperative procedure can include the documentation of the condition(s) for which surgery is required; assessing the patient's overall health status to uncover hidden conditions that could increase perioperative and postoperative risk; collection and analysis of anatomical data, development of an appropriate surgical or intraopera-tive plan; education of the patient about the upcoming surgery to reduce anxiety; and/or reduce costs by shortening hospital stay and increasing patient satisfaction.

With reference to FIG. 1, one exemplary preoperative protocol can comprise the steps of: completing a drug history and a drug management protocol 10; conducting a health behavior assessment and health behavior protocol 20; assessing perioperative anesthesia risk and completing peri-operative anesthesia protocol for Enhanced Recovery After Surgery (ERAS) 30; and completing an imaging protocol 40. Various additional steps of the preoperative protocol may further including modeling and/or creating a virtual model of patient anatomy utilizing images and/or other data acquired during the protocol and/or developing a preopera-tive and/or perioperative surgical plan and/or surgical approach for the anatomical repair.

In various embodiments, the step of completing a drug history and a drug management protocol may optionally include the patient revealing all allergies, all information on prescription medications, over-the-counter medications, "as-needed" medications, vitamins, supplements, and/or herbal medications. Such documented information is essential to ensure positive surgical outcomes and prevent complica-tions. The drug management protocol may include the cessation or modification of medications prior to surgery to ensure that the patient can safely undergo anesthesia and the surgery itself. In one embodiment, the drug management protocol includes the cessation of opioids prior to surgery. More specifically, cessation should include 2 weeks to three months prior to surgery to reduce the risk of postoperative complications. Other medications, such as steroids, NSAIDs, supplements, epidural injections and/or any other medication that may contribute to poor post operative out-comes. In one embodiment, the preoperative protocol com-prises the step of conducting a health behavior assessment and completing a health behavior protocol. The health behavior protocol includes an evaluation of the patient's health via a thorough medical history and examination; administration of health questionnaires; evaluation of the patient's behavioral observations to questionnaire(s) (e.g., patient's response to health questions, outlook, patient's coping strategies, expectations, motivation and adherence to medical treatments). The health behavior protocol may include counseling and cessation of particular medications to improve surgical outcomes. In one embodiment, a patient should cease smoking and the utilization of tobacco or nicotine products of any kind, including vaping, at least 6 weeks before surgery and should not be continued until 6 months after surgery.

In various embodiments, anatomical data regarding the alignment and motion of the patient spinal anatomy and/or related structures can be collected and analyzed. With ref-erence to FIGS. 2A-2B, one exemplary preoperative proto-col comprises an imaging protocol. Preoperative imaging can be an essential tool for providing a current picture and understanding of a patient's condition and morphological bony structures. Acquiring one or more images provides surgeons with more information and the surgeons can exploit the anatomical and functional data to help develop an intraoperative or surgical approach to restore alignment and/or restore mobility.

As disclosed, an exemplary imaging protocol can com-prises the steps of: completing at least one MRI imaging scan to evaluate various soft-tissue related pathology, including disc degeneration grade, facet joint cartilage, and nerve compression; obtaining at least one or more radio-graphs (e.g., X-rays) at different static and dynamic posi-tions, such positions including at least a standing anterior/posterior, flexion/extension, a lateral neutral, a lateral slump sitting views to evaluate biomechanics and/or any combi-nation thereof. The imaging protocol may further include the step of obtaining at least one CT scan or other imaging modalities.

The imaging protocol may be desirably used to review, analyze and/or understand a patient's bone morphology and spinal biomechanics. The spinal biomechanics may be evaluated during the lordotic changes between standing neutral and lateral sitting, which may be indicative of guarding behaviors, spinal rigidity and/or flexibility and pathology of the patient anatomy. The lateral sitting view may also be used to evaluate degree of spondylolisthesis and angulatory changes due to the translational force of this position. Furthermore, the bone morphology may evaluate the facet joints, spondylolisthesis, shape of the endplate and Schmorl's nodes. If necessary, the amount of spondylolis-thesis should be measured, and it should be obtained or measured down the midline.

In another exemplary embodiment, an imaging protocol may comprise the steps of acquiring at least one image using a first imaging technique 210; acquiring at least one image using a second imaging technique 220; and/or optionally acquiring at least one image using a third imaging technique 230. Each of the first imaging technique, the second imaging technique and/or the third imaging technique may comprise different imaging technique, including 2-D/3-D imaging techniques, as well as 4-D (e.g., time dependent and/or "live motion") imaging techniques. Each of the first imaging techniques, the second imaging techniques and/or the third imaging technique may comprise a same or a different imaging technique. The imaging techniques include an MRI, a radiograph, a CT scan, an ultrasound, and/or any combi-nations thereof. Each of the first imaging techniques, the second imaging technique and/or the third imaging tech-nique may comprise a single image and/or multiple images. Each of the first imaging technique, the second imaging technique and/or the third imaging technique may comprise static and/or dynamic positions.

In one embodiment, acquiring at least one image using a CT scan technique may desirably help a surgeon to identify and/or analyze a damaged soft tissue such as an interverte-bral disc(s) or other tissue injuries, as well as identify other sources of pain. Furthermore, a CT scan be particularly useful in identifying the presence of canal or foraminal stenosis and/or ligament hypertrophy.

In some embodiments, acquiring at least one image using radiographs (e.g., X-rays) may desirably help the surgeon to investigate the cause of the patients' symptoms at a targeted spinal level, bone morphology, and/or identify presence of abnormal movement. The at least one image may comprise static images, full spine images, dynamic images, and/or any combinations thereof.

In one embodiment, the at least one radiograph image may comprise at least one static image. The at least one static image may comprise a posterior-anterior and a lateral image of the whole of the spine and pelvis under load. When acquiring the at least one static image, the patient's arms may be positioned adjacent to the patient's body, and desirably not be held out in front nor the hands placed behind the head. various imaging techniques seek to eliminate a non-discogenic etiology wholly or partly responsible for the patient's symptoms (non-degenerative lumbar causes: fractures, infection, neoplasia or extra-spinal causes) and to investigate the level concerned (disc degeneration, spondylolisthesis, joint abnormality, etc.). The at least one static images may also provide useful information for preparing the surgical procedure, including the quality of the bone, the shape of the vertebral endplates, the orientation of the intervertebral spaces relative to the pubis to help antici-pate surgical approach difficulties, on whether the disc is collapsed, identification of bony for aminal stenosis (which cannot be treated via the anterior route in isolation); on the state of adjacent discs and the lumbopelvic-femoral com-plex, and/or any combination thereof.

In one embodiment, the at least one radiograph image may comprise at least one dynamic image. The at least one dynamic image may comprise a lateral flexion, contralateral flexion, extension, flexion while sitting and/or standing. Use of data from the at least one dynamic image may assist the surgeon to assess the mobility of the healthy discs and the presumed pathological disc (as decreased, normal or exag-gerated mobility suggests intervertebral mechanical insta-bility). The aim of dynamic images can be to identify abnormal movement between two vertebrae.

In one embodiment, the at least one radiograph image may comprise at least one full spine image. The at least on full spine image includes a full spine PA and/or a lateral static radiograph. The at least one full spine image helps the surgeon to assess the sagittal balance (e.g., lordosis), and/or scoliosis.

In one embodiment, acquiring at least one image using magnetic resonance imaging (MRI) may desirably help a surgeon to assess chronic low back pain by highlighting the disc and/or abnormal vertebral endplates. Such images may provide evidence for the pain being discogenic. It also provides information on the dimensions of the spinal canal and the appearance of the articular facets.

In another embodiment, acquiring of one or more images using at least one imaging technique will comprise a obtain-ing an approximated coronal and/or sagittal vertical axis (SVA) alignment and mobility goals. The approximated coronal and/or sagittal alignment goals is defined as the amount of correction a patient needs to restore or substan-tially restore their coronal and/or sagittal alignment using the patients' morphological parameters, compensation capacity and harmony between the corrected sagittal and/or coronal curves and the other spinal curves. The amount of correction may comprise an angle or an angle of correction. The angle of correction for each patient may be different, thus providing a patient-specific approach. Therefore, patients with larger spinopelvic deformities may receive more extensive preparation, or additional corrective proce-dures to avoid under correction. The angle of correction will be used to achieve neutral alignment of sagittal and/or coronal curves for neutral implantation of at least one spinal implant. Alternatively, the angle of correction or a degree of correction may allow the upper vertebral body inferior facing surface to be parallel to the lower vertebral body superior facing surface to facilitate easier implantation of the at least one spinal implant. The angle of correction may comprise 0 degrees up to 40 degrees.

In various embodiments, a total joint replacement method to restore alignment and/or motion may comprise a tradi-tional operative protocol or intraoperative method. The traditional method may be performed manually by a sur-geon, and may comprise the steps of: selecting a surgical approach; positioning the patient properly on a surgical table; confirming alignment using one or more intraopera-tive images; accessing the localized spinal segment in a spine region; selecting proper implant size (tensioning soft tissues and trialing) on at least one side; preparing an intervertebral space within the localized spinal segment (prepare endplate upper vertebral body, prepare endplate of lower vertebral body, pedicle osteotomy and keel cuts/ channels) on the at least one side; and/or deploying or implanting the total joint spinal implant on the at least one side. The intraoperative method may further comprise the step of removing the implanted total joint spinal implant. The intraoperative method may further comprise the step of closing the surgical access to the localized spine segment in a spine region. A spine region may comprise a cervical region, a thoracic region, a lumbar region, a sacral region, and/or any combination thereof.

In at least one alternative embodiment, an intraoperative or operative method may comprise the steps of: selecting a surgical approach; positioning the patient properly on a surgical table; confirming alignment using one or more intraoperative images on a first side and a second side; accessing the localized spinal segment in a spine region; selecting proper implant size (tensioning soft tissues and trialing) on at least one side; preparing an intervertebral space within the localized spinal segment (prepare endplate upper vertebral body, prepare endplate of lower vertebral body, pedicle osteotomy and keel cuts/channels) on a first side; and/or deploying or implanting the total joint spinal implant on a first side; selecting proper implant size (ten-sioning soft tissues and trialing) on a second side; preparing an intervertebral space within the localized spinal segment (prepare endplate upper vertebral body, prepare endplate of lower vertebral body, pedicle osteotomy and keel cuts/ channels) on a second side; and/or deploying or implanting the total joint spinal implant on a second side. The intraop-erative method may further comprise the step of removing the implanted total joint spinal implant. The intraoperative method may further comprise the step of closing the surgical access to the localized spine segment in a spine region. A spine region may comprise a cervical region, a thoracic region, a lumbar region, a sacral region, and/or any combi-nation thereof.

As part of the preoperative planning and/or operative execution stage, a physician may collect data and calculate a variety of spinal and/or spinal/pelvic parameters, which may be measured from various radiographic or other images by hand or by use of computing equipment. FIG. 35 describes various selected surgical measurements (SSM) which may be measured, estimated and/or calculated from various non-invasive imaging modalities, which may include the collection and processing of data by semi-automated and/or automated equipment (e.g., a computing system) to create one or more virtual models of the target anatomy. The projected surgical measurement (PSM) or selected surgical measurement (SSM) data may include the different measurements highlighted in FIG. 35. The PSM or SSM data may include one or more of pelvic incidence (PI), pelvic tilt (PT), sacral slope (SS), L1 pelvic angle (L1PA), sagittal vertical axis (SVA), center of rotation (COR), lum-bar lordosis (LL), segmental lordosis, regional lordosis, wedge angle vertebral body, wedge angle disc, osteotomy sagittal angle, osteotomy transverse trajectory, osteotomy coronal trajectory, convergence angle or transverse pedicle angle, anterior-posterior (A/P) distance, neutral alignment, disc height, implant sizing and/or any combinations thereof.

Figures 36A, 36B:
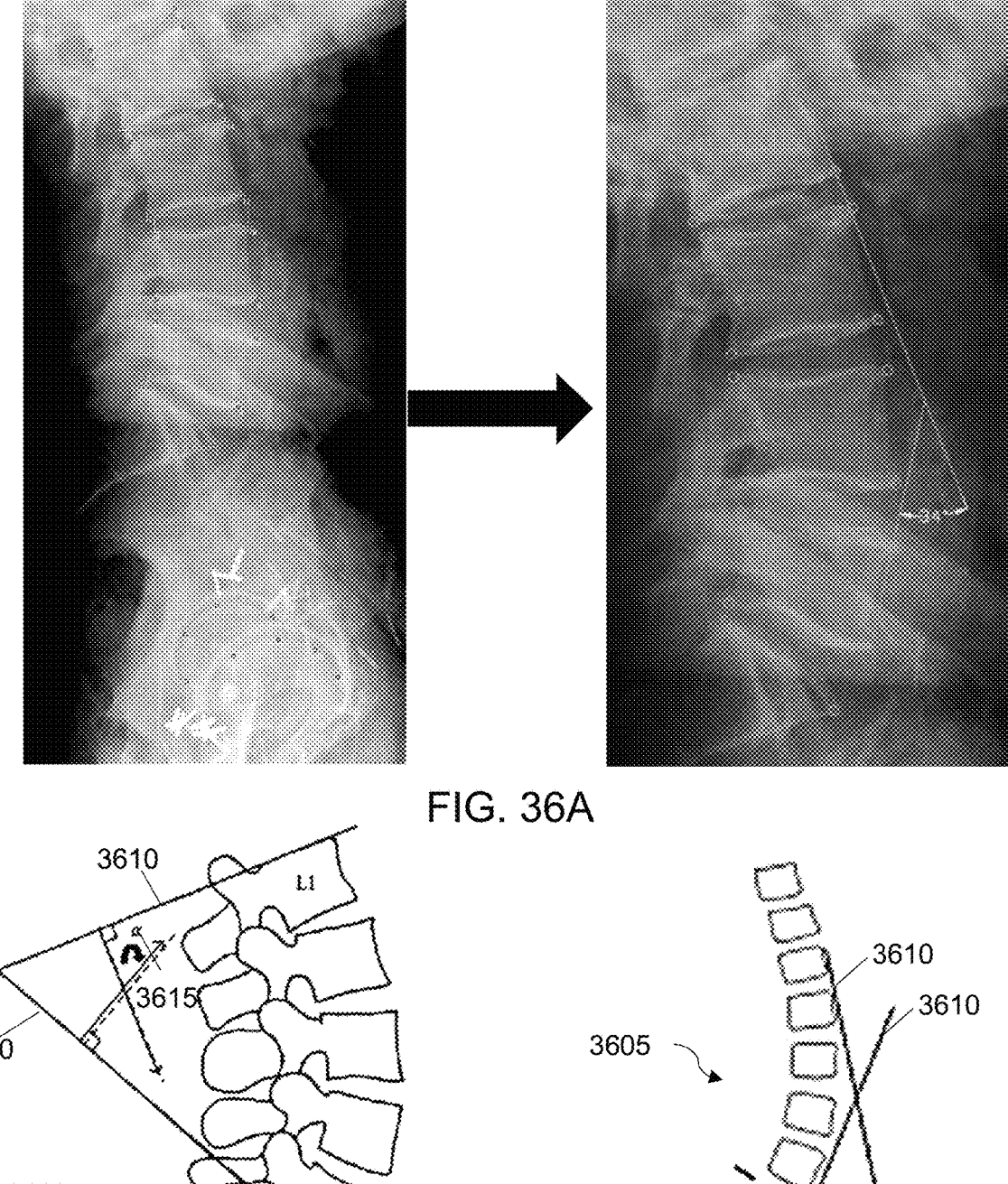
FIGS. 36A-36O depict various embodiments for using image data in analysis and computation of various SSMs.

With reference to FIG. 35 and FIGS. 36A-36B, the step of calculating one or more selected surgical measurements (SSM) from the targeted anatomy may comprise the calculation of vertebral lumbar lordosis (LL) 3600, 3605. The LL may use any methods known in the art. This includes using Cobb's method 3600 or Anterior Tangent Method 3605. The angle of the inward curve of the lumbar spine (just above the buttocks) is expressed as the average value between the angles obtained by Cobb's method 3600 and the Anterior Tangent Method 3605. One or more operative images may be accessed to draw patient-specific indicia or markers. Indicia or markers may further include tangent lines. Using Cobb's method 3600, tangent lines 3610 may be drawn along the superior end of L1 and S1. Perpendicular to each of the lines, an angle 515, α, is formed. Also, the Anterior Tangent Method 3605 can be calculated as the angle 3620 between tangent lines 3610 drawn through the anterior aspect of L5 and L1. Tangent lines as described above may be derived from the user, surgeon or software indicated vertebral corner points.

Figure 36C:
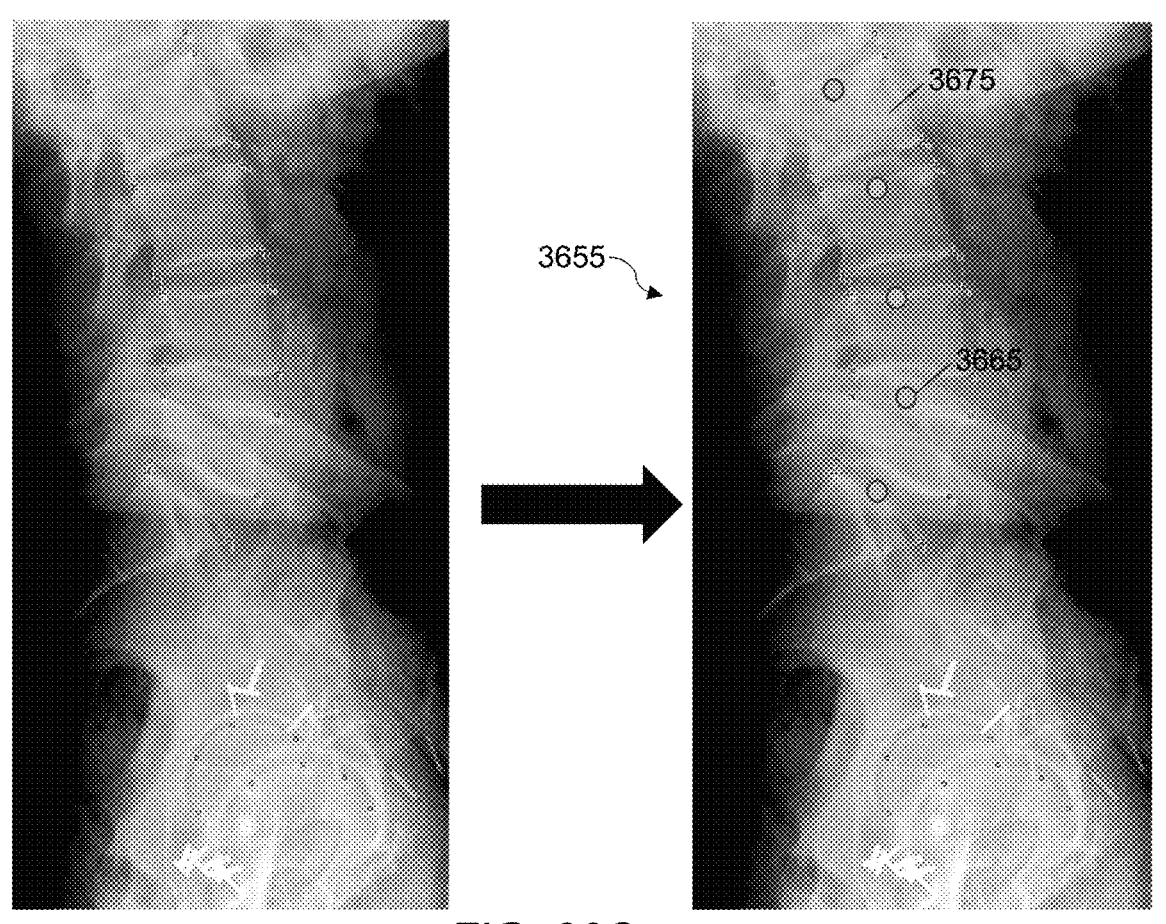
Figure 36D:
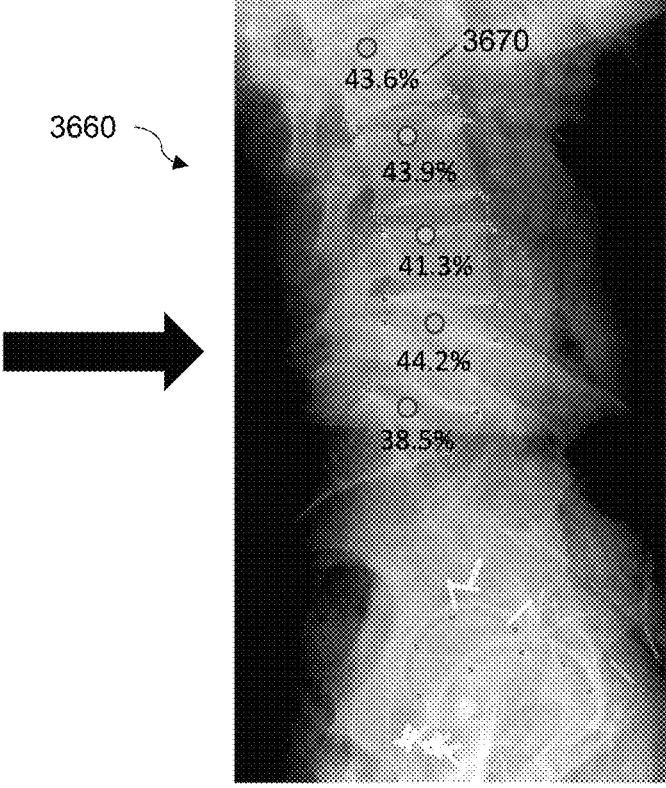

With reference to FIG. 35 and FIGS. 36C-36D, the step of calculating one or more selected surgical measurements (SSM) from the target anatomy may comprise the calculation of instantaneous center of rotation (ICOR) or center of rotation (COR) 3670. The one or more operative images may be accessed to draw patient-specific indicia or markers, which may further include points or circles that highlight the center of rotation 3655 within a portion of a spine within a spine region. COR points or circles 3665 may be derived or calculated by using the vertebral corner points within each vertebra 3675. The vertebral corner points may be user or software defined. The ICOR and/or the COR 3670 may be different or the same within each vertebra 3675 and/or spinal segment of a spinal region. The COR 3670 may be calculated by known methods in art. For example, the COR 3670 within the lumbar region for each spinal segment may be calculated using the Table 1 below. The COR 3670 and the COR points 3665 may be displayed.

TABLE 1

| COR Calculation | | |
| --- | --- | --- |
| Lumbar Level | Horizontal | Vertical |
| L51 | 38.5% of S1 corner points | 50.0% of L5S1 at 38.5% |
| L45 | 44.2% of L5 corners | 00.0% of L45 at 44.2% |
| L34 | 41.3% of L4 corners | 00.0% of L34 at 41.3% |
| L23 | 43.9% of L3 corners | 00.0% of L23 at 43.9% |
| L12 | 43.6% of L2 corners | 00.0% of L12 at 43.6% |

Figure 36E:
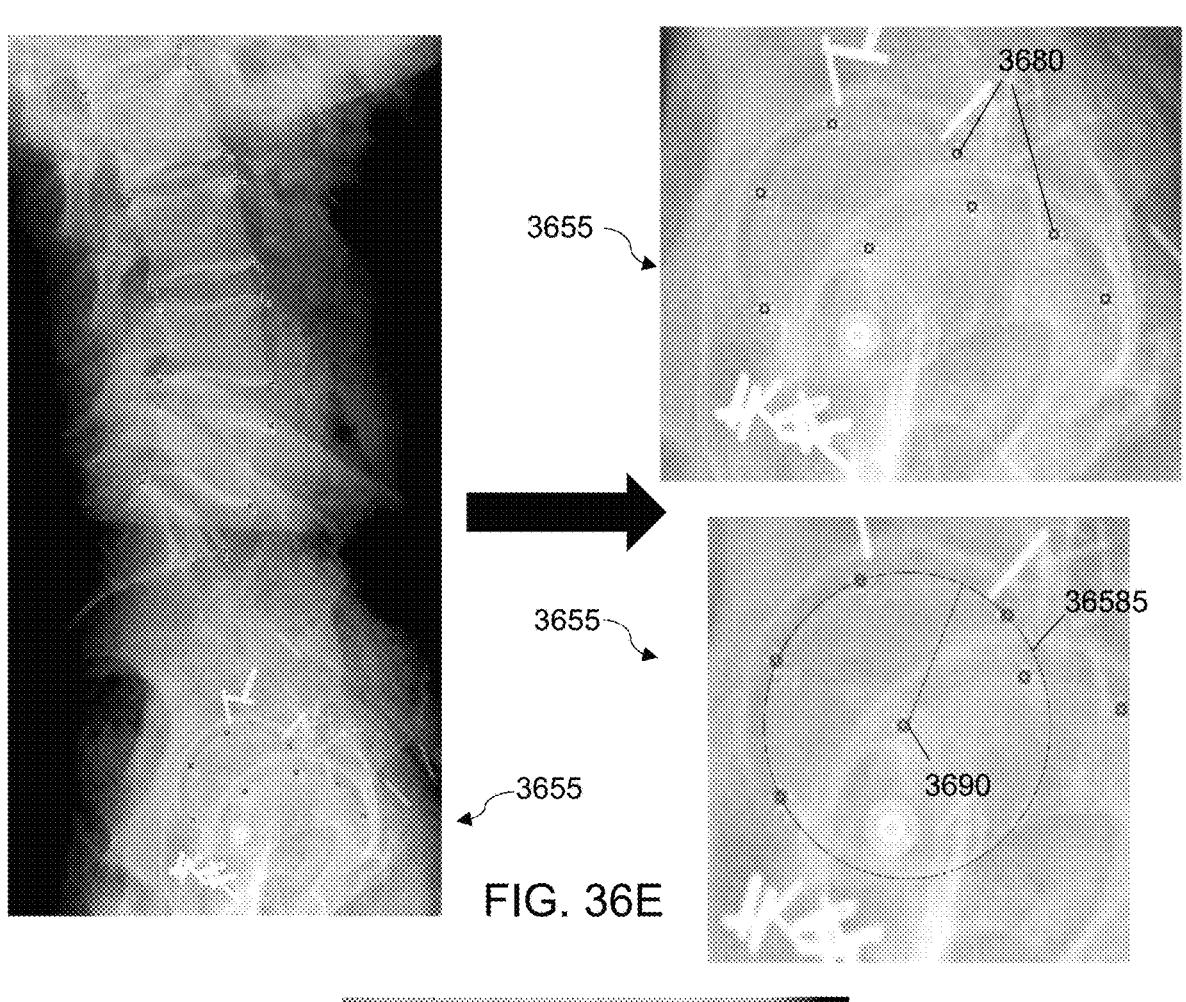
Figure 36F:
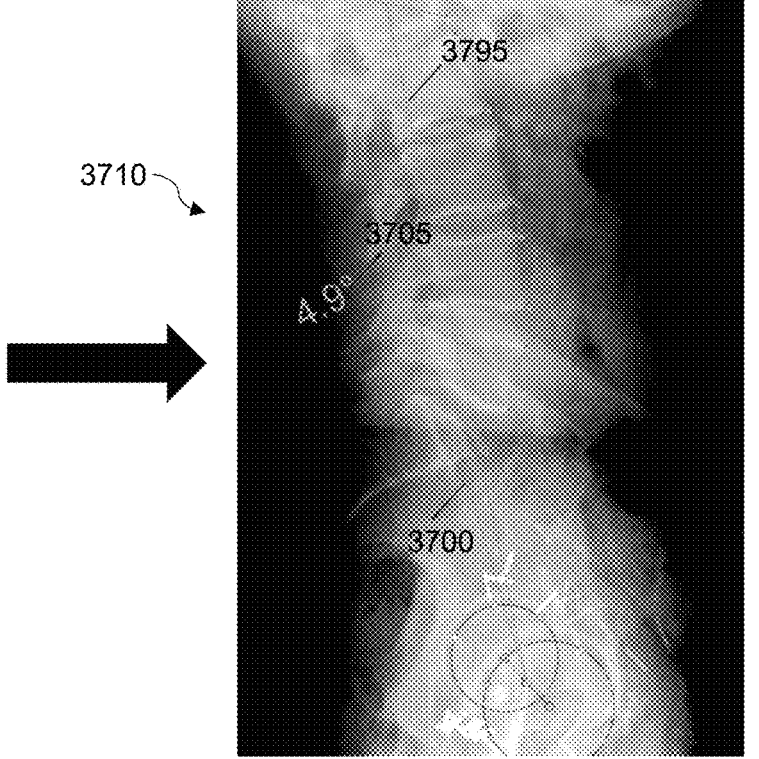

With reference to FIG. 35 and FIGS. 36E-36F, an exemplary step of calculating one or more selected surgical measurements (SSM) from the one or more virtual models of the target anatomy may comprise the calculation of L1 Pelvic Angle (L1PA). The one or more operative images may further comprise a portion of the hip, including the femoral head 3655. The one or more operative images may be accessed to draw patient-specific indicia or markers. Indicia or markers may further include points or circles 3680 that highlight the perimeter of the femoral head 3655. A plurality of points or circles 3680 can be positioned along the perimeter of the femoral head using "best fit" to create a circle 3685 and obtain the best approximation for the center 3690 of the femoral head. Also, a point refinement via the steepest gradient may be used. Once the center 3690 of the femoral head is obtained, a first reference line 3695 may be projected or displayed onto the processed image or virtual model that extends from the center 3690 point of the femoral head axis to the L1 vertebral body. A second reference line 3700 may be projected or displayed onto the processed image 3710 that extends from the center 3690 point of the femoral head axis to the center of the S1 endplate. The first reference line 3695 and the second reference line desirably forms an angle 3705.

Figure 36G:
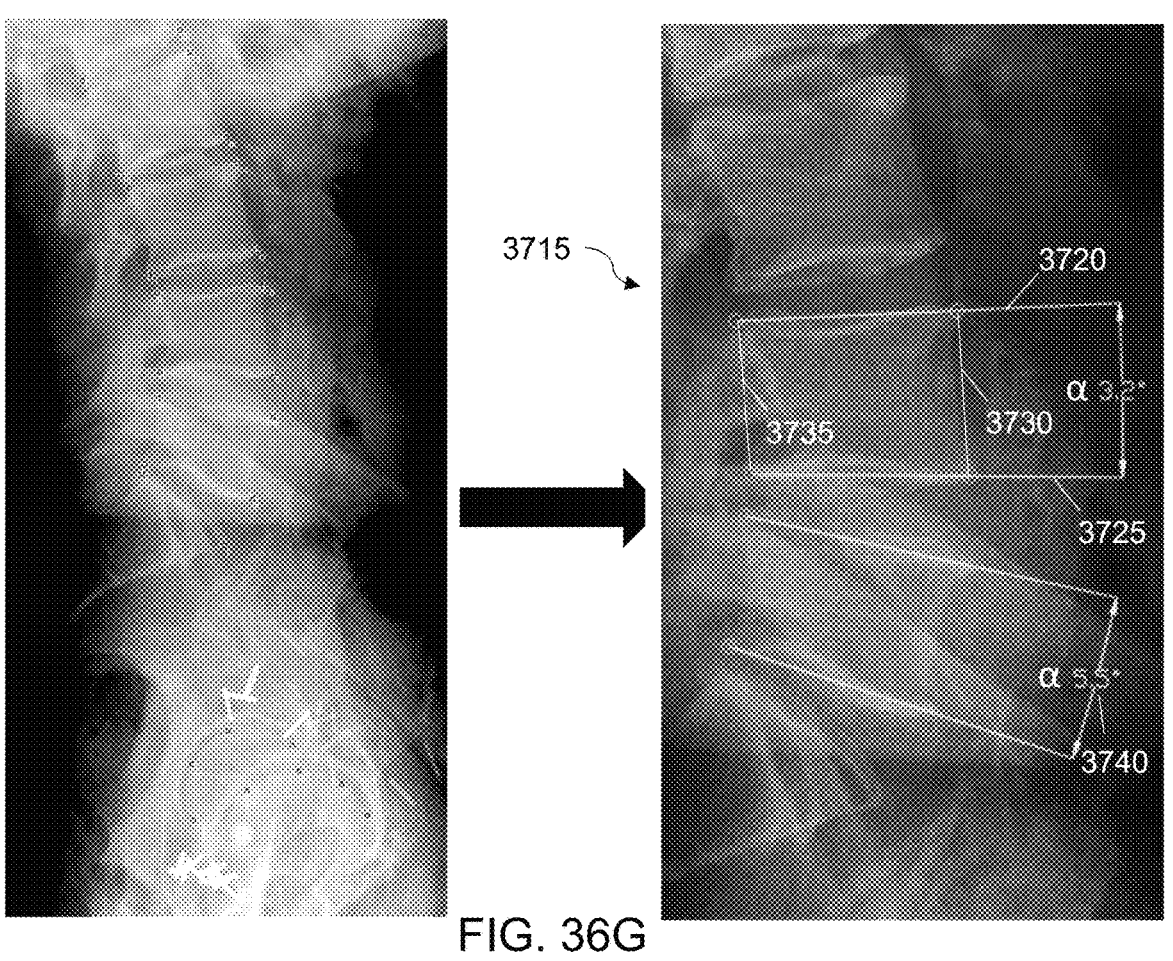
Figure 36H:
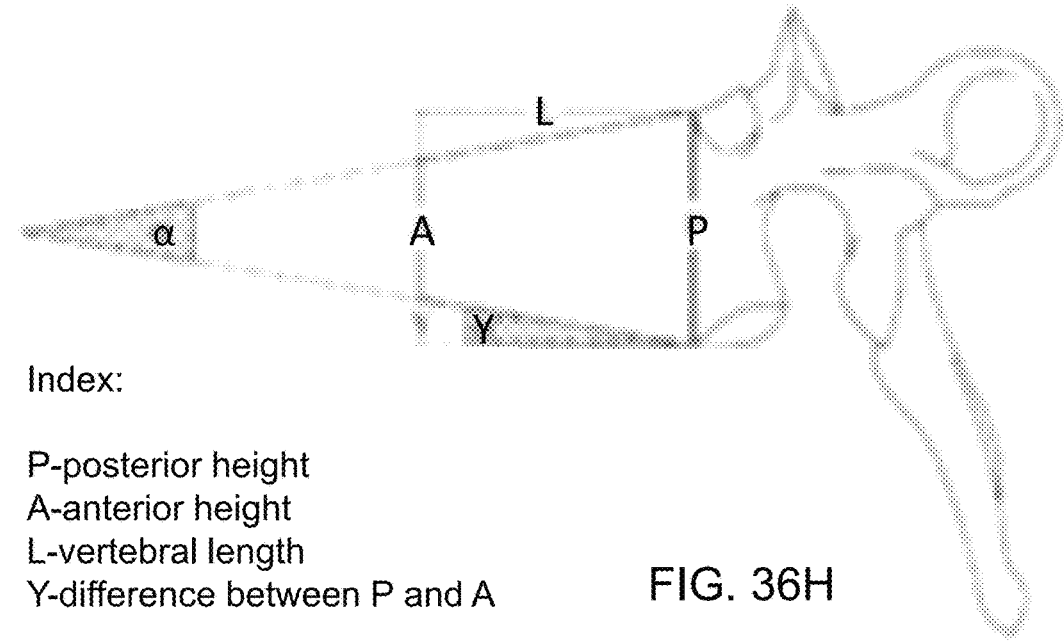

With reference to FIG. 35 and FIGS. 36G-36H, the step of calculating one or more selected surgical measurements (SSM) may comprise the calculation of a vertebral body wedge angle 3740. The one or more operative images may comprise patient-specific indicia or markers, which may include tangent lines, reference lines and/or points or angles. The indicia or makers may be disposed via user and/or by the software. The image may include a plurality of reference lines 3720,3725,3730,3735 on the vertebral body to calculate the vertebral body wedge angle 3740, α. The vertebral wedge angle is defined as $\alpha=2 \; TAN^{-1}(Y/L)$ when $Y=(P-A)/2$. The vertebral wedge angle 3740, α, may also be defined as the angle formed by two lines connecting upper endplate and lower endplate of a vertebral body.

Figure 36I:
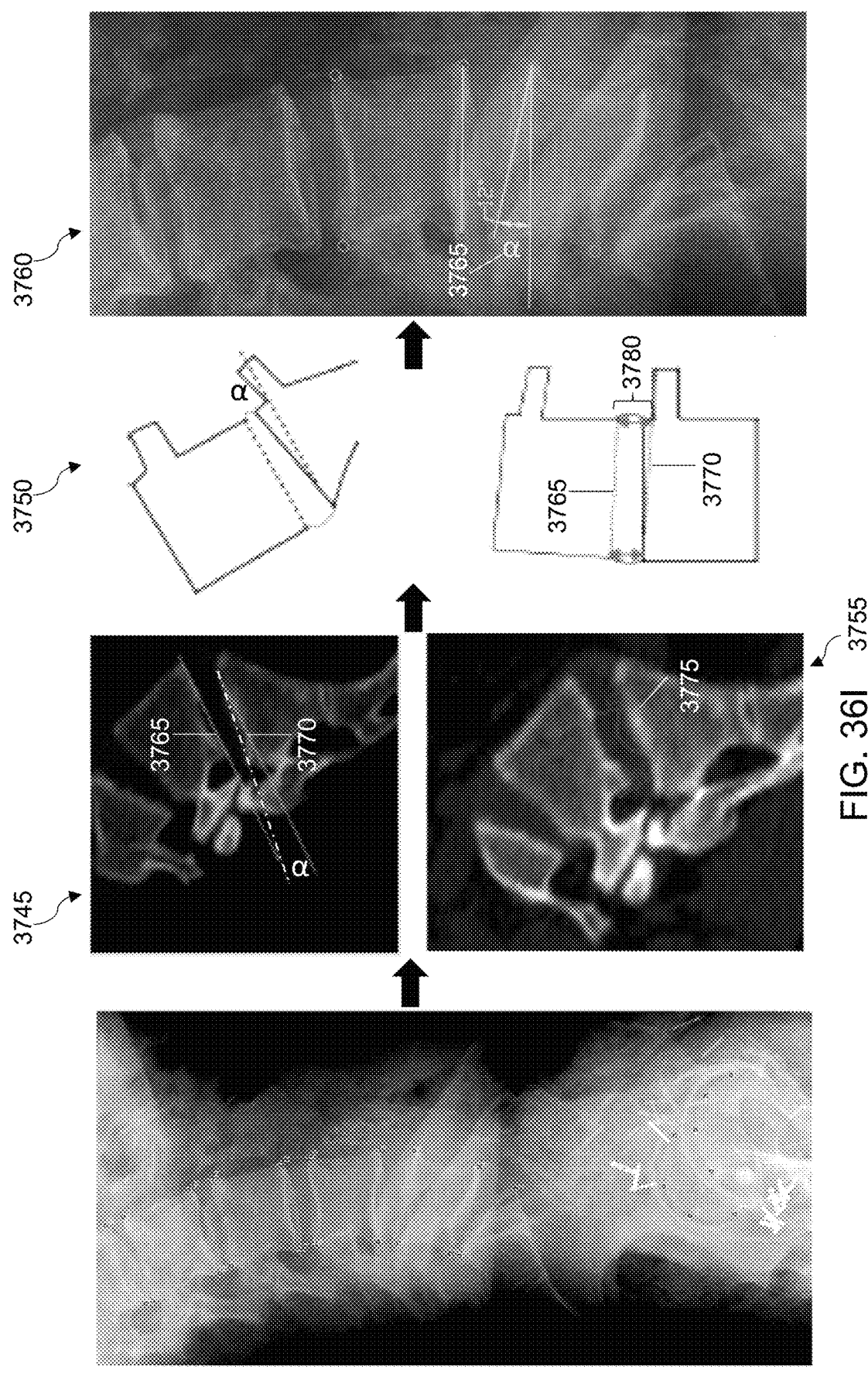

With reference to FIG. 35 and FIG. 36I, the step of calculating one or more selected surgical measurements (SSM) may comprise the calculation of an osteotomy sagittal angle or degree of osteotomy in the sagittal plane and/or neutral alignment. The one or more operative images may further include tangent lines, reference lines and/or points or angles. The indicia or makers may be disposed via user and/or by the software. The spinal implant is intended to be deployed between an intervertebral space of an upper and lower vertebra and the spinal implant should be parallel relative the lower endplate of the upper vertebra and the upper endplate of the lower vertebra. This allows the spinal implant to be disposed into a neutral position and/or neutral alignment allowing full range of motion and improve overall spinal alignment. A plurality of reference lines 3765, 3770 may extend across the images of lower endplate of the upper vertebra and the upper endplate of the lower vertebra. The plurality of reference lines 3765, 3770 should be parallel or neutrally aligned 3780 to each other. A second image or model 3755 may comprise an object 3775 such as a virtual spinal implant, which may be placed and/or projected into the image 3755 to confirm that the object 3775 contains a neutral alignment 3780 within the intervertebral disc space.

Neutral alignment 3780 is defined as the reference line 3765 of the lower endplate of the upper vertebra and the reference line 3770 of upper endplate of the lower vertebra resulting in a portion of the endplate reference lines 3765 are parallel. Alternatively, neutral alignment 3780 is defined as the reference line 3765 of the lower endplate of the upper vertebra and the reference line 3770 of upper endplate of the lower vertebra resulting in the entirety of the endplate reference lines 3765 are parallel. The final calculation of the osteotomy sagittal angle or degree of osteotomy within sagittal plane 3785, α, may be disposed onto another image or model 3760. Furthermore, the degree of osteotomy within the coronal plane or the osteotomy coronal angle may also be calculated.

Figures 36J, 36K:
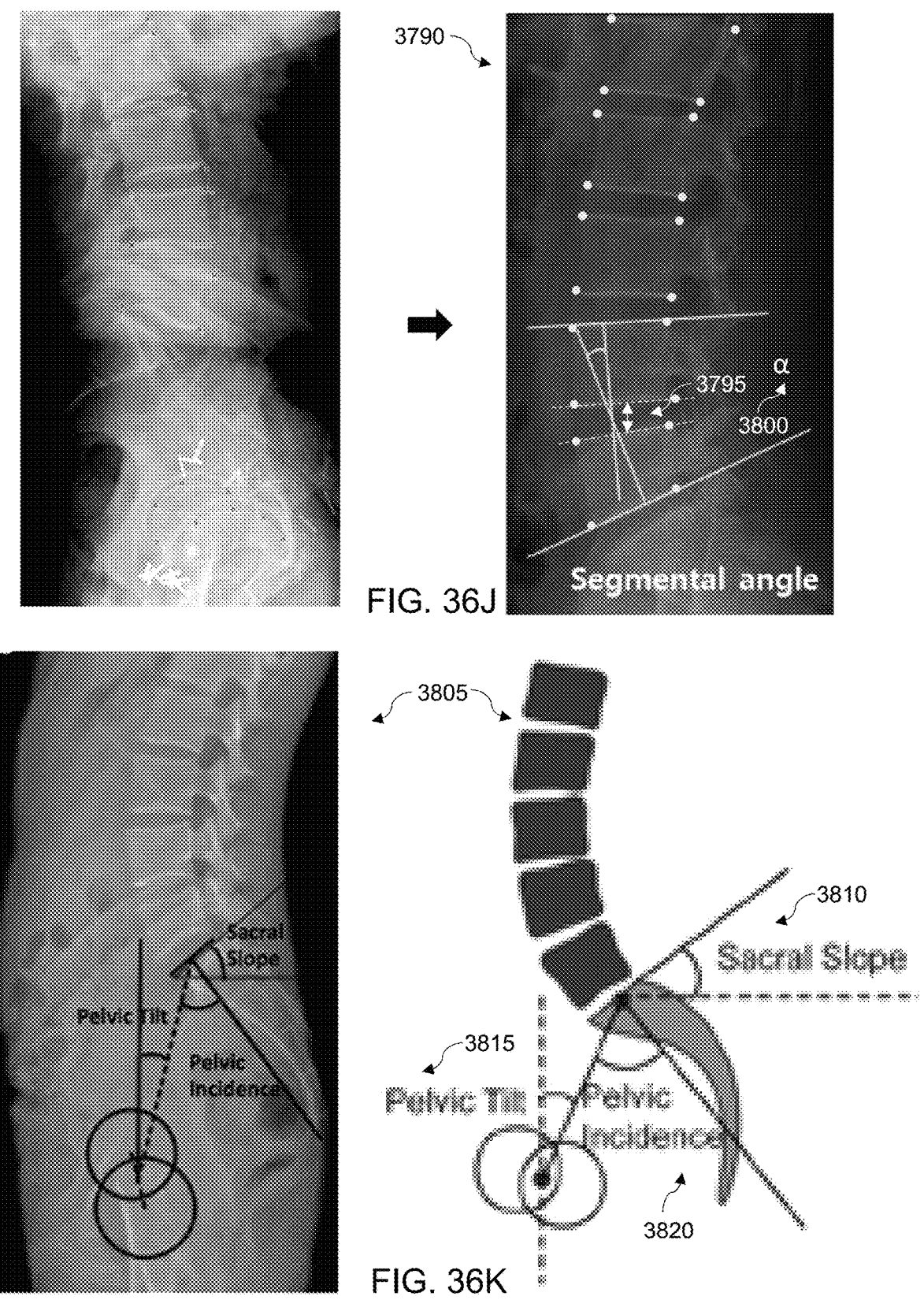
Figures 36M, 36N, 36O:
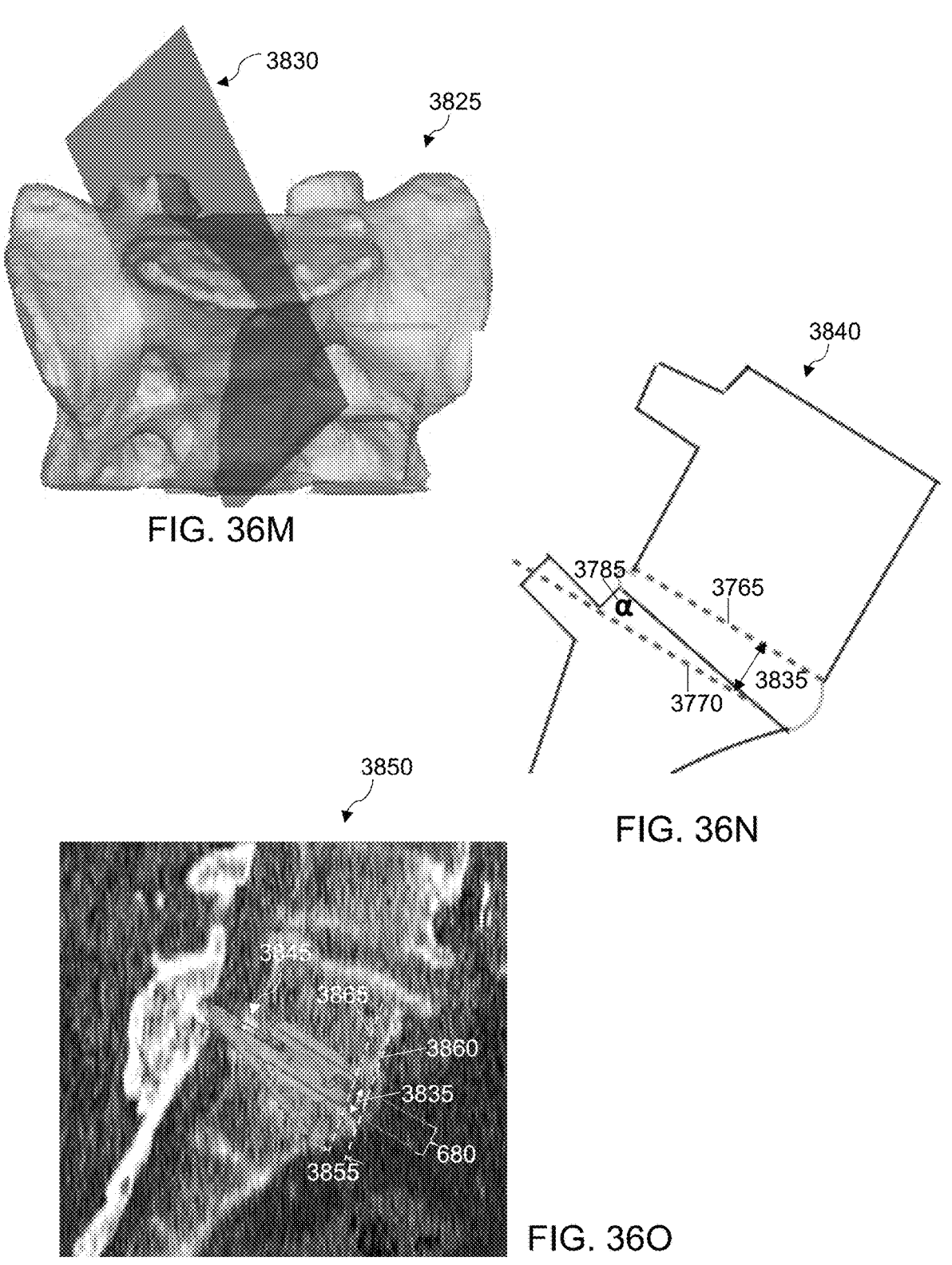

With reference to FIG. 35 and FIG. 36J, the step of calculating one or more selected surgical measurements (SSM) may comprise the calculation of segmental angle 3800. The one or more operative images may comprise patient-specific indicia or markers or may further include tangent lines, reference lines and/or points or angles. The technique for measuring segmental disc angles 3800 may require measurement of the disc height 3795 to produce the segmental angle 3800. The segmental angle 3800 is the angle between the upper and lower endplates at the targeted intervertebral disc space where surgery may take place. The disc height 3795 is the distance between the upper and lower endplates at the center of the targeted intervertebral disc space at the surgical site from the sagittal view. Alternatively, the disc height 3795 may be the distance between the upper and lower endplates of the targeted intervertebral disc space at the right side and left side of the intervertebral space divided by two to be reflected as disc height 3795=(a+b)/2.

With reference to FIG. 35 and FIGS. 36K-36L, the step of calculating one or more selected surgical measurements (SSM) may comprise the calculation of sacral slope (SS) 3810, pelvic tilt (PT) 3815 and pelvic incidence (PI) 3820. The one or more operative images may comprise patient-specific indicia or markers or may further include tangent lines, reference lines and/or points or angles. The SS 3810 and the PT 3815 are variable dependent on the version of the pelvis around the hip axis. The SS 3810 is defined as the angle between the endplate of S1 and a horizontal line. The PT 3815 is defined as the angle between a vertical line and the line joining the middle of the sacral plate and the axis of the femoral heads. The PI 3820 is desirably constant for each person and defined as an angle between a line joining the center of the upper endplate of S1 to the axis of the femoral heads and a line perpendicular to the upper endplate of S1. The technique for measuring the PI 3820 was measured by identifying the center of the femoral heads on the respective sagittal slices, then identifying the bicoxofemoral axis in the midsagittal plane. In the midsagittal plane, the endplates can be identified of each vertebral body from L1 to L5 and the sacrum allowing measurement of the vertebral body and disc angles as shown in FIG. 36L. In the disclosed example, a negative value indicated a kyphotic value while a positive value was lordotic.

With reference to FIG. 35 and FIGS. 36M-36O, the step of calculating one or more selected surgical measurements (SSM) may comprise the calculation or determination of implant sizing. Implant sizing may include implant length, implant height, and/or implant width. A sagittal plane view 3830 may be taken and one or more selected surgical measurements (SSM) may be determined or calculated, including the osteotomy sagittal angle or degree of osteotomy within the sagittal plane 3785 (see FIG. 36I) and a neutral alignment 3780 (see FIG. 36I). As previously disclosed, neutral alignment 3780 can be defined as the reference line 3765 of the lower endplate of the upper vertebra and the reference line 3770 of upper endplate of the lower vertebra resulting in a portion of the endplate reference lines 3765 are parallel and/or an entirety of the endplate reference lines 3765 are parallel (along the entire endplate surfaces). A portion of parallel endplate surfaces or the entirety of parallel endplate surfaces can result in a neutral intervertebral disc height 3835. An approximated implant 3845 may be disposed onto a third image or model 3850. One or more implants 3845 of different sizes may be inserted or projected within the neutrally aligned intervertebral disc space 3780 until the desired one or more implants 3845 obtains a desired implant positioning, implant height, implant width, and/or implant length. The images and/or any virtual models thereof may be rotated in different axis and plane views to confirm proper or desired implant sizing and/or implant positioning.

Once various of the above measurements and/or calculation have been obtained, the step of calculating one or more selected surgical measurements (SSM) may comprise a calculation or determination of a planned or desired implant positioning. Implant positioning may comprise one or more of the following: (1) COR (see FIGS. 36C-36D); (2) A/P distance 3855 that the anterior most portion 3865 of the one or more implants 3845 from the anterior surface 3860 of the upper and/or lower vertebral body (see FIG. 36O); and/or (3) convergence angle or transverse pedicle angle, and/or any combination thereof. Convergence angle or transverse pedicle angle can be defined by creating a central axis measurement from a spinous process to the anterior vertebral body then measuring one or more angles from the central axis to the mid-axis of at least one pedicle. Alternatively, the convergence angle or transverse pedicle angle can be defined by creating a central axis measurement from spinous process to the anterior vertebral body then measuring a first angles from the central axis to the mid-axis of the first pedicle and measuring a second angle from the central axis to the mid-axis of the second pedicle.

The planned and/or desired implant positioning may help determine implant sizing. If desired, parameters or dimensions of one or more implants may be inserted onto/into an image and/or virtual model of the anatomy and/or rotated in different planes—isometric, sagittal, coronal, A/P and/or any combination thereof—to confirm implant sizing and implant position. Images and/or models may comprise 2D or 3D images/models. Implant positioning may further comprise (4) sagittal osteotomy angle (see FIG. 36I); (5) coronal osteotomy angle; and/or (6) neutral alignment.

In various embodiments, the preoperative protocol may comprise the step of completing a Perioperative and Post-operative Anesthesia Protocol for Enhanced Recovery After Surgery (ERAS). The ERAS® refers to patient-centered, evidence-based, multidisciplinary team developed care pathways for a surgical specialty and facility culture to reduce the patient's surgical stress response, optimize their physiologic function, and facilitate recovery. These care pathways form an integrated continuum, as the patient moves from home through the pre-hospital/preadmission, preoperative, intraoperative, and postoperative phases of surgery and home again.

Operative or Intraoperative Method

In various embodiment, an exemplary method to restore alignment and motion may further comprise an operative protocol or intraoperative method. With reference to FIG. 3A, an intraoperative or operative protocol may comprise the steps of: selecting a surgical approach 305; positioning the patient properly on a surgical table 310; confirming alignment using one or more intraoperative images 315; accessing the localized spinal segment in a spine region 320; selecting proper implant size (tensioning soft tissues and trialing) on at least one side 325; preparing an intervertebral space within the localized spinal segment (prepare endplate upper vertebral body, prepare endplate of lower vertebral body, pedicle osteotomy and keel cuts/channels) on the at least one side 330; and/or deploying or implanting the total joint spinal implant on the at least one side 335. The intraoperative method may further optionally comprise the step of removing the implanted total joint spinal implant (not shown). The intraoperative method may further comprise the step of closing the surgical access to the localized spine segment in a spine region 340. A spine region may comprise a cervical region, a thoracic region, a lumbar region, a sacral region, and/or any combination thereof.

With reference to FIG. 3B, an alternative embodiment of the intraoperative or operative method comprises the steps of: selecting a surgical approach 350; positioning the patient properly on a surgical table 355; confirming alignment using one or more intraoperative images on a first side and a second side 360; accessing the localized spinal segment in a spine region 365; selecting proper implant size (tensioning soft tissues and trialing) on at least one side 370; preparing an intervertebral space within the localized spinal segment (prepare endplate upper vertebral body, prepare endplate of lower vertebral body, pedicle osteotomy and keel cuts/channels) on a first side 375; and/or deploying or implanting the total joint spinal implant on a first side 380; selecting proper implant size (tensioning soft tissues and trialing) on a second side 385; preparing an intervertebral space within the localized spinal segment (prepare endplate upper vertebral body, prepare endplate of lower vertebral body, pedicle osteotomy and keel cuts/channels) on a second side 390; and/or deploying or implanting the total joint spinal implant on a second side 395. The intraoperative method may further optionally comprise the step of removing the implanted total joint spinal implant (not shown). The intraoperative method may further comprise the step of closing the surgical access to the localized spine segment in a spine region 398. A spine region may comprise a cervical region, a thoracic region, a lumbar region, a sacral region, and/or any combination thereof.

In another exemplary embodiment, an intraoperative or operative protocol may comprise the steps of: selecting a surgical approach; positioning the patient properly on a surgical table; confirming alignment using one or more intraoperative images on a first and second sides; accessing the localized spinal segment in a spine region; selecting proper implant size (tensioning soft tissues and trialing) on the first and second sides; preparing an intervertebral space within the localized spinal segment (prepare endplate upper vertebral body, prepare endplate of lower vertebral body, pedicle osteotomy and keel cuts/channels) on the first and second sides; and/or deploying or implanting the total joint spinal implant on first and second sides. The intraoperative method may further comprise the step of removing the implanted total joint spinal implant from the first and/or second sides. The intraoperative method may further comprise the step of closing the surgical access to the localized spine segment in a spine region. A spine region may comprise a cervical region, a thoracic region, a lumbar region, a sacral region, and/or any combination thereof.

Figure 4A:
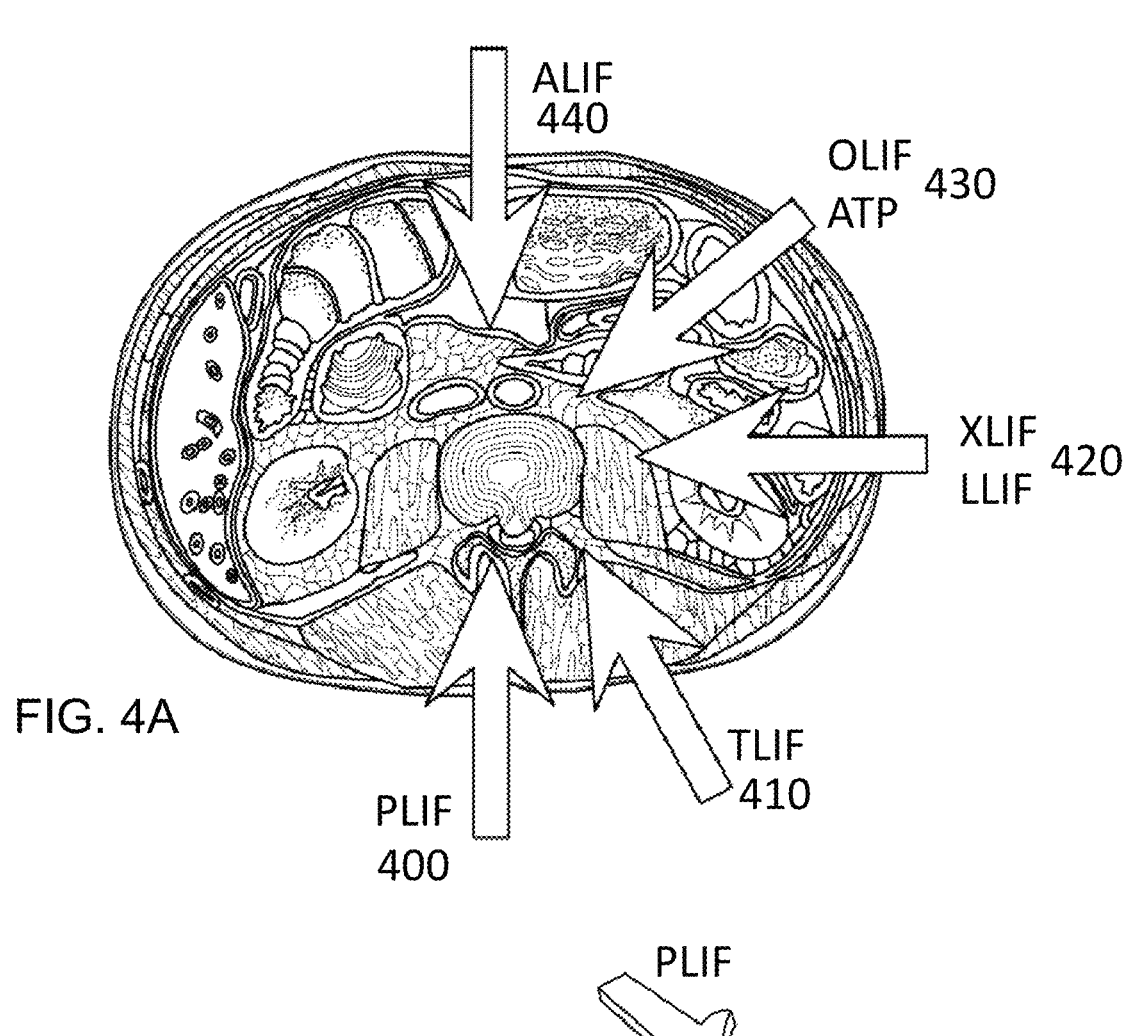
FIGS. 4A-4B depicts different views of available surgical approaches for deployment a total joint replacement spinal implant system.
Figure 4B:
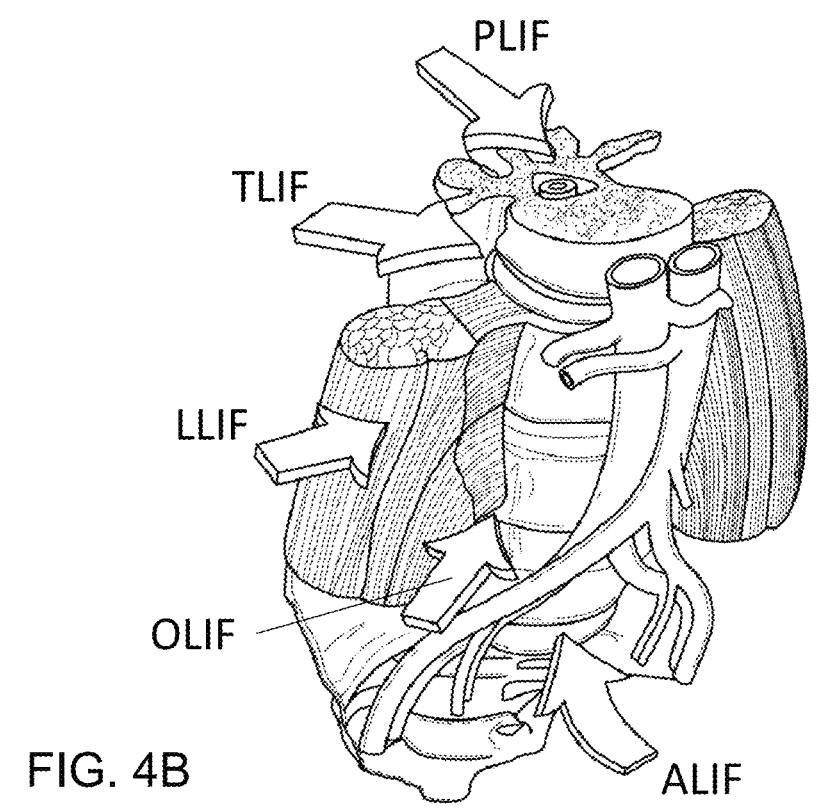

In another exemplary embodiment, the intraoperative method may comprise the step(s) of selecting one or more surgical approaches. With reference to FIGS. 4A-4C, the surgical approaches selected may be similar to standard surgical fusion approaches, including posterior lumbar interbody fusion (PLIF) 400, transforaminal lumbar interbody fusion (TLIF) 410, minimally invasive transforaminal lumbar interbody fusion (MI-TLIF), oblique lumbar interbody fusion/anterior to psoas (OLIF/ATP) 430, lateral lumbar interbody fusion (LLIF) 420, anterior lumbar interbody fusion (ALIF) 440 and/or any combination thereof. In one preferred embodiment, the surgical approach may comprise a PLIF or a TLIF.

In another embodiment, the intraoperative method may include the step of positioning the patient properly on a surgical table. The step of positioning the patient properly comprises the steps of positioning the patient onto the surgical table; and confirming alignment by acquiring one or more intraoperative images using at least one imaging technique. Patient positioning can be important to ensure restoration of sagittal alignment, mobility and implantation of the spinal implant. In various embodiments the patient can be initially positioned in a prone position in a neutral alignment with legs extended on an Andrews or Jackson table with bolsters. The patients' prone position on the table should desirably match or substantially match the patient's standing sagittal position. The abdomen should remain free with no pressure on the bladder and with hip pads under the anterior superior iliac spine. In many cases the surgeon will wish to avoid supraphysiologic positioning (flexion or extension of the lumbar spine). In addition, mechanical deep vein thrombosis prophylaxis may be followed per hospital or center protocol.

In another embodiment, the step of positioning the patient properly further comprises the step of confirming alignment by acquiring one or more intraoperative images using at least one imaging technique. Once the patient is properly positioned, intraoperative imaging and/or lateral intraoperative imaging can be used to evaluate sagittal and/or coronal alignment using a preferred imaging technique. Various exemplary imaging techniques can include an MRI, a radiograph, a CT scan, an ultrasound, and/or any combination thereof.

If desired, an imaging mechanism of the at least one imaging technique may be provided and/or programmed with an approximated pre-determined preoperative goals for sagittal vertical axis (SVA) alignment and/or coronal alignment. The imaging mechanism may comprise a Jackson frame. One or more intraoperative images can be captured using one or more imaging techniques. The one or more intraoperative images can be compared to preoperative one or more images from the preoperative imaging protocol. In various embodiments, the comparison, confirmation and/or verification of alignment will desirably match and/or substantially match preoperative coronal and/or SVA restoration and mobility goals (e.g., the angle of correction or AOC). In other embodiments, the intraoperative sagittal alignment position may match standing neutral sagittal alignment. If any adjustments to the imaging mechanism and/or the patient are necessary, a second or subsequent set(s) of one or more intraoperative images can be acquired. The later comparison, confirmation and/or verification of alignment may desirably match or substantially match preoperative coronal and/or SVA restoration and mobility goals (e.g., the angle of correction). If desired, the physician may repeat these cycles until SVA alignment to preoperative goals are met.

Figure 5:
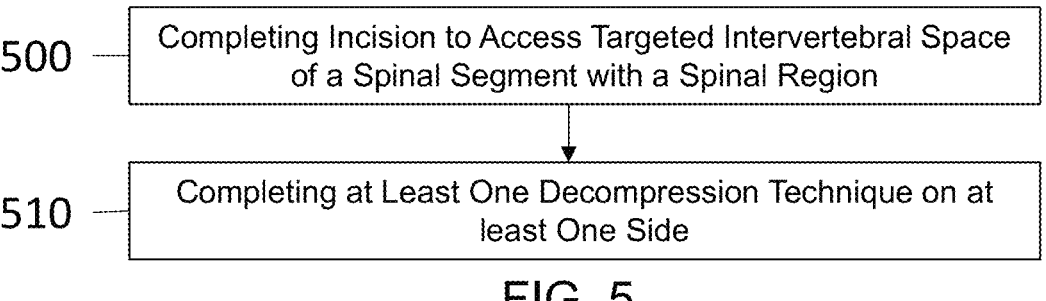
FIG. 5 graphically illustrates one least one embodiment for a method of accessing the localized spine segment in a spine region.

With reference to FIG. 5, an intraoperative method may comprise the step of accessing a localized spine segment within a spine region 500. The step of accessing the localized spinal segment in a spine region may further comprise the steps of completing the incision to access a targeted vertebral segment within the spinal region; and/or completing at least one decompression technique 510 as well known in the art. I desired, completing the incision to access the targeted spinal segment within a spinal region may include localizing the incision at, near and/or proximate to the localized spinal segment in desired spine region, which may include open, less-invasive and/or minimally invasive access techniques. The spine region may include a thoracic region, a cervical region, lumbar region, sacral region and/or any combination thereof. The localized spinal segments may include one or more cervical vertebral segments (C1-C8) or portions thereof, one or more thoracic vertebral segments (T1-T12) or portions thereof, one or more lumbar vertebral segments (L1-L5) or portions thereof, and/or a sacral vertebral segment (S1-S5) or portions thereof. Where an open technique is desired, the surgeon may desirably extend the incision from the inferior endplate of the superior adjacent level to the inferior endplate of the index level within a spinal segment of a spine region. For example, for the surgical treatment of L4-L5, the incision should extend from the inferior endplate of L3 to inferior endplate of L5.

In various embodiments, the surgeon can complete a standard midline subperiosteal exposure that extends laterally to include the medial edge of transverse process, and utilize intraoperative imaging with an imaging technique to confirm the proper index level and/or targeted spinal segment. The surgeon may then expose the entirety of the facet joint and lamina at the index level. Alternatively, the surgeon may expose the entirety of the facet joint, lamina and transverse process. The surgeon may choose to not dissect the transverse process of the L5 vertebra where it is desirous or necessary to maintain the integrity of the iliolumbar ligament, as disruption of the iliolumbar ligament can weaken the transverse process (which may be especially relevant for patients with spondylolisthesis at L5-S1). Furthermore, the surgeon may elect to avoid violating the cranial facet capsule of the facet joint and/or to avoid transverse process fracture (where appropriate), especially at L5. In various embodiments, the surgeon may attempt to achieve hemostasis.

With reference to FIGS. 6A-6B, exemplary steps of at least one decompression technique may be followed to desirably achieve pedicle-to-pedicle exposure of the foramen and exiting nerve root and/or exposure of the "hidden zone" and/or Kambin's triangle on at least one side. The one or more decompression techniques may include a laminectomy, a laminotomy, a foraminotomy, a laminoplasty, a discectomy, an annulotomy and/or any combination thereof. The one or more decompression techniques may comprise a complete or partial technique. The one or more decompression techniques may be completed on least one side. The one or more decompression techniques may be completed on a first side and a second side.

Alternatively, the step of completing at least one decompression technique may comprise a laminectomy and at least one facetectomy. The at least one facetectomy may comprise an inferior and/or superior facetectomy. The at least one facetectomy may comprise a complete/full or partial facetectomy. The laminectomy may include a standard laminectomy, a Gill laminectomy and/or a hemi-Gill laminectomy.

In one exemplary embodiment, the step of completing at least one decompression may comprise a laminectomy 600, first facetectomy 605 and a second facetectomy 610. The laminectomy may comprise a complete or partial laminectomy. The first or second facetectomy may comprise a complete or partial facetectomy. The first facetectomy may comprise a complete inferior facetectomy, complete superior facetectomy, a partial inferior facetectomy, and/or a partial superior facetectomy. The second facetectomy may comprise a complete inferior facetectomy, complete superior facetectomy, a partial inferior facetectomy, and/or a partial superior facetectomy. In another embodiment, the step of completing at least one decompression technique may comprise a complete or partial laminectomy, a first facetectomy that includes a complete inferior facetectomy, a second facetectomy that includes a partial superior facetectomy. The step of completing at least one decompression technique may further comprise a discectomy and/or an annulotomy.

Also, the step of completing at least one decompression technique may comprise a laminectomy, at least one facetectomy and a discectomy 615. The at least one facetectomy may comprise a complete inferior facetectomy, complete superior facetectomy, a partial inferior facetectomy, and/or a partial superior facetectomy. In an exemplary embodiment, the step of completing at least one decompression technique may comprise a complete or partial laminectomy, a complete inferior facetectomy, a partial superior facetectomy, a discectomy and an annulotomy 620.

In another embodiment, a laminectomy and the at least one facetectomy may be performed according to standard surgery techniques. In another embodiment, the laminectomy and/or facetectomy may be performed according to standard surgery techniques with supplemental considerations, such as confirming flushness and/or the location of the nerve root(s). The surgeon may confirm that the medial portion of the superior articular process should be flush with the medial wall of the inferior pedicle. Also, the surgeon may remove the top portion of the superior articular process to be flush with the inferior pedicle. In some embodiments the surgeon may want to avoid violating the cranial facet capsule of the facet joint. The supplemental considerations may further include having the surgeon confirm the visualization and/or location of the nerve root. The exiting nerve root should be exposed and visualized from the hidden zone to the far lateral zone. Any tethering tissue from the lateral pedicle to the exiting nerve root should be released to allow gentle superior-lateral retraction of the exiting nerve root. The surgeon may desirably want to avoid dissecting iliolumbar ligaments to avoid weakening of the transverse process. The surgeon may utilize gentle distraction of the nerve root. The veins near the lateral tethering ligaments may cause bleeding and may be controlled with hemostatic agents or bipolar forceps. Furthermore, the surgeon may elect to release the intraforaminal ligaments to allow for complete decompression of the traversing and exiting nerve roots. If the surgeon identifies osteophytes, the surgeon may engage in the operation to remove any compressive osteophytes using standard instruments ad/or techniques known in the art.

In one embodiment, a discectomy may be performed according to standard surgery techniques. In other embodiments, the discectomy may be performed to standard surgery techniques with supplemental considerations, such as avoidance of nerve damage. In such a case the surgeon could protect the exiting nerve root and the lateral thecal sack by retracting both for protection of the neural elements prior to initiation of the discectomy. As best seen in FIG. 6B, such supplemental considerations may further include a discectomy and a rectangular annulotomy on a first side and/or a second side (e.g., a bilateral annulotomy). On a first side, the surgeon may incise the disc and complete a rectangular annulotomy from paracentral to far lateral zone. The discectomy should remove endplate cartilage, nucleus pulposus, while preserving the lateral annulus and anterior longitudinal ligament (ALL). On a second side, the surgeon may incise the disc and complete a rectangular annulotomy from paracentral to far medial zone. The same procedure may be completed bilaterally (e.g., on a first side and/or second side) to allow for bilateral trans-foraminal approach with complete discectomy. The surgeon should ensure that the entire nucleus pulposus is removed to minimize risk for future disc herniation and to allow adequate space for implantation of the prosthesis.

Additional supplemental considerations may further include mobilizing the intervertebral disc space of the spinal segment. The surgeon may consider utilizing an osteotome or a thin osteotome. The osteotome may be inserted medial to the pedicle preliminarily to mobilize the disc space. The surgeon may desirably want to avoid disruption of the endplates at the index level. The supplemental considerations may further include evaluation of patients with prior surgery. In the cases of patients with prior surgery at the index level, significant epidural scaring might make the decompression and/or disc preparation more challenging. The risk of incidental durotomy may be increased with patients who have had prior surgery. Additionally, the principle of identifying previously unoperated anatomy and working from a virgin area to a previously operated area for the decompression should be followed.

With reference to FIG. 7A, an exemplary intraoperative method may comprise the step of selecting a proper spinal implant size. The step of selecting the proper implant size may comprise the steps of: balancing soft tissue on at least one side 700; determining the proper implant length using implant length trial tools 710; and determining the proper implant height using implant height trial tools 720.

With reference to FIG. 7B, the step of selecting the proper implant size may further comprise the steps of: balancing soft tissue on the at least one side 740; determining the proper implant length using implant length trial tools one the at least one side 750; confirming approximated implant length by acquiring one or more images using at least one imaging technique 760; determining the proper implant height using implant length trial tools on the at least one side 770; confirming approximated implant height by acquiring one or more images using at least one imaging technique 780. The step of selecting the proper implant size may further comprise the step of matching the convergence of the implant trial height and/or implant trial length tools to match the axis of the pedicle at the treated spinal unit or spinal segment (e.g., matching the transverse pedicle angle at the treated spinal unit or spinal segment) on a first side and/or a second side.

In one embodiment, the step of balancing soft tissue by mobilizing the intravertebral space by using distractor tools may comprise a series of sequential steps. The surgeon may begin intervertebral space mobilization with the smallest provided distractor to increase intervertebral height at least one side. Alternatively, the surgeon may begin intervertebral space mobilization with the smallest provided distractor on a first side and/or a second side. The surgeon could sequentially introduce other distractors with increased width and/or height into the intervertebral space to allow tensioning of the soft tissues on at least one side. Alternatively, the surgeon could sequentially introduce other distractors with increased width and/or height into the intervertebral space to allow a first tensioning of the soft tissues on a first side and a second tensioning a second side. The first tensioning could be the same tension and/or substantially the same as the second tensioning. The first tensioning could be a different tension than the second tensioning.

In various techniques, the surgeon may desirably be aware that soft tissue responses could vary depending on the severity and duration of the patient's illness, so the amount of time to allow for soft tissue relaxation between insertion of larger distractors may differ. If desired, the surgeon will preferably avoid excessive distraction of the intervertebral space and endplate fracture or compression, although the proper device height may vary by patient (and will primarily be estimated in-situ based on soft tissue tension).

With reference to FIG. 8A, the step of determining the proper implant length using implant length trial tools may comprise the steps of: assembling and/or attaching a length trial tool 840; introducing at least one length trial on at least one side 843; verifying the center of rotation (COR) 846; and/or confirming proper implant length by acquiring at least one image using at least one imaging technique 849.

With reference to FIG. 8B, the step of determining the proper implant length using implant length trial tools may comprise the steps of: assembling and/or attaching a length trial tool 820; introducing at least one length trial on at least one side that follows along the transverse pedicle angle 823; verifying the center of rotation (COR) 826; and/or confirming proper implant length by acquiring at least one image using at least one imaging technique 829.

With reference to FIG. 8C, the step of determining the proper implant length using implant length trial tools may comprise the steps of: assembling a first and a second length trial tool 840; introducing the first length trial on a first side and the second length trial on a second side 843; verifying the center of rotation (COR) on a first side and a second side 846; and/or confirming proper implant length on a first side and a second side by acquiring at least one image using at least one imaging technique. 849

With reference to FIG. 8D, the step of determining the proper implant length using implant length trial tools may comprise the steps of; assembling a first and a second length trial tool 850; introducing the first length trial on a first side that follows, matches or substantially matches the first transverse pedicle angle and the second length trial on a second side that follows, matches or substantially matches the second transverse pedicle angle 863; verifying a first COR of a first length trial and a second COR of a second length trial 866; and/or confirming proper implant length on a first side and a second side by acquiring at least one image using at least one imaging technique 869. This approach allows the surgeon to introduce the length trials bilaterally to match each transverse pedicle angle on a first side and a second side. The first length trial may be the same length as the second length trial. The first length trial may be a different length than the second length trial. Accordingly, first transverse pedicle angle may comprise the same angle as the second transverse pedicle angle. The first transverse pedicle angle may comprise a different angle than the second transverse pedicle angle.

In various embodiments, a step of determining the proper implant length using implant length trial tools may comprise the step of assembling a length trial tool. The surgeon may require the use of sequential length trials. The surgeon may confirm that a surgical kit may contain at least three length trials.

Figure 9:
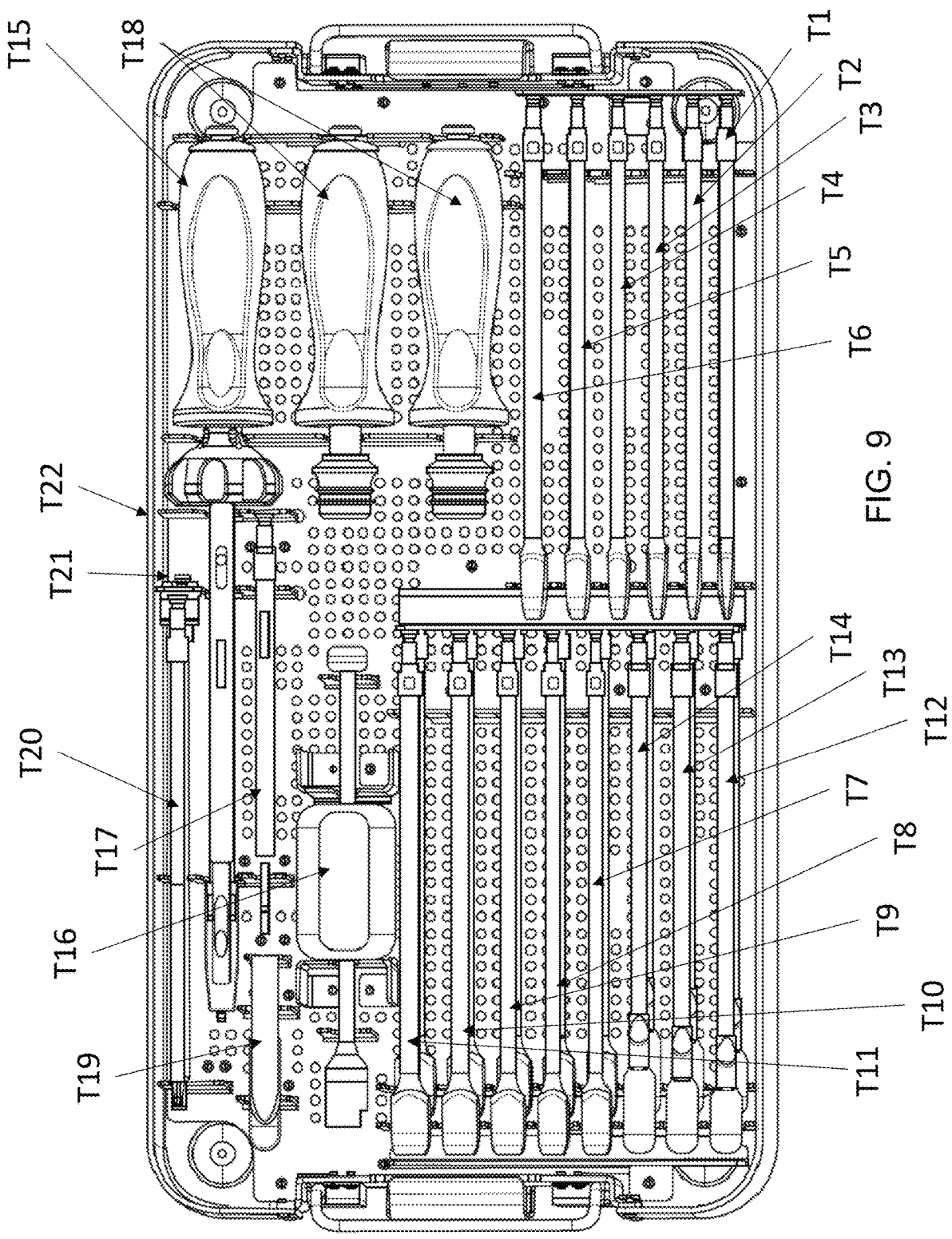
FIG. 9 depicts a top plan view of one embodiment of the surgical instrumentation kit for a total joint replacement spinal implant system procedure.

In various embodiments, an instrumentation kit may be provided which comprises a variety of available tools for use throughout the procedure (as shown in FIG. 9). The at least three length trials may match and/or approximate the lengths of the superior component of the implant. The at least three length trials comprise a short (25 mm), a medium (29 mm), and a long (32 mm). Accordingly, the surgeon may attach the length trial tool to a standard handle known in the art for easier manual manipulation and/or the surgeon may attach the length trial to a custom handle, e.g., the Hudson handle, for easier manual manipulation.

TABLE 2

| Exemplary kit components/tools of FIG. 9. | |
| --- | --- |
| ITEM No. | Description |
| T1 | Distractor, 5 |
| T2 | Distractor, 6 |
| T3 | Distractor, 7 |
| T4 | Distractor, 8 |
| T5 | Distractor, 9 |
| T6 | Distractor, 10 |

TABLE 2-continued

Exemplary kit components/tools of FIG. 9.

| ITEM No. | Description |
|---|---|
| T7 | Height Trial, 11 |
| T8 | Height Trial, 12 |
| T9 | Height Trial, 13 |
| T10 | Height Trial, 14 |
| T11 | Height Trial, 15 |
| T12 | Length Trial, Short |
| T13 | Length Trial, Medium |
| T14 | Length Trial, Long |
| T15 | Inserter |
| T16 | Slap Hammer |
| T17 | Removal Tool |
| T18 | Hudson Handle |
| T19 | Screw Guide |
| T20 | Screwdriver |
| T21 | Removal Driver |
| T22 | Base |
| T23 | Lid (not shown) |
| T24 | IFU (U.S.) (not shown) |

Figures 10A, 10B, 10C:
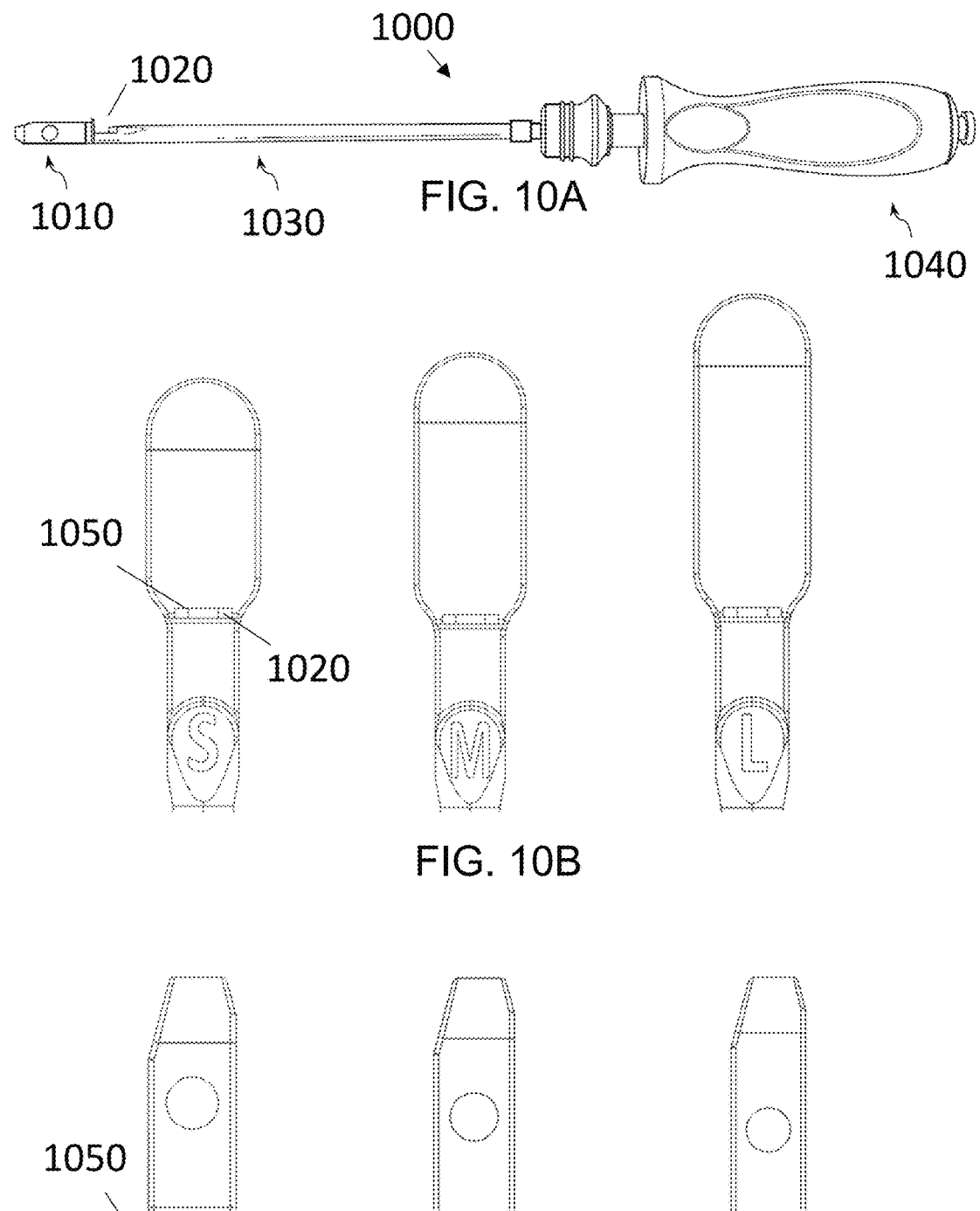
FIGS. 10A-10C depict different views of one embodiment of a length trial.

FIG. 10A depicts a side view of one exemplary embodiment of a length trial 1000, which includes a length trial body 1010, a stop tab 1020, a shaft 1030 and a handle 1040. As best seen in FIGS. 10B and 10C, the stop tab 1020 desirably includes an anterior facing surface 1050 which can engage with a corresponding posterior surface of a superior and/or inferior vertebral body (not shown) when the trial is inserted into a desired position and/or orientation relative to the targeted anatomy. In various embodiments, a method of treatment can include the step of determining a proper implant length, which may comprise the step of introducing at least one length trial on at least one side being the first side and/or a second side. The step of introducing at least one length trial on at least one side can include the steps of: inserting the length trial into the targeted intervertebral disc space; translating the at least one length trial within the targeted intervertebral disc space until reaching the positive stop tab. Alternatively, step of determining the proper implant length can include the steps of: inserting the length trial into the targeted intervertebral disc space; and translating the at least one length trial on at least one side that matches or substantially matches the transverse pedicle angle (or convergence angle) until reaching the positive stop tab 1050 as shown in FIGS. 11B and 11C. While an optimal trial alignment would be substantially parallel to the transverse pedicle angle central axis, in various embodiments a substantially matching length may be determined even if the trial is positioned up to a ±10 percent (and/or ±10 degrees) deviation from the transverse pedicle angle central axis.

An exemplary step of introduction may include translating the length trial along a custom desired path and/or the translating along and/or substantially along the transverse pedicle angle between a distracted disc space. Should the surgeon follow along, match or substantially match the transverse pedicle angle, such alignment, convergence and/or positioning (may also be referred to as a "toe-in angle") could help facilitate stability and/or resist shear forces. The orientation of pedicles, known as the transverse pedicle angles, can vary across each spine segment within a spine region, as well as between the individual pedicles of a single vertebral body. As shown in FIG. 11C, the pedicles tend to converge lateral to medial as spinal levels go up the spine. In various alternative embodiments, a surgeon may elect to not have the length trial match or substantially match the transverse pedicle angle.

With reference to FIGS. 10A-10C, the translation of the length trial within the targeted intervertebral space should be pushed or slid toward the anterior direction of the distracted intervertebral space following a custom path and/or the transverse pedicle angle until the surgeon contacts a portion of the anterior facing surface of a positive stop tab on the at least one length trial onto a portion of the posterior surface of vertebral body and/or a portion of the apophyseal ring. If desired, prior to inserting a trial tool the surgeon should ensure that the exiting nerve root is gently retracted laterally, and the thecal sack should be retracted medially to protect the neural elements if one or both retractions are necessary.

As previously noted, the length trial can comprise a positive stop or a tab that is disposed on the posterior end of the length trial body of the length trial. The positive stop or tab desirably extends upwardly from a top surface of the length trial body. The positive stop or tab extends upwardly and perpendicularly from a top surface of the length trial body. The positive stop or tab extends upwardly and obliquely from a top surface of the length trial body. The stop or tab comprises an anterior facing wall and a posterior facing wall. As the surgeon introduces the length trial into the distracted intervertebral disc space, the surgeon will push the length trial until at least a portion of the anterior facing surface of the tab contacts a portion of the posterior facing surface of the upper and/or lower vertebral body. The stop or tab controls the depth location of length trial as it is intended to rest against the dorsal aspect of the superior apophyseal ring and/or a posterior facing surface of an upper and lower vertebral body.

Figure 11A:
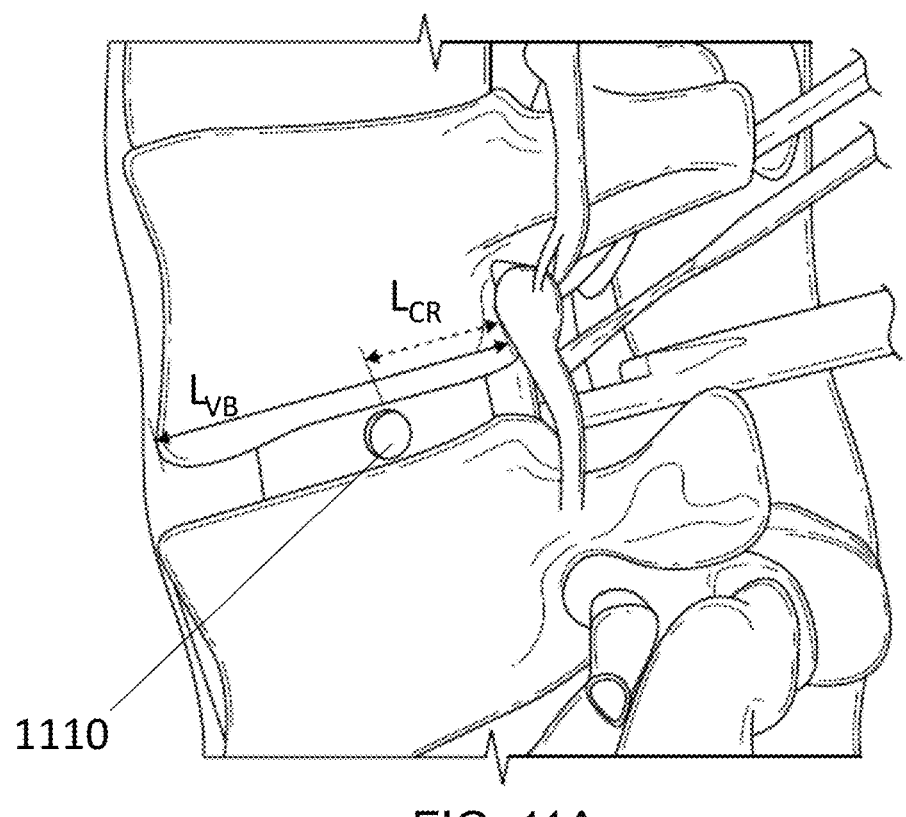
FIGS. 11A-11B depict different views of the length trial within an intravertebral space within a spine region.
Figure 11B:
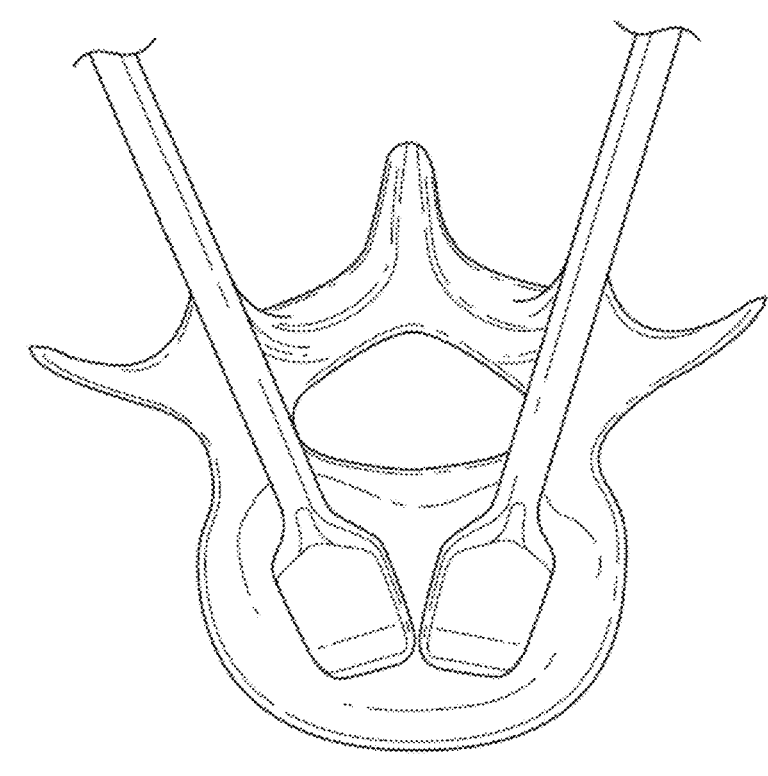
Figure 11C:
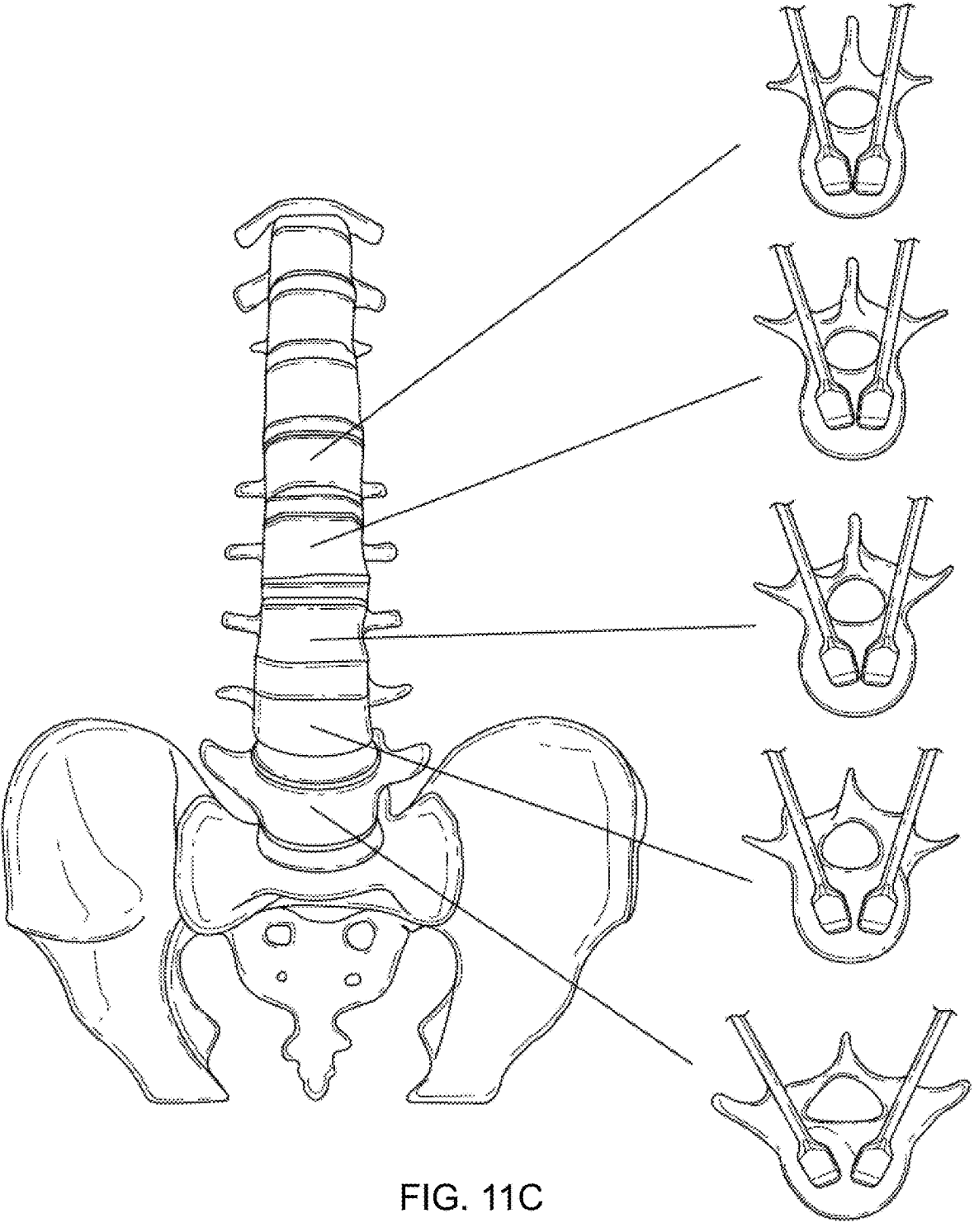
FIG. 11C depicts a top view of a length trial and its angle of convergence in different spine segments.

As another alternative, a step of determining an optimal spinal implant length can comprise the step of confirming the center of rotation (COR) as shown in FIGS. 11A-11C. The surgeon may confirm that the COR is desirably positioned at least 40% anterior from the posterior end of the caudal endplate of the cranial vertebral body. The COR can be confirmed by viewing a radiopaque marker or opening 1110 disposed on the length trial through an imaging technique. The confirmation may be completed subjectively by looking at the radiopaque marker and approximating its position is at least 40% anterior from the posterior end of the caudal endplate of the cranial vertebral body using at least one image. Alternatively, the confirmation may be completed by one or more measurements, the one or more measurements includes the obtaining length of the cranial vertebral body, $L_{VB}$, using at least one image and calculating the center of rotation, $L_{CR}$, by measuring at least 40% anterior from the posterior end of the caudal endplate of the cranial vertebral body. The positioning of the radiolucent marker on the length trial relative to the vertebral body can be intended to approximate the implant's center of rotation.

Once the length trials are positioned, the surgeon may desirably complete the step of confirming proper or approximated spinal implant length by acquiring at least one image using at least one imaging technique. The at least one image technique may comprise an MRI, a radiograph, a CT scan, an ultrasound, and/or any combination thereof. The at least one imaging technique may further comprise 2D or 3D images. While the one or more length trials are in position within the disc space, the surgeon may confirm one or more of the following: the proper tensioning of the soft tissues; the proper implant length; the proper center of rotation (COR) of the implant; the proper convergence angle (e.g., transverse pedicle angle or toe-in angle); the length trials do not contact a portion of the ALL or remaining annulus and/or any combination thereof. Should the proper and/or approximated spinal implant length be unable to be confirmed, the surgeon will use the subsequent length trial tool, and repeat the steps beginning from the step of assembling a length trial tool (using the new length trial).

Figure 12A:
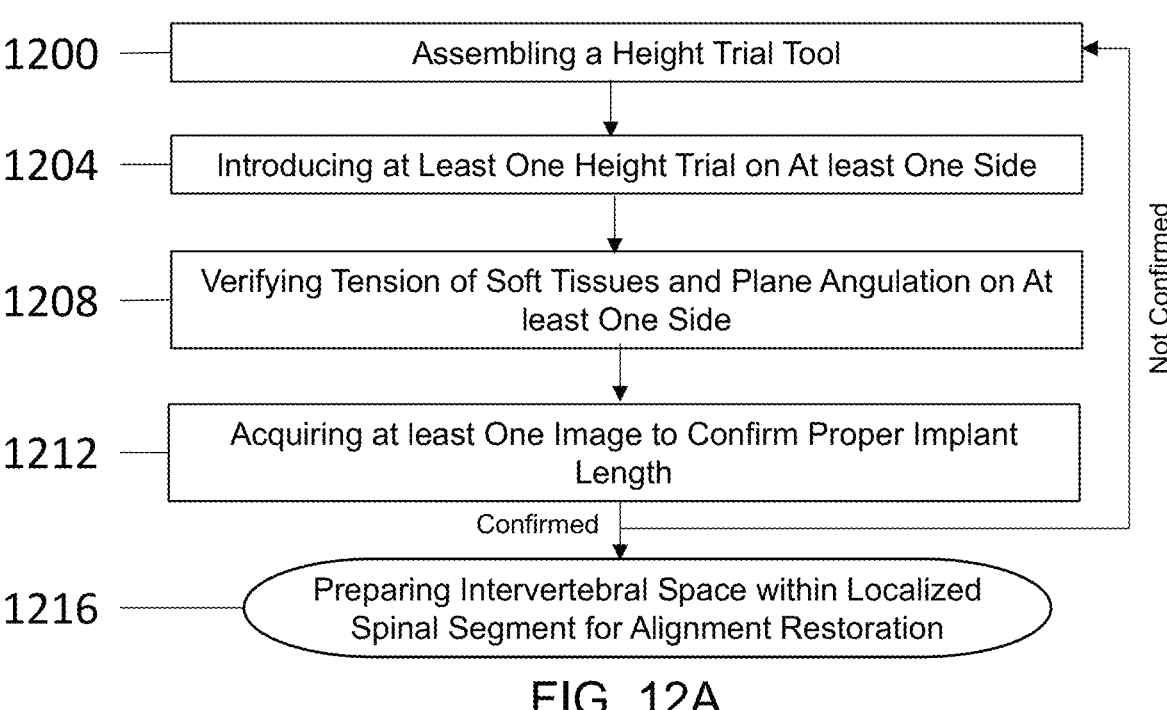

With reference to FIG. 12A, the step of selecting the proper spinal implant size can comprise step for determining the proper spinal implant height. The step of determining the proper or approximated spinal implant height can comprises the steps of: assembling at least one height trial tool 1200; introducing at least one height trial on the at least one side 1204; verifying soft tissue tension and intervertebral space angulation 1208; and confirming proper or approximate spinal implant height by acquiring at least one image using at least one imaging technique 1212.

Figure 12B:
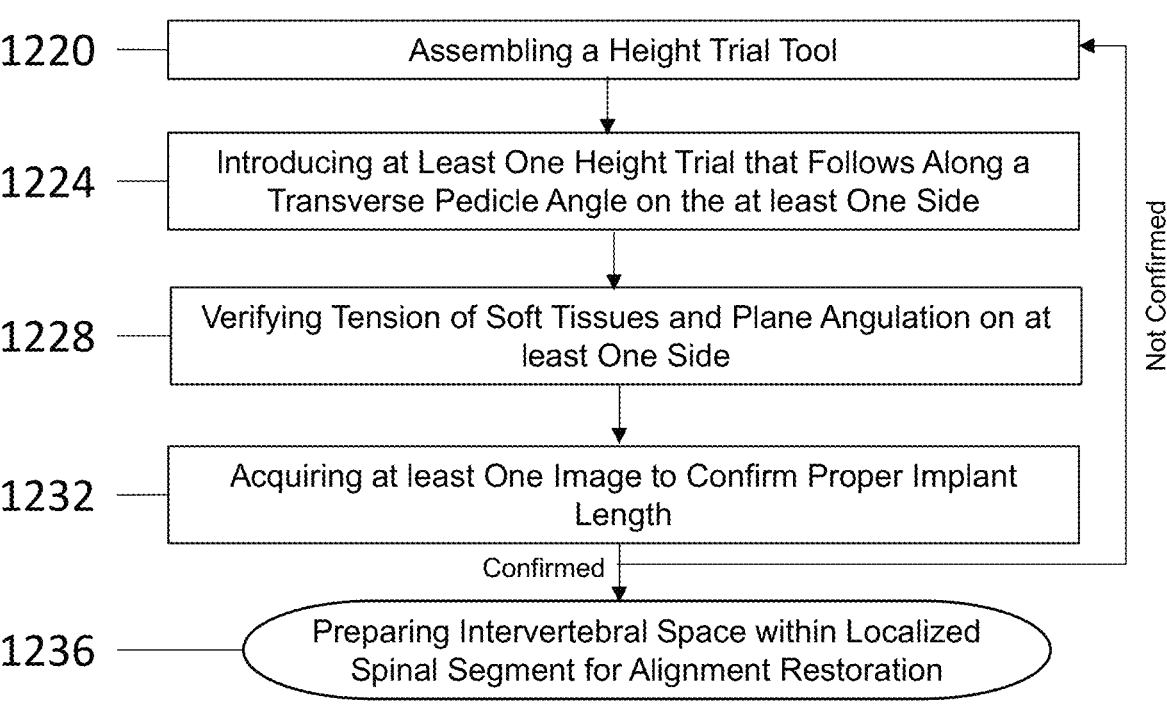

With reference to FIG. 12B, the step of selecting the proper spinal implant size can comprise the step of determining the proper spinal implant height. The step of determining the proper or approximated spinal implant height comprises the steps of: assembling at least one height trial tool 1220; introducing at least one height trial that follows along, matches or substantially matches the transverse pedicle angle on the at least one side 1224; verifying soft tissue tension and intervertebral space angulation on the at least one side 1228; and confirming proper or approximate spinal implant height on the at least one side by acquiring at least one image using at least one imaging technique 1232.

With reference to FIG. 12C, the step of selecting the proper spinal implant size can comprise the step of determining the proper spinal implant height. The step of determining the proper or approximated spinal implant height can comprise the steps of: assembling a first and second height trial tool 1240; introducing a first height trial on a first side and a second height trial tool on a second side 1244; verifying a first soft tissue tension and first intervertebral space angulation on the first side and a second soft tissue tension and second intervertebral space angulation on the second side 1248; and confirming proper or approximate spinal implant height by acquiring at least one image using at least one imaging technique on a first side and a second side 1252. The first height trial may comprise a same height as the second height trial. The first height trial may comprise a different height as the second height trial. The first soft tissue tension may comprise a same tension as the second soft tissue tension. The first soft tissue tension may comprise a different tension as the second soft tissue tension. The first angulation may comprise a same angle as the second angulation. The first angulation may comprise a different angulation.

With reference to FIG. 12D, the step of selecting the proper spinal implant size can comprise the step of determining the proper spinal implant height. The step of determining the proper or approximated spinal implant height may comprise the steps of: assembling a first and second height trial tool 1260; introducing a first height trial tool that follows along, matches or substantially matches a first transverse pedicle angle on a first side and a second height trial tool that follows along, matches or substantially matches a second transverse pedicle angle on a second side 1264; verifying a first soft tissue tension and first intervertebral space angulation on the first side and a second soft tissue tension and second intervertebral space angulation on the second side 1268; and confirming proper or approximate spinal implant height by acquiring at least one image using at least one imaging technique on a first side and a second side 1272. The first height trial may comprise a same height as the second height trial. The first height trial may comprise a different height as the second height trial. The first soft tissue tension may comprise a same tension as the second soft tissue tension. The first soft tissue tension may comprise a different tension as the second soft tissue tension. The first angulation may comprise a same angle as the second angulation. The first angulation may comprise a different angulation. The first transverse pedicle angle may comprise a same angle and the second transverse pedicle angle. The first transverse pedicle angle may comprise a different angle as the second transverse pedicle angle.

Once the implant length is confirmed, the surgeon may desirably complete the step of determining the proper implant height. In one embodiment, the step of determining the proper implant height using implant height trial tools may require the use of sequential height trial tools. The surgeon may confirm that the kit may contain at least three length trials (as shown in FIG. 9). The at least three height trials or more that may match and/or approximate the height of the implant. An exemplary height trial 1300 can include a height trial body 1310, a shaft 1320 and a handle 1330. In one exemplary embodiment, a kit of height trials may comprise trials having differing heights of 11 mm, 12 mm, a 13 mm, a 14 mm and a 15 mm, such as shown in FIGS. 13B and 13C. Accordingly, the surgeon may attach the height trial to a standard handle known in the art for easier manual manipulation and/or the surgeon may attach the height trial to a custom handle, e.g., the Hudson handle, for easier manual manipulation.

In another embodiment, the step of determining the proper implant height may comprise the step of introducing at least one height trial on at least one side, the first side and/or a second side. The step of introducing at least one height trial on at least one side, the first side and/or second side includes the steps of: inserting the height trial into the targeted intervertebral disc space; translating the at least one height trial within the targeted intervertebral disc space. Alternatively, step of determining the proper implant height includes the steps of: inserting the height trial into the targeted intervertebral disc space; and translating the at least one height trial on at least one side that matches or substantially matches the transverse pedicle angle (or convergence angle). Substantially matches may comprise at least up to a +/−10 percent (and/or ±10 degrees) deviation from the transverse pedicle angle central axis.

The step of introduction may include translating the height trial along a custom desired path and/or the translating along and/or substantially along the transverse pedicle angle between a distracted disc space. Should the surgeon follow along, match or substantially match the transverse pedicle angle, such alignment, convergence and/or positioning (may also be referred to as a "toe-in angle") would help facilitate stability and resist shear forces. The orientation of pedicles, known as the transverse pedicle angles, vary across each spine segment within a spine region. As shown in FIG. 11C, the pedicles tend to converge (e.g., lateral to medial) while one moves up the spine. Alternatively, the surgeon may not have the height trial to match or substantially match the transverse pedicle angle.

The step of introduction may include translating the height trial along a custom path and/or follows along or follows substantially along the transverse pedicle angle between a disc space. With reference to FIG. 14, the translation of the length trial within the targeted intervertebral space should desirably be pushed or slid toward the anterior direction of the distracted intervertebral space following a custom path and/or the transverse pedicle angle until the surgeon a portion of the height trial body and/or the entire height trial body is disposed within the interverbal space. Once the height trial is positioned, the surgeon may verify the tension of the soft tissues and the plane angulation. The tension of the soft tissues include verifying that the soft tissues are not over tensioned or excessively tensioned. Also, the plane angulation comprises verifying the angle of the inferior endplate of the superior vertebral body relative to the superior endplate of the inferior vertebral body.

Once the height trials are positioned, the surgeon may complete the step of confirming proper or approximate spinal implant height on the at least one side (e.g., first side and/or second side). The surgeon may desirably acquire at least one image using at least one imaging technique to confirm proper implant height on at least one side, a first side and/or a second side. The at least one image technique may comprise an MRI, a radiograph or X-ray, a CT scan, an ultrasound, and/or any combinations thereof. While the one or more height trials are in position within the disc space, the surgeon may confirm one or more of the following: the proper tensioning of the soft tissues; the proper or approximate implant height; the proper plane angulation of the upper vertebral body relative to the lower vertebral body; the proper convergence angle (e.g., transverse pedicle angle or toe-in angle); the height trials do not contact a portion of the ALL or remaining annulus and/or any combination thereof. The surgeon may mark the medial edge of the height trial for a reference line or a guideline for the step of preparing the intervertebral disc space (e.g., for marking the medial edge of the rasps for the osteotomy). Should the proper and/or approximated spinal implant height is unable to be confirmed, the surgeon will use the subsequent height trial tool, and repeat the steps beginning from the step of assembling a height trial tool (using the new height trial). In another embodiment, the step of determining the proper spinal implant length and the step of determining the proper implant height may be reversed.

With reference to FIG. 15A, an exemplary intraoperative procedure or intraoperative method can comprise the step of preparing the intervertebral space within a localized spinal segment for alignment and motion restoration. The step of preparing the intervertebral space within a localized spinal segment for alignment and motion restoration on at least one side can comprise one or more of the steps of: preparing the caudal vertebral body on the at least one side 1500; preparing the cranial vertebral body on at least one side 1504; completing at least one caudal keel channel on the caudal vertebral body on at least one side 1508; and completing at least one cranial keel channel on the cranial vertebral body on the at least one side and verifying alignment 1512.

With reference to FIG. 15B, an exemplary intraoperative procedure or intraoperative method can comprise the step of preparing the intervertebral space within a localized spinal segment for alignment and motion restoration. The step of preparing the intervertebral space within a localized spinal segment for alignment and motion restoration on at least one side may comprise the steps of: completing a first preparation on the caudal vertebral body on a first side and a second preparation on the caudal vertebral body on a second side 1520; completing a first preparation on a cranial vertebral body on a first side and a second preparation on a second side 1524; completing first caudal keel channel on the caudal vertebral body on a first side and a second caudal keel channel on the caudal vertebral body on a second side 1528; and completing a first cranial keel channel on the cranial vertebral body on the first side and verifying a first keel alignment and a second cranial keel channel on the cranial vertebral body on the second side and verifying a second keel alignment 1532.

With reference to FIG. 15C, an exemplary intraoperative procedure or intraoperative method can comprise the step of preparing the intervertebral space within a localized spinal segment for alignment and motion restoration. The step of preparing the intervertebral space within a localized spinal segment for alignment and motion restoration on a first side and a second side may comprise one or more of the steps of: completing a first preparation on the caudal vertebral body on a first side 1540; completing a first preparation on a cranial vertebral body on a first side 1544; completing first caudal keel channel on the caudal vertebral body on a first side 1548; and completing a first cranial keel channel on the cranial vertebral body on the first side and verifying a first keel alignment 1552; implanting a first spinal implant on a first side 1556; completing a second preparation on the caudal vertebral body on a second side 1560; completing a second preparation on a cranial vertebral body on a second side 1564; completing a second caudal keel channel on the caudal vertebral body on a second side 1568; completing a second cranial keel channel on the cranial vertebral body on the second side and verifying a second keel alignment 1572; and implanting a second spinal implant on a second side 1576.

The first preparation on the caudal vertebral body on the first side may be the same and/or similar to the second preparation on the caudal vertebral body on the second side. The first preparation on the caudal vertebral body on the first side may be different than the second preparation on the caudal vertebral body on the second side. The first preparation on the cranial vertebral body on the first side may be the same as the second preparation on the cranial vertebral body on the second side. The first preparation on the cranial vertebral body on the first side may be different than the second preparation on the cranial vertebral body on the second side. The first spinal implant may be the same size as the second spinal implant. The first spinal implant may be a different size than the second spinal implant.

With reference to FIG. 16A, the step of preparing an intervertebral space within a localized spinal segment for alignment and motion restoration comprises the step of preparing a caudal vertebral body on one side. The step of preparing a caudal vertebral body on at least one side comprises the steps of: obtaining the angle of correction for optimal alignment (e.g., sagittal and/or coronal alignment) from the preoperative method or procedure 1603; introducing the preparation tool on at least one side 1606; preparing a portion of an endplate and a pedicle on a caudal vertebral body on at least one side to create resected surface that matches or substantially matches the preoperative angle of correction for optimal alignment 1609; and confirming the angle correction by acquiring at least one image using at least one imaging technique 1612. The angle of correction comprises a sagittal angle of correction and/or a coronal angle of correction.

With reference to FIG. 16B, the step of preparing an intervertebral space within a localized spinal segment for alignment and motion restoration comprises the step of preparing a caudal vertebral body on one side. The step of preparing a caudal vertebral body on at least one side comprises the steps of: obtaining the angle of correction for optimal alignment (e.g., sagittal and/or coronal alignment) from the preoperative method or procedure 1618; introducing the preparation tool that follows along, matches or substantially matches a transverse pedicle angle on at least one side 1621; preparing a portion of an endplate and a pedicle on a caudal vertebral body on at least one side to create resected surface that matches or substantially matches the preoperative angle of correction for optimal alignment and follows along, matches and/or substantially matches a transverse pedicle angle 1624; and confirming the angle correction the at least one side by acquiring at least one image using at least one imaging technique 1627. The angle of correction comprises a sagittal angle of correction and/or a coronal angle of correction.

With reference to FIG. 16C, the step of preparing an intervertebral space within a localized spinal segment for alignment and motion restoration comprises the step of preparing a caudal vertebral body on a first and second side. The step of preparing a caudal vertebral body on first and second side comprises the steps of: obtaining a first angle of correction for optimal alignment (e.g., sagittal and/or coronal alignment) and a second angle of correction for optimal alignment from the preoperative method or procedure 1633; introducing a first preparation tool on a first side and a second preparation tool on a second side 1636; completing a first preparation on a portion of an endplate and a pedicle on a caudal vertebral body on a first side to create a first resected surface that matches or substantially matches the first preoperative angle of correction for optimal alignment and a second preparation on a portion of an endplate and a pedicle on the caudal vertebral body on a second side to create a second resected surface that matches or substantially matches the second preoperative angle of correction for optimal alignment 1639; and confirming the first and second angle correction by acquiring at least one image using at least one imaging technique 1642.

With reference to FIG. 16D, the step of preparing an intervertebral space within a localized spinal segment for alignment and motion restoration comprises the step of preparing a caudal vertebral body on a first and second side. The step of preparing a caudal vertebral body on first and second side comprises the steps of: obtaining a first angle of correction for optimal alignment (e.g., sagittal and/or coronal alignment) and a second angle of correction for optimal alignment from the preoperative method or procedure 1648; introducing a first preparation tool on a first side and a second preparation tool on a second side 1651; completing a first preparation on a portion of an endplate and a pedicle on a caudal vertebral body on a first side to create a first resected surface that matches or substantially matches the first preoperative angle of correction for optimal alignment and follows along, matches or substantially matches a first transverse pedicle angle and a second preparation on a portion of an endplate and a pedicle on the caudal vertebral body on a second side to create a second resected surface that matches or substantially matches the second preoperative angle of correction for optimal alignment and follows along, matches or substantially matches the second transverse pedicle angle 1654; and confirming the first and second angle correction by acquiring at least one image using at least one imaging technique 1657.

With reference to FIG. 16E, the step of preparing an intervertebral space within a localized spinal segment for alignment and motion restoration comprises the step of preparing a caudal vertebral body on a first and second side. The step of preparing a caudal vertebral body on first and second side comprises the steps of: obtaining a first angle of correction for optimal alignment (e.g., sagittal and/or coronal alignment) from the preoperative method or procedure; introducing a first preparation tool on a first side 1666; completing a first preparation on a portion of an endplate and a pedicle on a caudal vertebral body on a first side to create a first resected surface that matches or substantially matches the first preoperative angle of correction for optimal alignment and follows along, matches or substantially matches a first transverse pedicle angle 1672; and confirming the first and second angle correction by acquiring at least one image using at least one imaging technique 1675. With this embodiment, the surgeon should proceed with all of the remaining steps of preparing the intervertebral space within a localized spinal segment for alignment and motion restoration for a first side prior to completing the steps for a second side. The remaining steps include step of preparing an intervertebral space within a localized spinal segment for alignment and motion restoration for a first side; implanting a first spinal implant on a first side; preparing an intervertebral space within a localized spinal segment for alignment and motion restoration for a second side; and implanting a second spinal implant on a second side.

The first preparation on the caudal vertebral body on the first side may be the same as the second preparation on the caudal vertebral body on the second side. The first preparation on the caudal vertebral body on the first side may be different than the second preparation on the caudal vertebral body on the second side. The first spinal implant may be the same size as the second spinal implant. The first spinal implant may be a different size than the second spinal implant. The first angle of correction may comprise the same angle as the second angle of correction. The first angle of correction may comprise a different angle than the second angle of correction. The first transverse pedicle angle may comprise a same transverse angle as the second transverse pedicle angle. The first transverse pedicle angle may comprise a different transverse angle than the second transverse pedicle angle. The first and/or second angle of correction comprises a sagittal angle of correction and/or a coronal angle of correction.

In one embodiment, the step of preparing the caudal vertebral body comprises the step of obtaining an angle of correction, a first angle of correction and/or a second angle of correction for optimal alignment (e.g., sagittal and/or coronal alignment) from the preoperative method or procedure. The one or more preoperative images acquired using at least one imaging technique was used to determine the angle of correction to meet a patient's alignment and motion restoration goals. The angle of correction may comprise a sagittal angle of correction and/or a coronal angle of correction. The angle of correction comprises an angle of 0 degrees to 40 degrees. The angle of correction may be different in different spine regions.

In another embodiment, the step of preparing the caudal vertebral body comprises the step of introducing a preparation tool on at least one side, a first side and/or a second side. The step of introducing a preparation tool on at least one side, a first side and/or a second side comprises the steps of assembling the preparation tool; distracting the intervertebral disc space of a localized spine segment within a spine region; and inserting the preparation tool into the localized intervertebral space.

The step of assembling the preparation tool may comprise assembling a rasp, a manual handle, and/or a powered handle system. The surgeon may prepare the endplates and/or pedicles manually and/or using a powered system. In one embodiment, the surgeon may use a powered system comprising a powered reciprocating system, a powered handle or handpiece, and a rasp. The rasp may comprise a long or short and flat rasp. To use the powered reciprocating system, the surgeon should connect the cables and cord into an outlet allowing the powered reciprocating system to activate. The surgeon may subsequently insert a rasp into an unlocked powered handpiece and twist the locking collar on the handpiece to lock the rasp into the handpiece. The surgeon may test the powered system by stepping on the footswitch. The pressure on the footswitch determines the variable speed to activate and/or reciprocate the rasp.

The step of distracting an intervertebral disc space of a localized spine segment within a spine region may require a surgeon to distract the interverbal disc space on at least one side, a first side and/or a second side. The surgeon should distract the at least one side (e.g., a first side and/or a second side) by using a height trial. The height trial may optionally comprise at least 1 mm larger or taller than the height trial determined at the step of determining the proper implant height. Maintaining the at least one side, a first side and/or a second side using a height trial that is at least 1 mm greater than determined implant height from the previous step can provide extra tension on the tissues and increase the intervertebral disc space for easier endplate preparation and the completion of the osteotomy of the pedicles.

The step of inserting a preparation tool into the localized intervertebral space may require the surgeon to introduce or insert the inactivated powered rasp into the distracted intervertebral disc space on the native caudal vertebral body into the at least one side, a first side and/or a second side along a desired path. Alternatively, the desired path may be a custom path and/or follow along, match or substantially match the pedicle transverse angle (or pedicle axis) on the at least one side, a first side and/or a second side within a distracted intervertebral dis space. The rasp may comprise a long, flat rasp and/or a short, flat rasp. The surgeon should confirm placement and/or positioning of the preparation tools by acquiring at least one image with at least one imaging technique on the native caudal endplate surface and/or pedicle surface. The surgeon may refer or obtain the pre-operative measurements, the preoperative measurements include the optimal sagittal and/or coronal angle of correction.

In another embodiment, the step of preparing the caudal vertebral body can comprise a step of completing at least one preparation on at least one side. The preparation may comprise the step of completing an osteotomy within the disc space of a localized spine segment. The step of completing an osteotomy within a disc space of a localized spine segment is a corrective osteotomy to restore sagittal and/or coronal balance, along with maximizing implant range of motion or motion restoration. The osteotomy will desirably result in the creation of parallel endplates for neutral insertion of the implant. The degree of osteotomy and/or the angle of correction (AOC) that is necessary is generally the angle to create parallel cranial and caudal prepared endplates at the index vertebral segment level and as determined in preoperative (or intraoperative if using navigation) planning and confirmed intraoperatively.

Figure 17A:
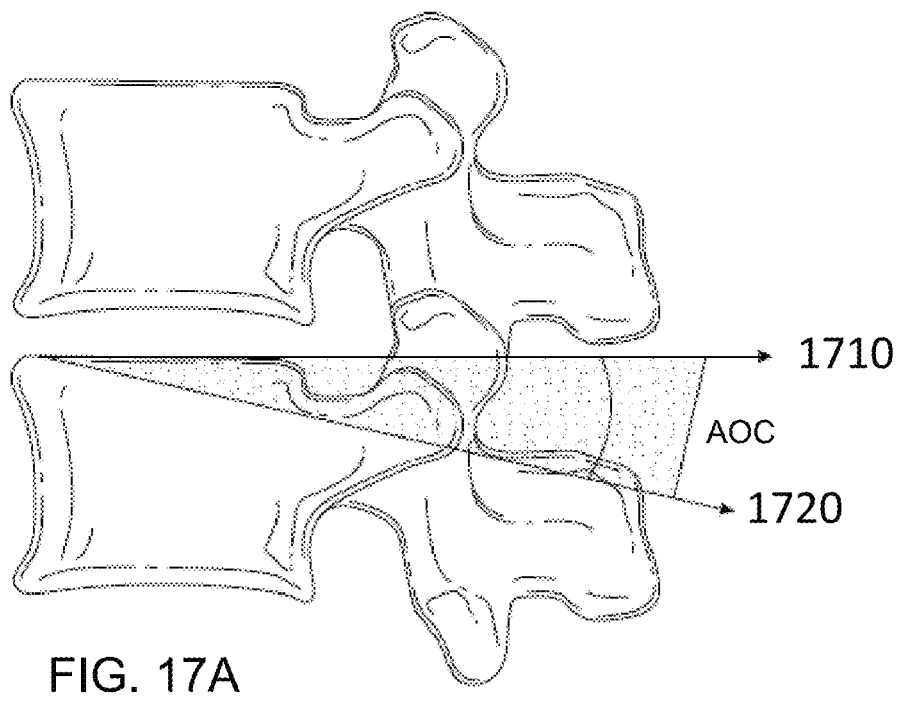
FIGS. 17A-17B depicts a sagittal view of one embodiment of a prepared caudal vertebral body.
Figure 17B:
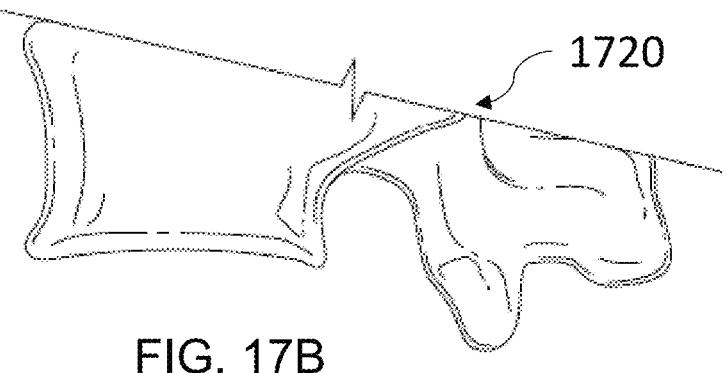

FIGS. 17A-17B depict one exemplary embodiment of a preparation of a superior endplate and pedicle of a lower or caudal vertebral body, where the native endplate and pedicle has a first angulation 1710 and the surgeon can prepare a resected endplate and pedicle surface at a second angulation 1720, which may the same or different than the first angulation 1710. The AOC is obtained for at least one side, a first side and/or a second side from the preoperative method or steps discussed herein. The AOC can guide the surgeon in preparing the caudal vertebral body to match or substantially match to a desired position and/or angulation, which in some embodiments may be the same or different that the pre-operative AOC measurement. The AOC measurement can comprise a coronal and/or a sagittal angle, each of the angles include 0 degrees to 40 degrees. The surgeon may activate the powered rasp that is disposed onto the native endplate surface by pressing on the footswitch—where a light pressure equals a slow reciprocating speed, and a hard pressure equals a faster reciprocating speed. The surgeon prepares at least a portion of the superior endplate on the caudal vertebral body by utilizing the flat reciprocating rasp at a desired speed until the posterior aspect is flush with the vertebral body and a slight bleeding is observed to facilitate bony ingrowth to the spinal implant after deployment to create a first resected surface. Alternatively, the surgeon may prepare at least a portion of the superior endplate on the caudal vertebral body following along, matching or substantially matching the pedicle transverse angle (e.g., the pedicle axis) utilizing the long, flat rasp as a desired speed until the posterior aspect is flush with the vertebral body and a slight bleeding is observed to facilitate bony ingrowth to the spinal implant after deployment to create a first resected surface. The transverse pedicle angle may include 0 degrees to 45 degrees. Accordingly, the surgeon may prepare at least a portion of the superior endplate of the caudal vertebral body to comprise a first resected shape, a first resected length, a first resected width and a first resected depth.

The first resected surface may comprise a flat, planar plane or surface and/or be parallel to the native endplate surface. The first resected surface may comprise an angle, the angles may comprise 0 degrees to 40 degrees. The angles may comprise a sagittal angle, a coronal angle, a transverse pedicle angle (e.g., a convergence angle), and/or any combination thereof. The angles of the first resected surface may be angled relative to the native endplate plane. The first resected surface may be below and parallel relative to the native endplate plane. The first resected surface may be below and angled relative to the native endplate plane. The first resected surface may comprise a flat and angled surface. Alternatively, the angle of the first resected surface may match or substantially match the angle of correction of the optimal sagittal and/or coronal resection plane. The angle of the first resected surface may match or substantially match the transverse pedicle angle. The first resected surface may comprise a resected shape, first resected length and first resected width may match or substantially match the shape, length and width of the spinal implant.

The surgeon may begin the step of removing or resecting a portion of at least one pedicle on at least one side of the caudal vertebral body to create a second resected surface. The second resected surface may comprise a flat, planar plane or surface and/or parallel to the native pedicle surface. The second resected surface may comprise an angle, the angle may comprise 0 degrees to 40 degrees. The angles may comprise a sagittal angle, a coronal angle, a transverse pedicle angle (e.g., a convergence angle) and/or any combination thereof. The angle of the second resected surface is angled relative to the native pedicle surface or plane. The second resected surface may be below and parallel relative the native pedicle surface. The second resected surface may be below and angled relative to the native pedicle surface. The second resected surface may comprise a flat and angled surface. The second resected surface may comprise a resected shape, a second resected length, a second resected width of the spinal implant. Furthermore, the angle of the second resected surface may match or substantially match the angle of correction of the optimal sagittal and/or coronal resection plane obtained from the preoperative procedure.

The first resected surface may be continuous with the second resected surface. Alternatively, the first resected surface may not be continuous with the second resected surface. A first angle of the first resected surface may comprise the same angle as a second angle of the second resected surface. Alternatively, the first angle of the first resected surface may comprise a different angle as a second angle of the second resected surface. Also, each of the first resected shape, the first resected length, the first resected width and/or the first resected depth may comprise the same as each of the second resected shape, the second resected length, the second resected width, and/or the second resected depth. Alternatively, each of the first resected shape, the first resected length, the first resected width and/or the first resected depth may comprise a different each of the second resected shape, the second resected length, the second resected width, and/or the second resected depth.

In another embodiment, the step of preparing at least a portion of the superior endplate of a caudal vertebral body and the removing or resecting a portion of at least one pedicle on at least one side may comprise a continuous, single resected surface. The surgeon prepares at least a portion of the superior endplate and the pedicle on the caudal vertebral body by utilizing the flat reciprocating rasp at a desired speed until the posterior aspect is flush with the vertebral body and a slight bleeding is observed to facilitate bony ingrowth to the spinal implant after deployment to create a resected surface. Alternatively, the surgeon may prepare at least a portion of the superior endplate and the pedicle on the caudal vertebral body by following along, matching or substantially matching the pedicle transverse angle (e.g., the pedicle axis) while utilizing the long, flat rasp as a desired speed until the posterior aspect is flush with the vertebral body and a slight bleeding is observed to facilitate bony ingrowth to the spinal implant after deployment to create a resected surface. The transverse pedicle angle may include 0 degrees to 45 degrees.

The resected surface may extend from a portion of the superior endplate to a portion of the pedicle on the caudal vertebral body. The resected surface may comprise resected shape, a resected length, a resected width and a resected depth. The resected surface length and/or the resected width may match at least a portion of the spinal implant length and/or width. The resected surface may be positioned or created at an angle. The angle of the resected surface may match or substantially match the pre-determined AOC from pre-procedure step. The angle may comprise a sagittal angle, a coronal angle, a transverse pedicle angle (e.g., convergence angle), and/or any combination thereof.

The angle may comprise 0 degrees to 40 degrees. The angle of the resected surface may be angled relative to the native endplate plane and/or surface. The resected surface may be below and parallel relative to the native endplate plane or surface. The resected surface may be below and angled relative to the native endplate plane or surface. The resected surface may comprise a flat and angled surface. The angle of the resected surface may match or substantially match the pedicle transverse angle. Alternatively, the resected surface may be positioned straight or an angle that does not match or substantially match the transverse pedicle angle. Alternatively, the first resected surface may match or substantially match the angle of correction of the optimal sagittal and/or coronal resection plane. The first resected shape, first resected length and first resected width may match or substantially match the shape, length and width of the spinal implant.

Furthermore, step of preparing the caudal vertebral body on the at least one side, first side and/or second side, may include the step of acquiring at least image using an imaging technique on at least one side, a first side and/or a second side to confirm the angle and/or the angle of correction of the resected surface, the first resected surface and/or the second resected surface by acquiring at least one image using at least one imaging technique. The surgeon may verify that the angle of the resected surface, the first resected surface and/or second resected surface by comparing it to the realignment resection plane measured during the pre-operative planning procedures for restoration or substantial restoration of a patient's coronal and/or sagittal alignment. The at least one image may be performed by using at least one imaging technique. The imaging techniques may comprise 2D or 3D images. The imaging techniques may comprise an MRI, a radiograph, a CT scan, an ultrasound, and/or any combination thereof. The preparation of the endplate surface and pedicle surface of caudal vertebral body on the contralateral side may be performed by repeating the above steps.

Figure 18A:
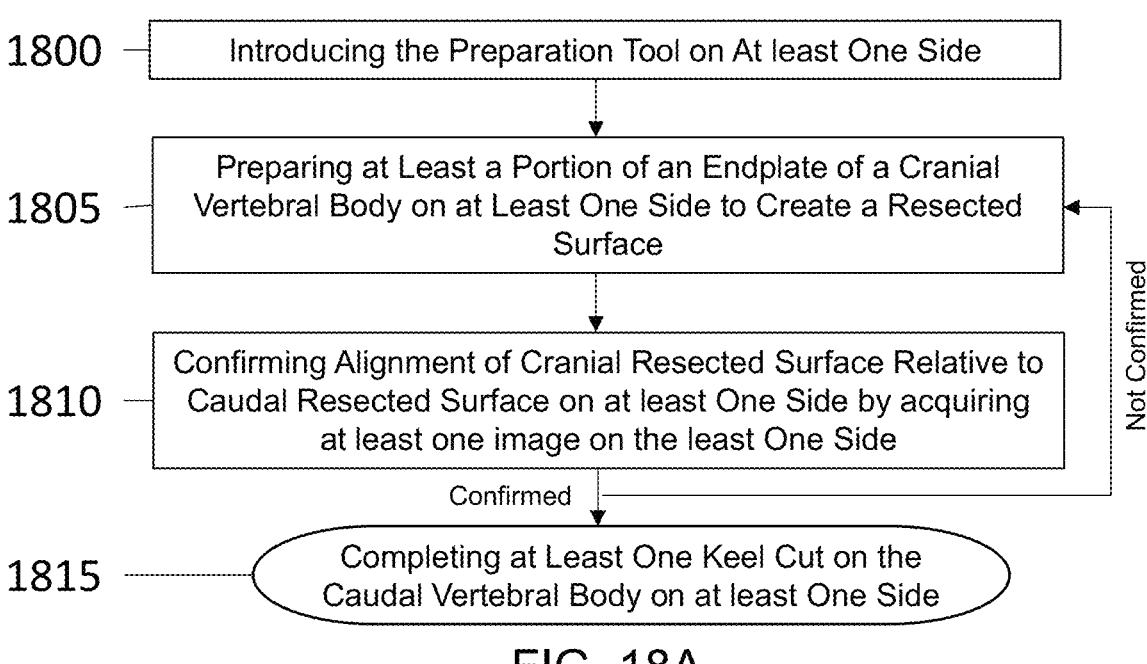

With reference to FIG. 18A, the step of preparing the targeted intervertebral space within a localized spine segment for alignment and motion restoration comprises a step preparing the cranial vertebral body on at least one side. The step of preparing a cranial vertebral body on at least one side comprises the steps of: obtaining the angle of correction for optimal alignment (e.g., sagittal and/or coronal alignment); introducing the preparation tool on at least one side 1800; preparing a portion of an endplate on a cranial vertebral body on at least one side to create resected or prepared surface that matches or substantially matches the preoperative angle of correction for optimal alignment 1805; and confirming the angle correction by acquiring at least one image using at least one imaging technique 1810. The angle of correction comprises a sagittal angle of correction and/or a coronal angle of correction.

Figure 18B:
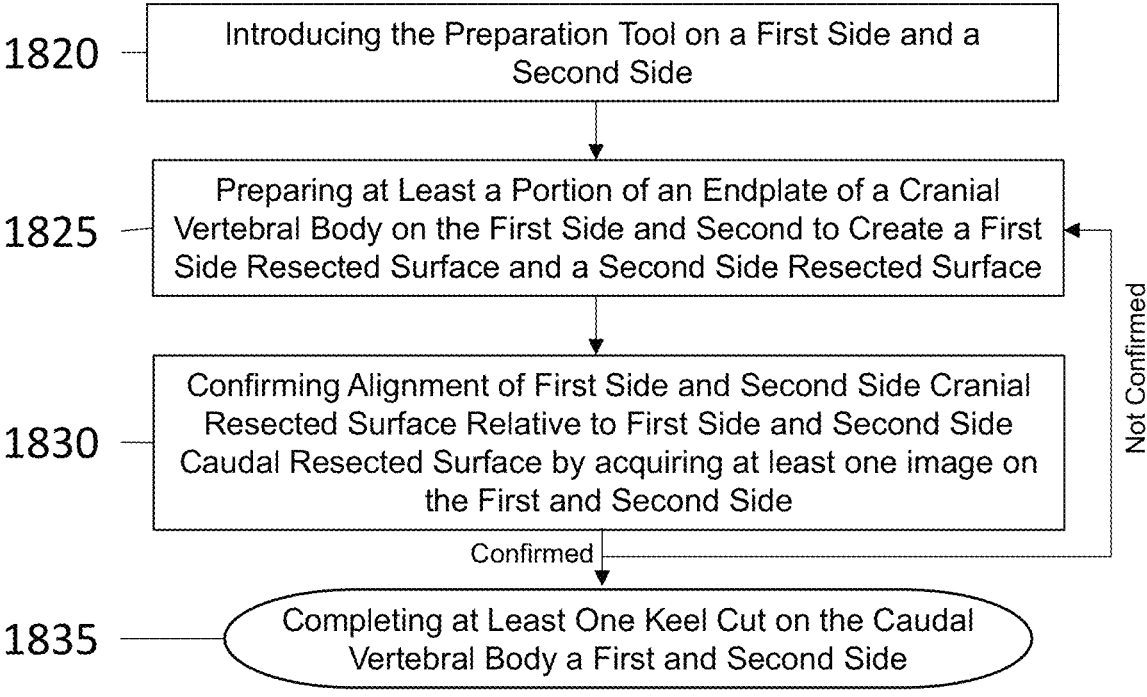

With reference to FIG. 18B, the step of preparing an intervertebral space within a localized spinal segment for alignment and motion restoration comprises the step of preparing a cranial vertebral body on one side. The step of preparing a cranial vertebral body on at least one side comprises the steps of: obtaining the angle of correction for optimal alignment (e.g., sagittal and/or coronal alignment) from the preoperative method or procedure; introducing the preparation tool within a disc space on at least one side 1820; preparing a portion of an endplate on a cranial vertebral body on at least one side to create resected or prepared surface that matches or substantially matches the preoperative angle of correction for optimal alignment and follows along, matches and/or substantially matches a transverse pedicle angle 1825; and confirming the angle correction the at least one side by acquiring at least one image using at least one imaging technique 1830. The angle of correction comprises a sagittal angle of correction and/or a coronal angle of correction.

With reference to FIG. 18C, the step of preparing an intervertebral space within a localized spinal segment for alignment and motion restoration comprises the step of preparing a cranial vertebral body on a first and second side. The step of preparing a cranial vertebral body on first and second side comprises the steps of: obtaining a first angle of correction for optimal alignment (e.g., sagittal and/or coronal alignment) and a second angle of correction for optimal alignment from the preoperative method or procedure 1840; introducing a first preparation tool on a first side and a second preparation tool on a second side 1845; completing a first preparation on a portion of an endplate on a cranial vertebral body on a first side to create a first resected or prepared surface that matches or substantially matches the first preoperative angle of correction for optimal alignment and a second preparation on a portion of an endplate and a pedicle on the caudal vertebral body on a second side to create a second resected or prepared surface that matches or substantially matches the second preoperative angle of correction for optimal alignment 1850; and confirming the first and second angle correction by acquiring at least one image using at least one imaging technique 1855.

Figure 18D:
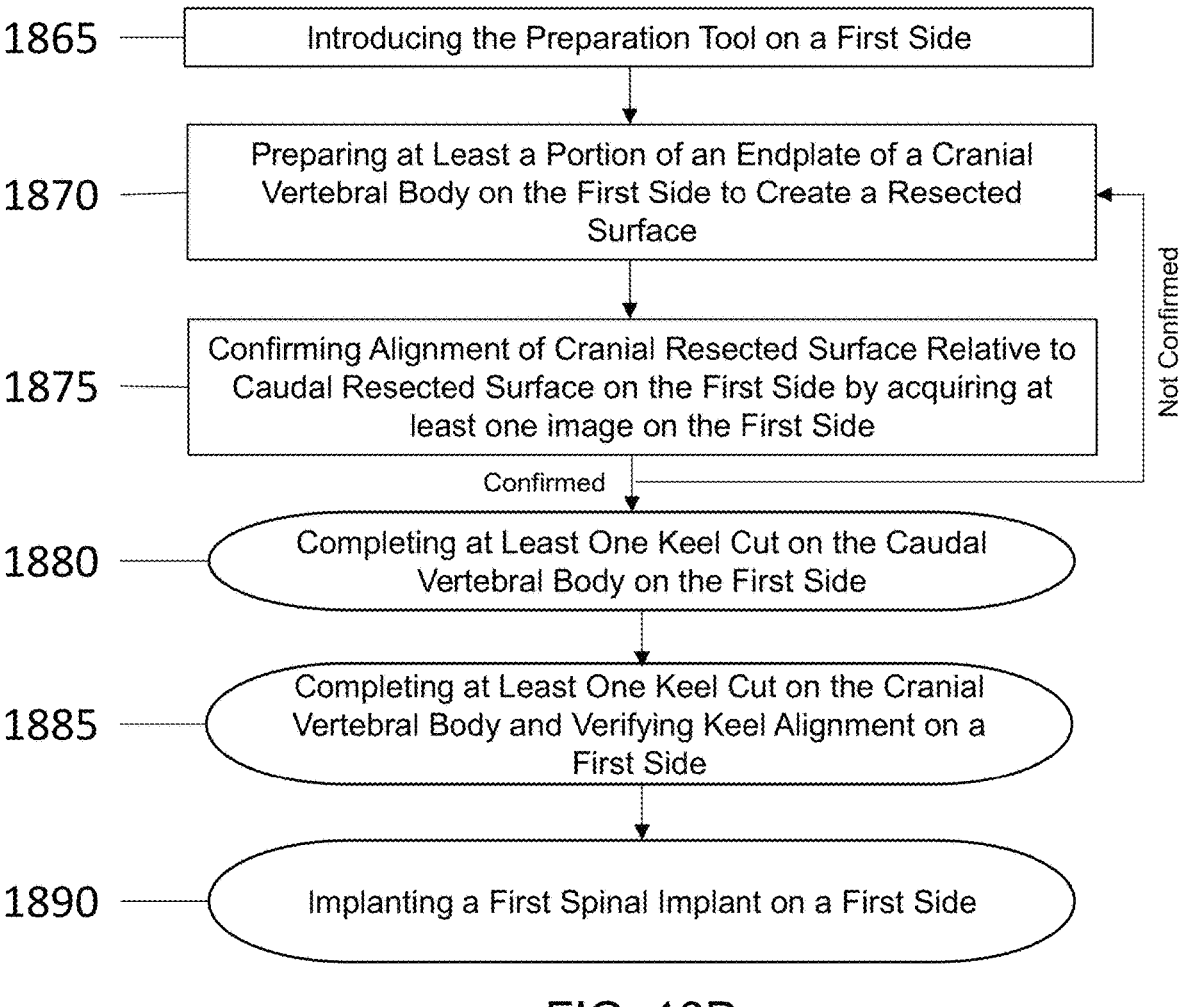

With reference to FIG. 18D, the step of preparing an intervertebral space within a localized spinal segment for alignment and motion restoration comprises the step of preparing a cranial vertebral body on a first and second side. The step of preparing a cranial vertebral body on first and second side comprises the steps of: obtaining a first angle of correction for optimal alignment (e.g., sagittal and/or coronal alignment) from the preoperative method or procedure; introducing a first preparation tool on a first side 1865; completing a first preparation on a portion of an endplate on a cranial vertebral body on a first side to create a first resected or prepared surface that matches or substantially matches the first preoperative angle of correction for optimal alignment and follows along, matches or substantially matches a first transverse pedicle angle 1970; and confirming the first and second angle correction by acquiring at least one image using at least one imaging technique 1875. With this embodiment, the surgeon should proceed with all of the remaining steps of preparing the intervertebral space within a localized spinal segment for alignment and motion restoration for a first side prior to completing the steps for a second side. The remaining steps can include one of more of the following: the step of preparing an intervertebral space within a localized spinal segment for alignment and motion restoration for a first side; implanting a first spinal implant on a first side; preparing an intervertebral space within a localized spinal segment for alignment and motion restoration for a second side; and implanting a second spinal implant on a second side.

The first preparation on the cranial vertebral body on the first side may be the same as the second preparation on the cranial vertebral body on the second side. The first preparation on the cranial vertebral body on the first side may be different than the second preparation on the cranial vertebral body on the second side. The first spinal implant may be the same size as the second spinal implant. The first spinal implant may be a different size than the second spinal implant. The first angle of correction may comprise the same angle as the second angle of correction. The first angle of correction may comprise a different angle than the second angle of correction. The first transverse pedicle angle may comprise a same transverse angle as the second transverse pedicle angle. The first transverse pedicle angle may comprise a different transverse angle than the second transverse pedicle angle. The first and/or second transverse pedicle angle may comprise an angle of 0 to 45 degrees. The first and/or second angle of correction comprises a sagittal angle of correction and/or a coronal angle of correction.

In one embodiment, the step of preparing the cranial vertebral body comprises the step of obtaining an angle of correction, a first angle of correction and/or a second angle of correction for optimal alignment (e.g., sagittal and/or coronal alignment) from the preoperative method or procedure. The one or more preoperative images acquired using at least one imaging technique was used to determine the angle of correction to meet a patient's alignment and motion restoration goals. The angle of correction may comprise a sagittal angle of correction and/or a coronal angle of correction. The angle of correction comprises an angle of 0 degrees to 40 degrees. The angle of correction may be different in different spine regions.

In another embodiment, the step of preparing the cranial vertebral body comprises the step of introducing a preparation tool on at least one side, a first side and/or a second side. The step of introducing a preparation tool on at least one side, a first side and/or a second side comprises the steps of assembling the preparation tool; distracting the intervertebral disc space of a localized spine segment within a spine region; and inserting the preparation tool into the localized intervertebral space.

The step of assembling the preparation tool comprises a rasp, a manual handle, and/or a powered handle system. The surgeon may prepare the endplates and/or pedicles manually and/or using a powered system. In one embodiment, the surgeon may use a powered system. The powered system comprises a powered reciprocating system, a powered handle or handpiece, and a rasp. The rasp may comprise a long or short and flat rasp. To use the powered reciprocating system, the surgeon should connect the cables and cord into an outlet allowing the powered reciprocating system to activate. The surgeon may subsequently insert a rasp into an unlocked powered handpiece and twist the locking collar on the handpiece to lock the rasp into the handpiece. The surgeon may test the powered system by stepping on the footswitch. The pressure on the footswitch determines the variable speed to activate and/or reciprocate the rasp.

The step of distracting the intervertebral disc space of a localized spine segment within a spine region requires the surgeon to distract the interverbal disc space on at least one side, a first side and/or a second side. The surgeon should over distract the at least one side, a first side and/or a second side by using a height trial. The height trial should comprise at least 1 mm larger or taller than the height trial determined at the step of determining the proper implant height. Maintaining the at least one side, a first side and/or a second side using a height trial that is at least 1 mm greater than determined implant height from the previous step will provide extra tension on the tissues and increase the intervertebral disc space for easier endplate preparation and the completion of the osteotomy of the pedicles. This distraction should be maintained when transitioning from the step of preparing the caudal vertebral body to the step of preparing the cranial vertebral body. No further distraction may be necessary if the distraction was maintained from the previous step. This step may be omitted.

The step of inserting the preparation tool into the localized intervertebral space may require the surgeon to introduce or insert the inactivated powered rasp into the distracted intervertebral disc space on the native cranial vertebral body into the at least one side, a first side and/or a second side along a desired path. Alternatively, the desired path may be a custom path and/or follow along, match or substantially match the pedicle transverse angle (or pedicle axis) on the at least one side, a first side and/or a second side within a distracted intervertebral dis space. The rasp comprises a long, flat rasp and/or a short, flat rasp. The surgeon should confirm placement and/or positioning of the preparation tool by acquiring at least one image with at least one imaging technique on the native cranial endplate surface. The surgeon may refer or obtain the pre-operative measurements, the preoperative measurements include the optimal sagittal and/or coronal angle of correction.

Figure 19A:
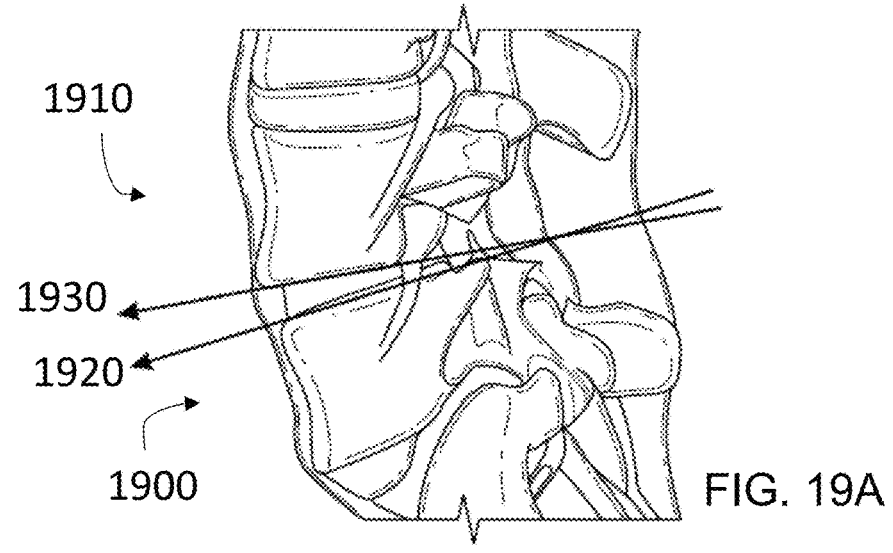
FIGS. 19A-19C depicts a sagittal view of the prepared intravertebral space.
Figure 19B:
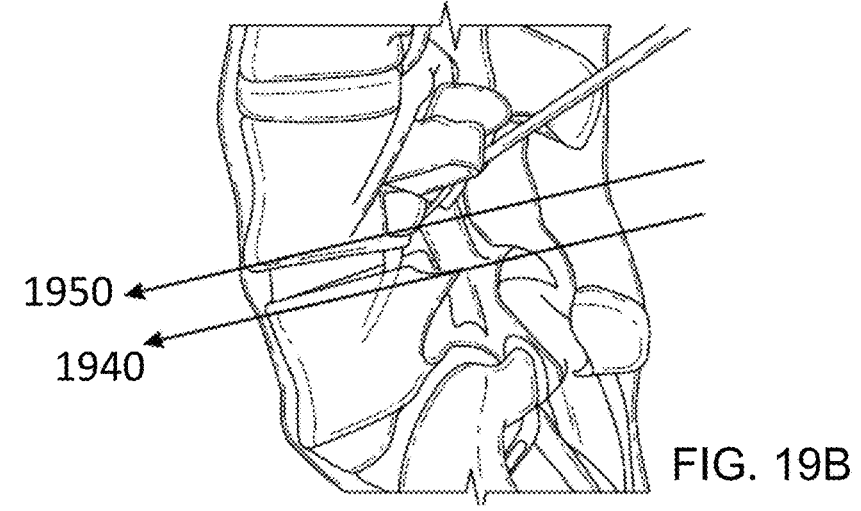
Figure 19C:
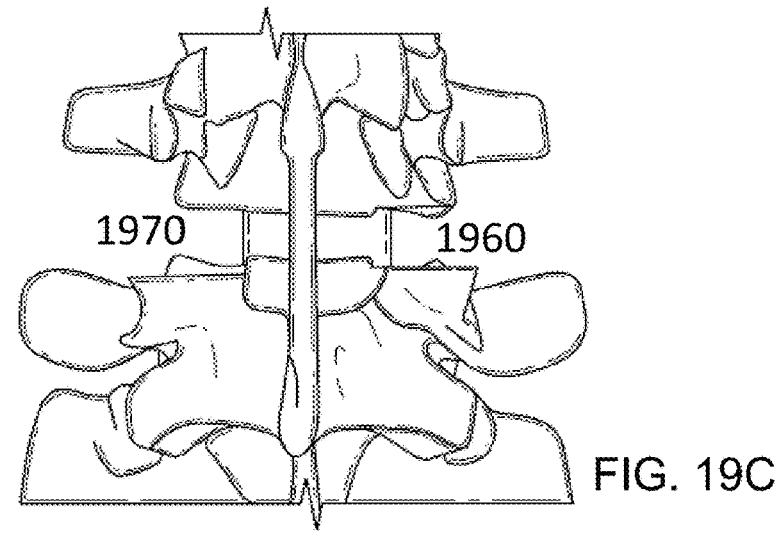

FIGS. 19A-19C depict one embodiment of the preparation of a caudal vertebral body 1900 and a cranial vertebral body 1910 to alter the caudal body native endplate surface 1920 and cranial body native endplate surface 1930 from a degenerated and/or non-parallel orientation (see FIG. 19A). In various embodiments, a resection plan can be created which includes a caudal endplate surface resection plane 1940 and a cranial endplate surface resection plane 1950 (See FIG. 19B). Desirably, the resulting resected caudal and cephalad endplate surfaces on a medial side 1960 and the resected caudal and cranial endplate surfaces on a lateral side 1970 will achieve parallel and/or substantially parallel surfaces to achieve a desirable and/or optimal alignment and range of motion for the subsequent implant. The AOC is obtained for at least one side, a first side and/or a second side from the preoperative method or steps discussed herein. The AOC allows the surgeon to further prepare the cranial vertebral body to match or substantially match to the pre-operative AOC measurement. The AOC measurement comprises a coronal and/or a sagittal angle, each of the angles include 0 degrees to 40 degrees. The surgeon may activate the powered rasp that is disposed onto the native endplate surface by pressing on the footswitch—a light pressure equals a slow reciprocating speed, and a hard pressure equals a faster reciprocating speed. The surgeon prepares at least a portion of the inferior endplate on the cranial verte-bral body by utilizing the flat reciprocating rasp at a desired speed until a slight bleeding is observed to facilitate bony ingrowth to the spinal implant after deployment to create a resected or prepared surface, a first resected or prepared surface and/or a second resected or prepared surface. Alter-natively, the surgeon may prepare at least a portion of the inferior endplate on the cranial vertebral body following along, matching or substantially matching the pedicle trans-verse angle (e.g., the pedicle axis) utilizing the long, flat rasp as a desired speed and a slight bleeding is observed to facilitate bony ingrowth to the spinal implant after deploy-ment to create a resected or prepared surface (bony material may or may not be removed). The transverse pedicle angle may include 0 degrees to 45 degrees. Accordingly, the surgeon may prepare at least a portion of the inferior endplate of the cranial vertebral body to comprise a first resected or prepared shape, a first resected or prepared length, a first resected or prepared width and a first resected or prepared depth. The surgeon may prepare at least a portion of the inferior endplate of the cranial vertebral body to match or substantially match the pre-determined AOC from the pre-procedure steps.

Furthermore, the step of preparing the cranial vertebral body on the at least one side, first side and/or second side, may include the step of acquiring at least image using an imaging technique on at least one side, a first side and/or a second side to confirm the angle and/or the angle of correc-tion of the resected or prepared surface, the first resected or prepared surface and/or the second resected or prepared surface by acquiring at least one image using at least one imaging technique. The surgeon may verify that the angle of the resected surface, the first resected surface and/or second resected surface by comparing it to the realignment resection plane measured during the pre-operative planning proce-dures for restoration or substantial restoration of a patient's coronal and/or sagittal alignment. The at least one image may be performed by using at least one imaging technique. The imaging techniques may comprise 2D or 3D images. The imaging techniques may comprise an MRI, a radio-graph, a CT scan, an ultrasound, and/or any combination thereof. The preparation of the endplate surface of the cranial vertebral body on the contralateral side may be performed by repeating the above steps.

Figure 20A:
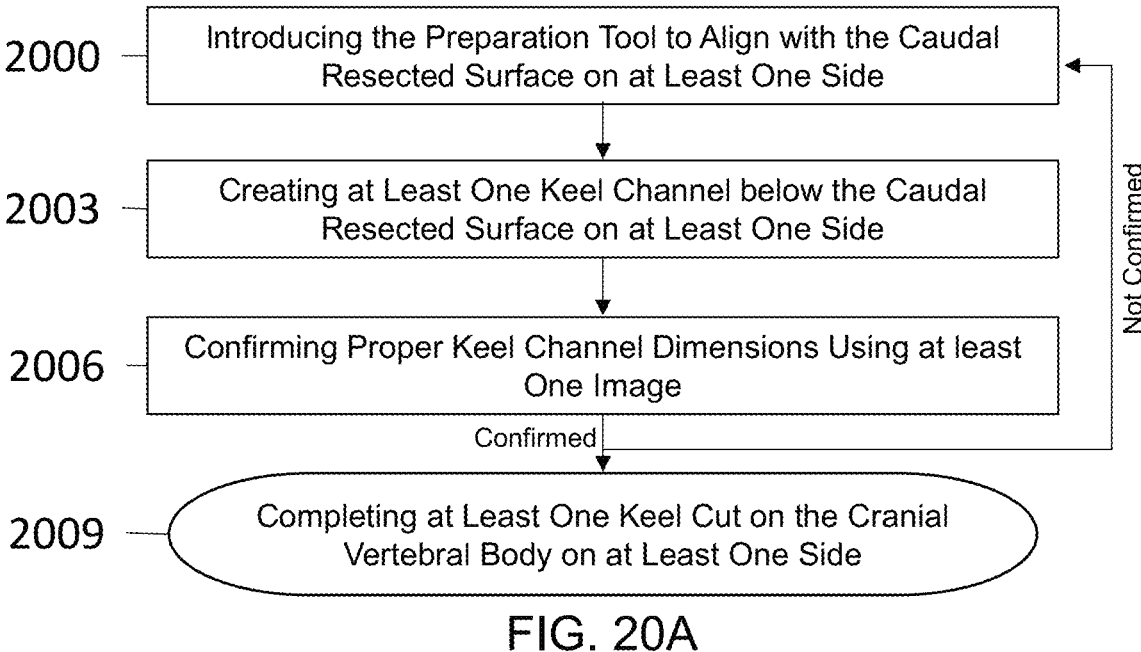

With reference to FIG. 20A, the step of preparing an intervertebral space within a localized spinal segment for alignment and motion restoration comprises the step of completing at least one keel channel on the caudal vertebral body on least a one side. The step of completing at least one keel channel on the caudal vertebral body on at least one side comprises the steps of introducing the preparation tool into prepared intervertebral disc space 2000; creating at least one keel channel below the prepared or resected surface on the caudal vertebral body 2003; confirming the at least one keel channel placement or positioning by acquiring at least one image using at least one imaging technique 2006.

Figure 20B:
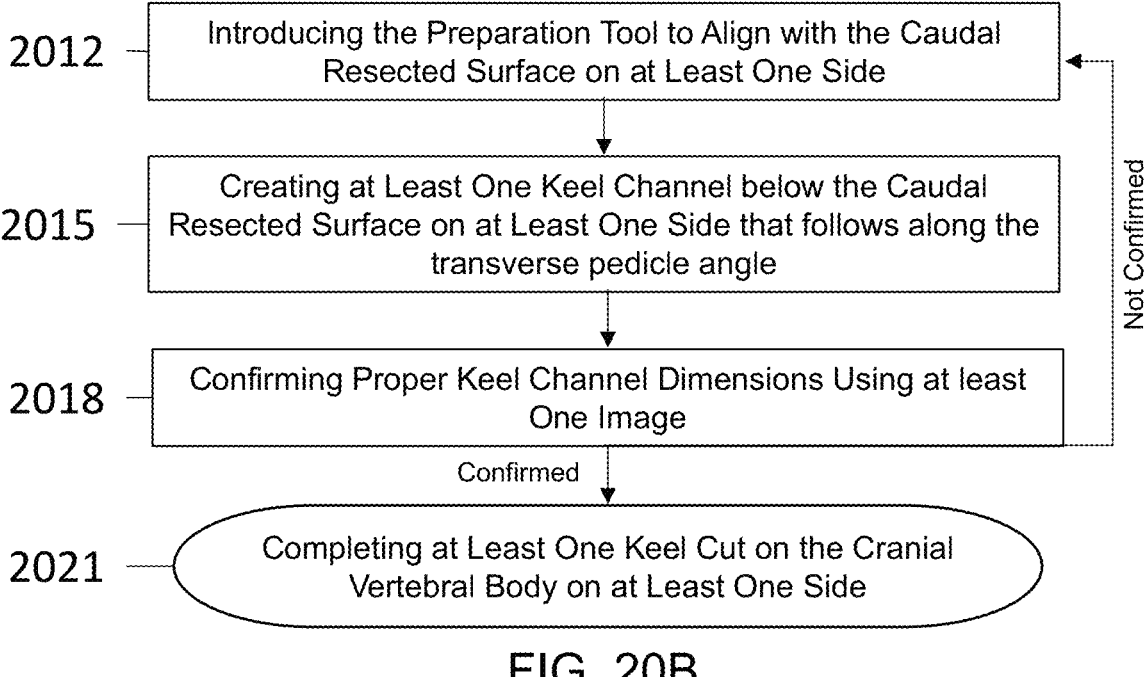

With reference to FIG. 20B, the step of preparing an intervertebral space within a localized spinal segment for alignment and motion restoration comprises the step of completing at least one keel channel on the caudal vertebral body on least a one side. The step of completing at least one keel channel on the caudal vertebral body on at least one side comprises the steps of introducing the preparation tool into prepared intervertebral disc space 2012; creating at least one keel channel below the prepared or resected surface on the caudal vertebral body that follows along, matches or sub-stantially matches the transverse pedicle angle 2015; con-firming the at least one keel channel placement or position-ing by acquiring at least one image using at least one imaging technique 2018.

With reference to FIG. 20C, the step of preparing an intervertebral space within a localized spinal segment for alignment and motion restoration comprises the step of completing a first and second keel channel on a first and second side. The step of completing at least one keel channel on the caudal vertebral body on at least one side comprises the steps of: introducing a first preparation tool into prepared intervertebral disc space on a first side and a second prepa-ration tool into the prepared intervertebral disc space on a second side 2024; creating at first keel channel below the first prepared or resected surface on the caudal vertebral body on the first side and a second keel channel below the second prepared or resected surface on the caudal vertebral body on the second side 2027; confirming the first and second keel channel placement or positioning by acquiring at least one image using at least one imaging technique on a first and second side 2030.

With reference to FIG. 20D, the step of preparing an intervertebral space within a localized spinal segment for alignment and motion restoration comprises the step of completing a first and second keel channel on a first and second side. The step of completing at least one keel channel on the caudal vertebral body on at least one side comprises the steps of: introducing a first preparation tool into prepared intervertebral disc space on a first side and a second prepa-ration tool into the prepared intervertebral disc space on a second side 2036; creating at first keel channel below the first prepared or resected surface on the caudal vertebral body that follows along, matches or substantially matches a first transverse pedicle angle on the first side and a second keel channel below the second prepared or resected surface on the caudal vertebral body that follows along, matches or substantially matches the transverse pedicle angle on the second side 2039; confirming the first and second keel channel placement or positioning by acquiring at least one image using at least one imaging technique on a first and second side 2042.

Figure 20E:
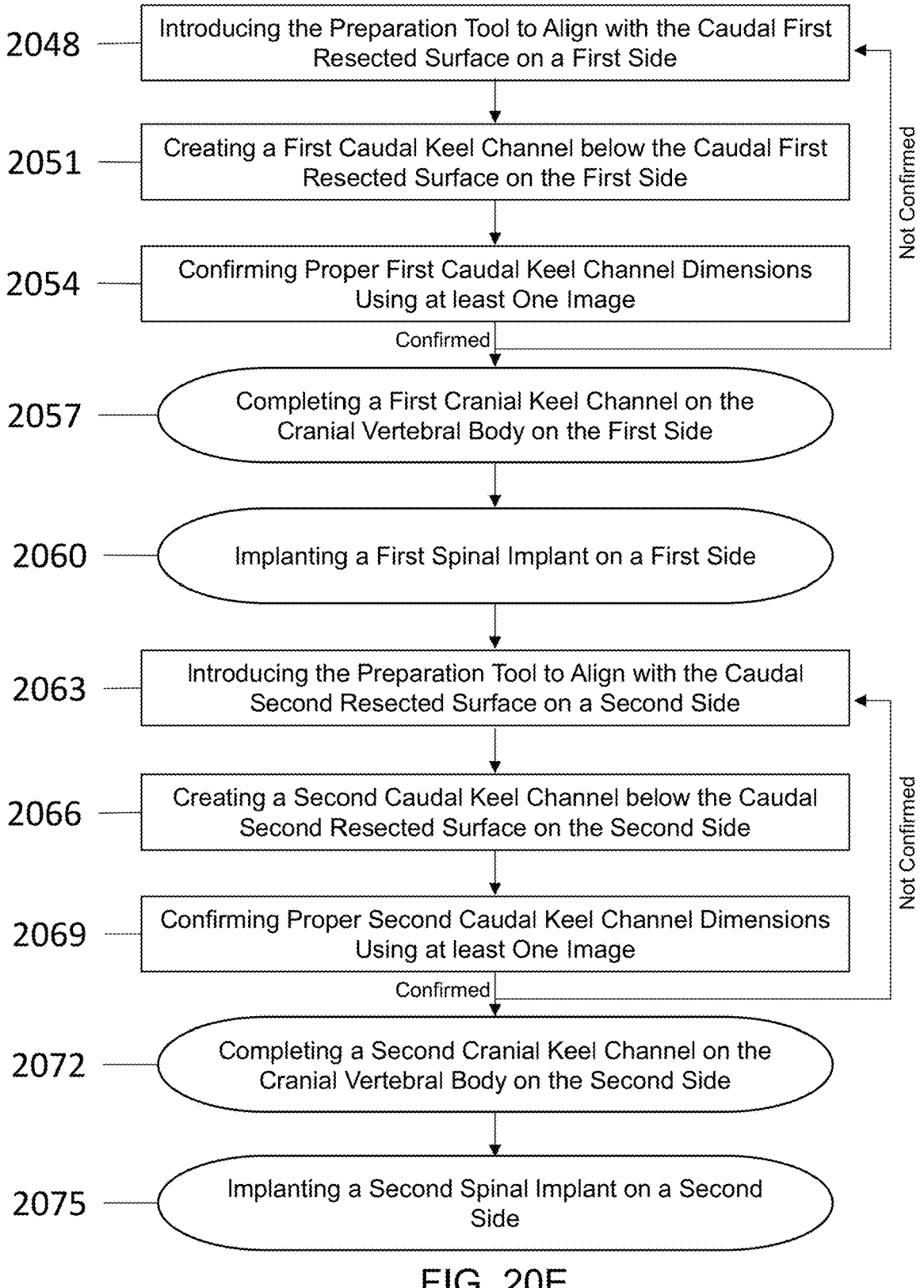

With reference to FIG. 20E, the step of preparing an intervertebral space within a localized spinal segment for alignment and motion restoration comprises the step of completing a first keel channel on the caudal vertebral body on a first side. The step of completing a first keel channel on the caudal vertebral body on the first side comprises the steps of introducing the first preparation tool into the pre-pared intervertebral disc space 2048; creating a first keel channel below the first prepared or resected surface on the caudal vertebral body 2051; confirming the at least one keel channel placement or positioning by acquiring at least one image using at least one imaging technique 2054. The first keel channel may follow along, match or substantially match the transverse pedicle angle. The transverse pedicle angle comprises an angle of 0 degrees to 45 degrees. With this embodiment, the surgeon should proceed with all of the remaining steps of preparing the intervertebral space within a localized spinal segment for alignment and motion resto- ration for a first side prior to completing the steps for a second side. The remaining steps can include one or more of the following steps: preparing an intervertebral space within a localized spinal segment for alignment and motion resto- ration for a first side (2048-2054); implanting a first spinal implant on a first side 2060; preparing an intervertebral space within a localized spinal segment for alignment and motion restoration for a second side (2063-2069); and implanting a second spinal implant on a second side 2075.

The first keel channel may comprise the same dimensions as the second keel channel. The first keel channel may comprise different dimension as the second keel channel. The first transverse pedicle angle of the first keel channel may comprise the same angle as the second transverse pedicle angle of the second keel channel. The first spinal implant may comprise the same selected size as the second spinal implant. The first spinal implant may comprise a different selected size as the second spinal implant. The selected sizes may include different lengths or heights.

In one embodiment, the step of completing at least one keel channel on the caudal vertebral body may comprise the steps of assembling the keel tools; and inserting the keel tool into the prepared interverbal disc space. Prior to the com- pleting at least one keel channel on the caudal vertebral body on at least one side, a first side and/or a second side, the surgeon may subsequently assemble the proper tools. The tools may comprise a rasp, a manual handle, and/or a powered system. The surgeon may create the keel channels using a manual and/or a powered system. In one embodi- ment, the surgeon may use a powered system. The powered system comprises a powered reciprocating system, and a rasp. The rasp may comprise a long or short keel rasp. To use the powered reciprocating system, the surgeon should con- nect the cables and cord into an outlet allowing the powered reciprocating system to activate. The surgeon may subse- quently insert a rasp into an unlocked handpiece and twist the locking collar on the handpiece to lock the rasp into the handpiece. The surgeon may test the powered system by stepping on the footswitch. The pressure on the footswitch determines the variable speed to activate and/or reciprocate the rasp.

In one embodiment, the step of completing at least one keel channel on the caudal vertebral body may comprise the steps of inserting the keel tool into the prepared interverbal disc space. Once the proper tools are prepared, the surgeon may align the rasp with a keel onto the resected surface, the first resected surface and/or the second resected surface of the caudal vertebral body. The surgeon may continue to translate, slide or introduce the inactivated powered rasp to the at least one side within a prepared disc space along the desired resected path. Alternatively, the surgeon may intro- duce the inactivated powered rasp following along the pedicle transverse angle (or pedicle axis) on the at least one side within a disc space. The rasp comprises a long or short keel rasp. The surgeon should confirm placement and/or positioning of the tools by acquiring at least one image with at least one imaging technique on the portions of the resected caudal endplate surface and/or resected pedicle surface. Furthermore, the surgeon may desirably retract the exiting nerve root and lateral thecal sack to protect the neural elements during the use of the rasp.

In one embodiment, the step of completing at least one keel channel on the caudal vertebral body comprises the step of creating at least one keel channel, a first keel channel and/or a second keel channel on at least one side, a first side and/or a second side. The surgeon may activate the powered rasp by pressing on the footswitch—a light pressure equals a slow reciprocating speed, and a hard pressure equals a faster reciprocating speed. The surgeon prepares and/or creates a keel channel on a least a portion of the resected surface on the caudal vertebral body by utilizing the long or short keel reciprocating rasp at a desired speed on at least one side, a first side and/or a second side. Alternatively, the surgeon may create the keel channel on the caudal vertebral body following along, matching or substantially matching the pedicle transverse angle (e.g., the pedicle axis) utilizing the keel rasp to create a keel channel on at least one side, a first side and/or a second side. The keel channel on the caudal vertebral body extends from the resected surface downwards towards the inferior direction. The keel channel comprises a keel channel depth, a width and a length. The keel channel depth, width and length matches or substan- tially matches a portion of the spinal implant keel length, width and/or depth. The keel channel width matches or substantially matches the widest portion of the spinal implant keel width.

In another embodiment, the surgeon prepares and/or cre- ates a first keel channel on a least a portion of the first resected surface on the caudal vertebral body and a second keel channel on the second resected surface on the caudal vertebral body by utilizing the long or short keel recipro- cating rasp at a desired speed. Alternatively, the surgeon may create the first and second keel channel on the caudal vertebral body following along, matching or substantially matching the pedicle transverse angle (e.g., the pedicle axis) utilizing the keel rasp. The first and second keel channels on the caudal vertebral body extends from the resected surface downwards towards the inferior direction. The first and second keel channels comprises a keel channel depth, a width and a length. Each of the first and second keel channels depth, width and length matches or substantially matches each of the spinal implant keel length, width and/or depth. The first and second keel channel width matches or substantially matches the spinal implant keel width. The first and second keel channel depth of the caudal vertebral body matches or substantially matches the spinal implant keel depth.

In another embodiment, the step of completing at least one keel channel on the caudal vertebral body comprises the step of confirming at least one keel channel, a first keel channel and/or a second keel channel on the caudal vertebral body by acquiring at least one or more images. The surgeon may confirm the keel channel, the first keel channel and/or the second keel channel of the caudal vertebral body by acquiring at least one image using at least one imaging technique. The surgeon may verify the keel channel, the first keel channel and/or the second keel channel of the caudal vertebral body dimensions and/or convergence angle (or transverse pedicle angle). The at least one image may be performed by using at least one imaging technique. The imaging techniques may comprise 2D or 3D images. The imaging techniques may comprise an MRI, a radiograph, a CT scan, an ultrasound, and/or any combination thereof.

Figure 21A:
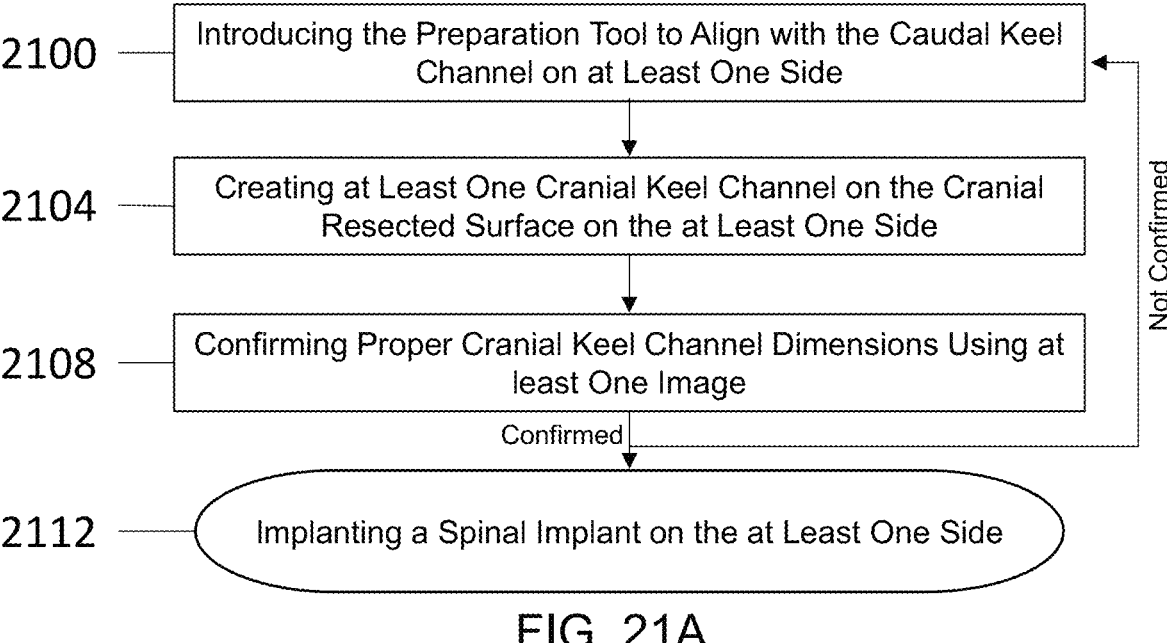
FIGS. 21A-21E graphically illustrates different embodiments of a method of completing at least one keel channel on the cranial vertebral body.

With reference to FIG. 21A, the step of preparing an intervertebral space within a localized spinal segment for alignment and motion restoration comprises the step of completing at least one keel channel on the cranial vertebral body on least a one side. The step of completing at least one keel channel on the cranial vertebral body on at least one side comprises the steps of: introducing the preparation tool into prepared intervertebral disc space to align with at least one caudal keel channel 2100; creating at least one cranial keel channel above the prepared or resected surface on the cranial vertebral body 2104; confirming the at least one keel channel placement or positioning by acquiring at least one image using at least one imaging technique 2108.

Figure 21B:
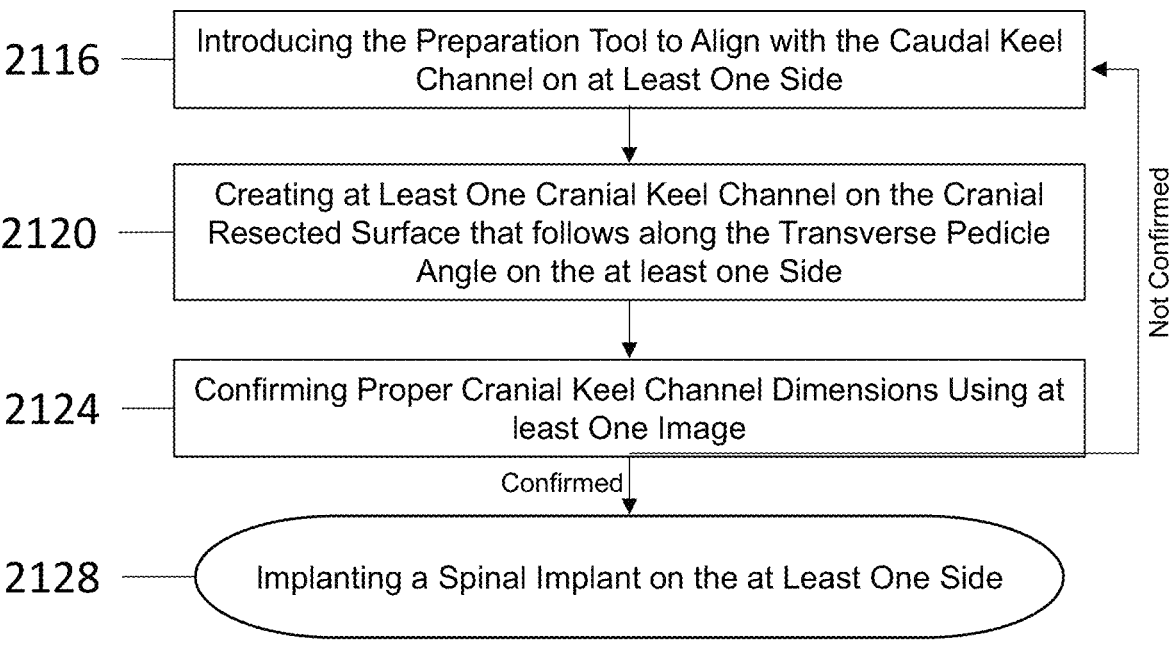

With reference to FIG. 21B, the step of preparing an intervertebral space within a localized spinal segment for alignment and motion restoration comprises the step of completing at least one keel channel on the caudal vertebral body on least a one side. The step of completing at least one keel channel on the cranial vertebral body on at least one side comprises the steps of introducing the preparation tool into prepared intervertebral disc space to align with the caudal keel channel on the at least one side 2116; creating at least one cranial keel channel above the prepared or resected surface on the cranial vertebral body that follows along, matches or substantially matches the transverse pedicle angle 2120; confirming the at least one cranial keel channel placement or positioning by acquiring at least one image using at least one imaging technique 2124.

Figure 21C:
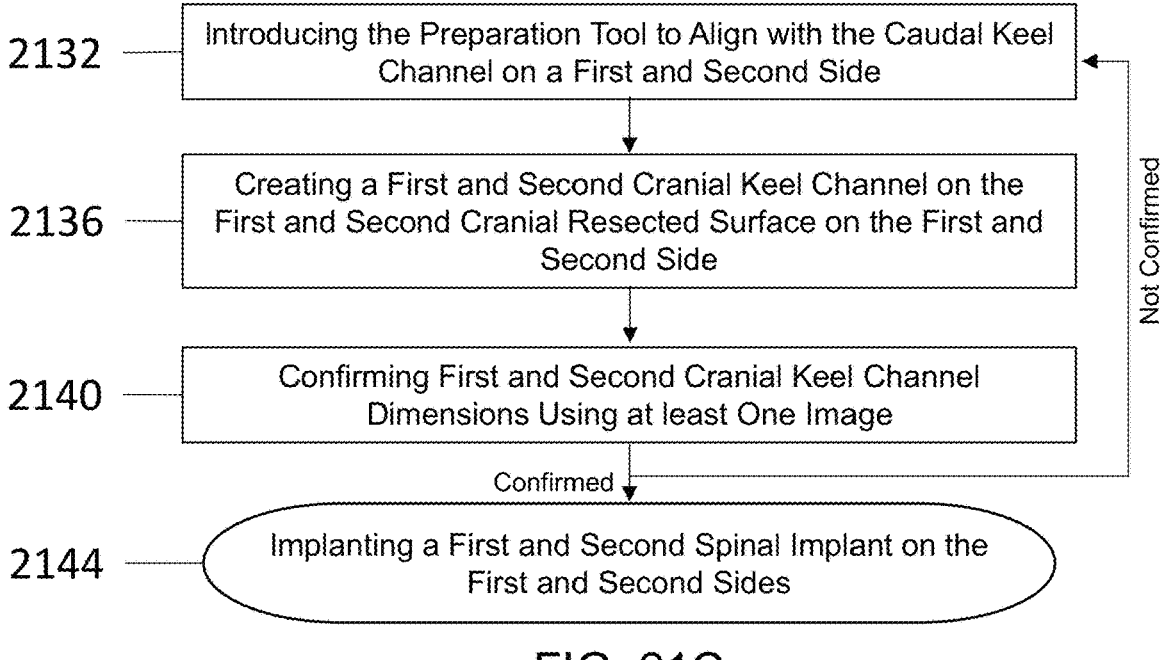

With reference to FIG. 21C, the step of preparing an intervertebral space within a localized spinal segment for alignment and motion restoration comprises the step of completing a first and second cranial keel channel on a first and second side. The step of completing at a first and second cranial keel channels on the caudal vertebral body on a first and second side comprises the steps of: introducing a first preparation tool into prepared intervertebral disc space that aligns with the first caudal keel channel on a first side and a second preparation tool into the prepared intervertebral disc space that aligns with the second caudal keel channel on a second side 2132; creating at first keel channel above the first prepared or resected surface on the cranial vertebral body on the first side and a second keel channel above the second prepared or resected surface on the cranial vertebral body on the second side 2136; confirming the first and second cranial keel channel placement or positioning by acquiring at least one image using at least one imaging technique on a first and second side 2140.

Figure 21D:
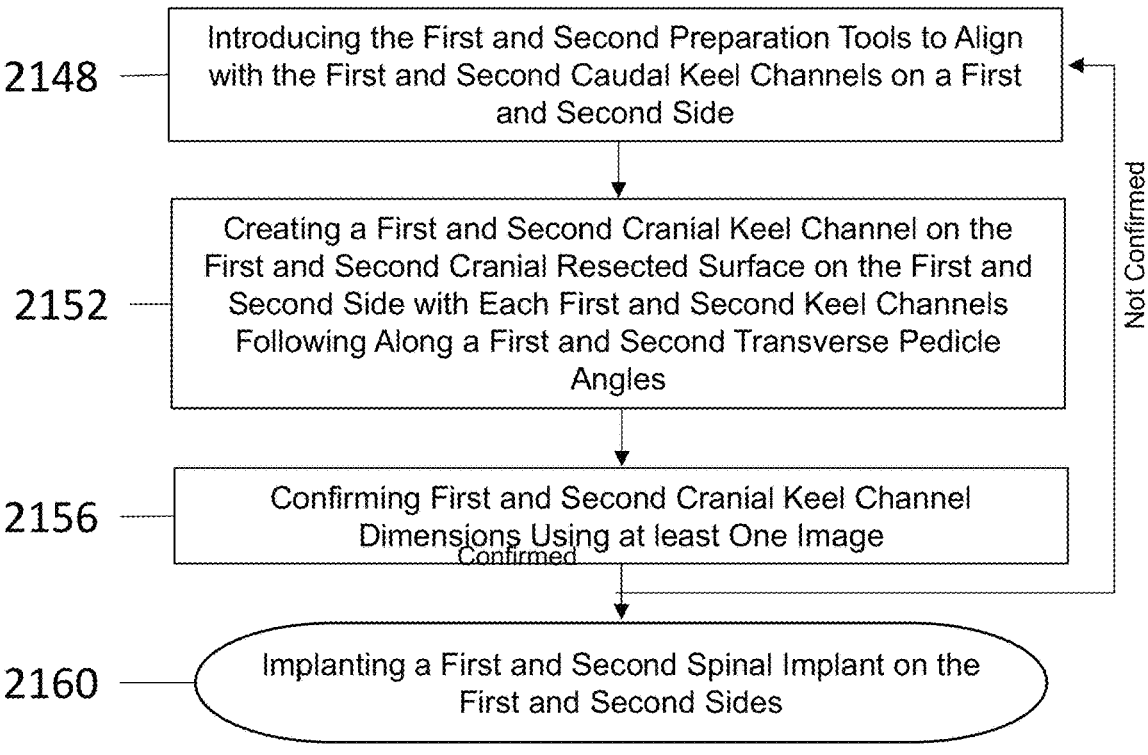

With reference to FIG. 21D, the step of preparing an intervertebral space within a localized spinal segment for alignment and motion restoration comprises the step of completing a first and second cranial keel channel on a first and second side. The step of completing a first and second cranial keel channels on the cranial vertebral body on a first and second side comprises the steps of: introducing a first preparation tool into prepared intervertebral disc space on a first side that aligns with the first caudal keel channel and a second preparation tool into the prepared intervertebral disc space on a second side that aligns with the second caudal keel channel 2148; creating at first cranial keel channel above the first prepared or resected surface on the cranial vertebral body that follows along, matches or substantially matches a first transverse pedicle angle on the first side and a second cranial keel channel above the second prepared or resected surface on the cranial vertebral body that follows along, matches or substantially matches the transverse pedicle angle on the second side 2152; confirming the first and second keel cranial channels placement or positioning by acquiring at least one image using at least one imaging technique on a first and second side 2156.

Figure 21E:
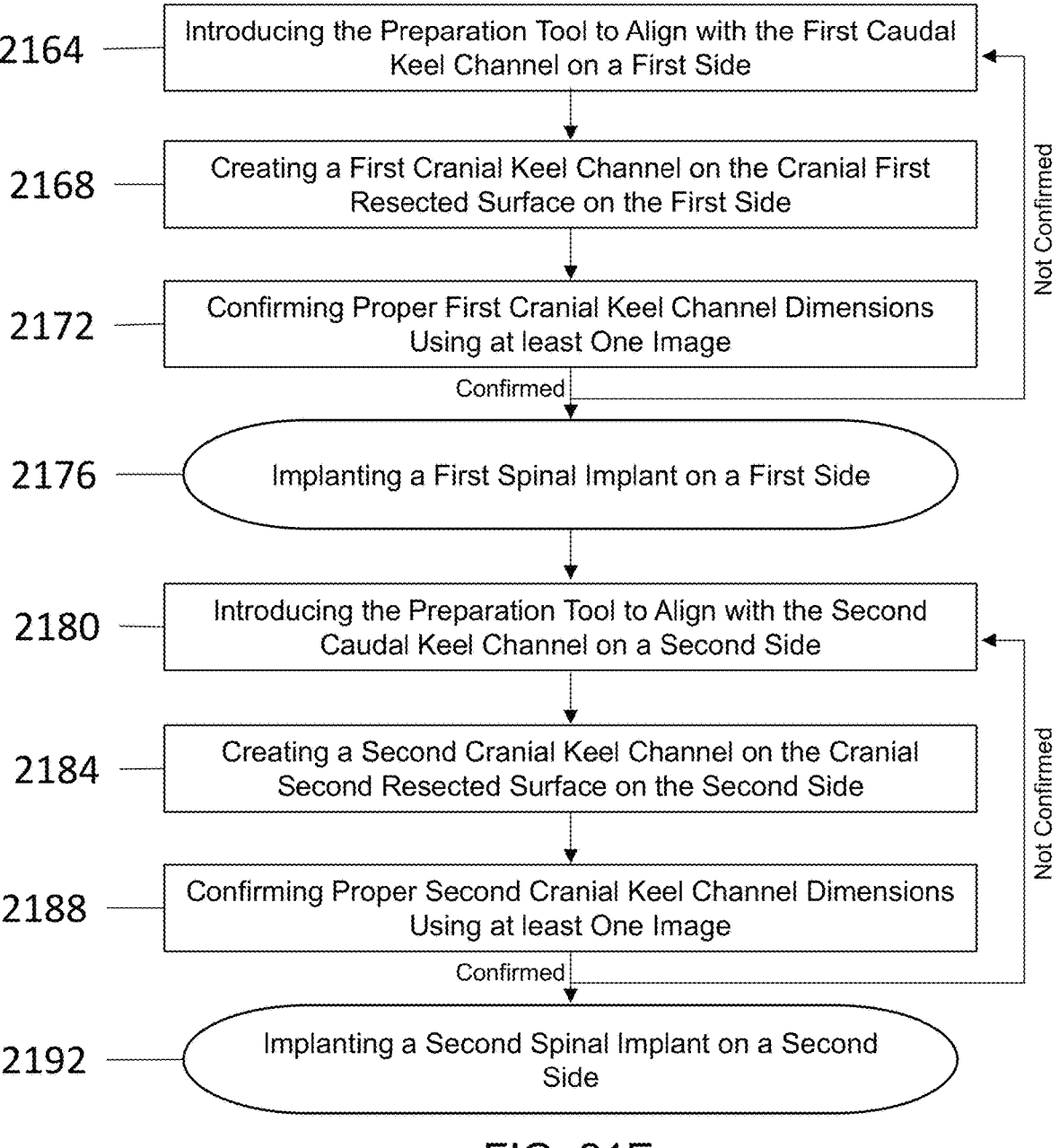

With reference to FIG. 21E, the step of preparing an intervertebral space within a localized spinal segment for alignment and motion restoration comprises the step of completing a first cranial keel channel on the cranial vertebral body on a first side. The step of completing a first cranial keel channel on the cranial vertebral body on the first side comprises the steps of introducing the first preparation tool into the prepared intervertebral disc space that aligns with the first caudal keel channel on a first side 2164; creating a first cranial keel channel above the first prepared or resected surface on the cranial vertebral body 2168; confirming the at least one cranial keel channel placement or positioning by acquiring at least one image using at least one imaging technique 2172. The first keel channel may follow along, match or substantially match the transverse pedicle angle. The transverse pedicle angle comprises an angle of 0 degrees to 45 degrees. With this embodiment, the surgeon should proceed with all the remaining steps of preparing the intervertebral space within a localized spinal segment for alignment and motion restoration for a first side prior to completing the steps for a second side. The remaining steps include step of preparing an intervertebral space within a localized spinal segment for alignment and motion restoration for a first side; implanting a first spinal implant on a first side (2164-2172); preparing an intervertebral space within a localized spinal segment for alignment and motion restoration for a second side (2180-2188); and implanting a second spinal implant on a second side 2192.

Figure 22A:
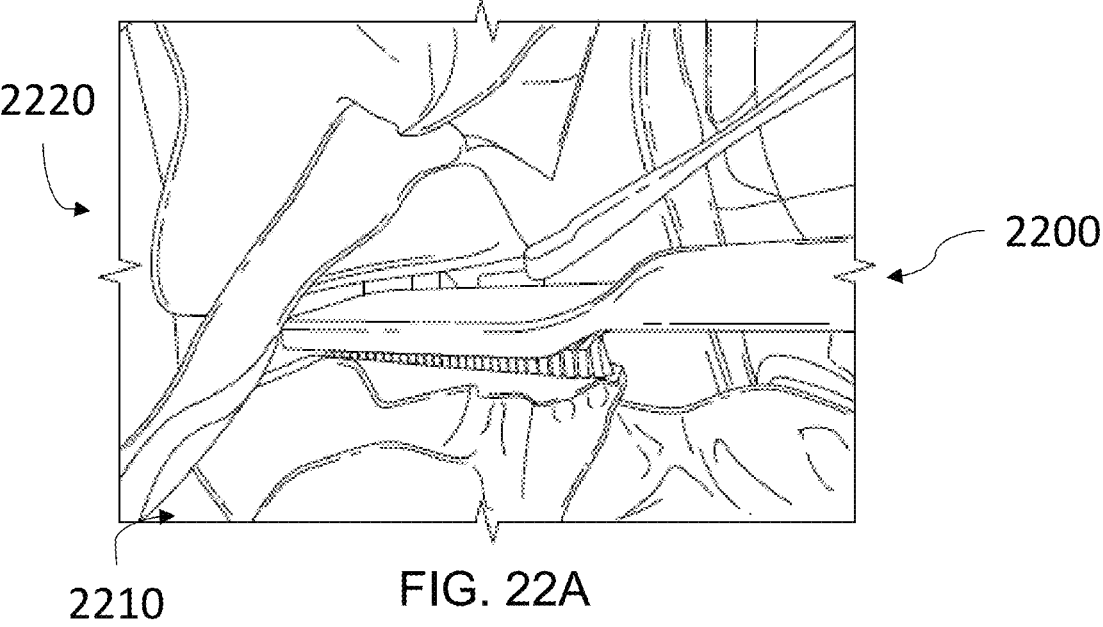
FIGS. 22A-22B depict an isometric sagittal view and a top view of prepared keel channel on the caudal vertebral body.
Figure 22B:
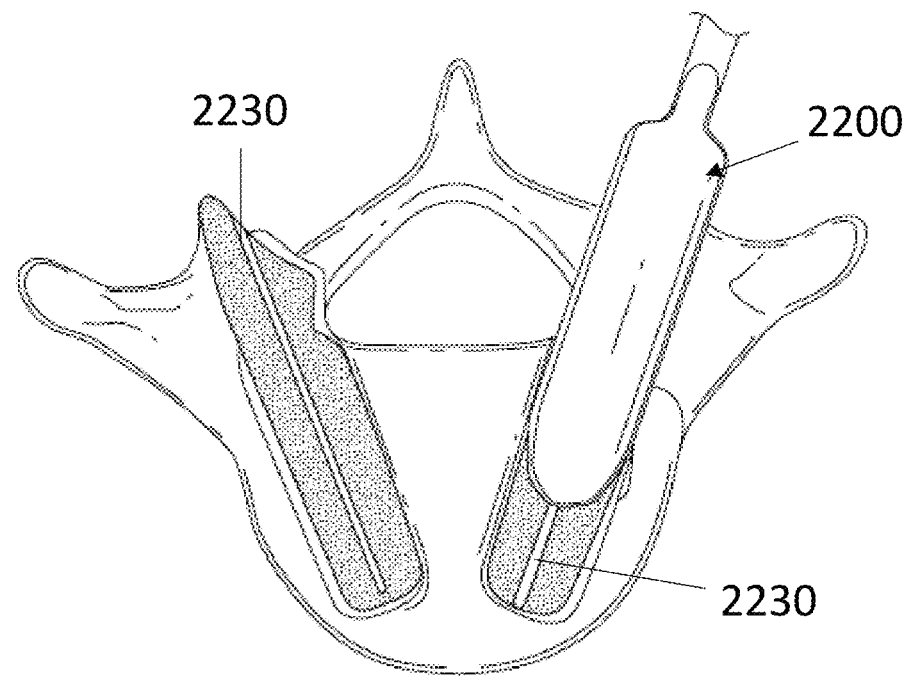
Figures 23A, 23B, 23C, 23D:
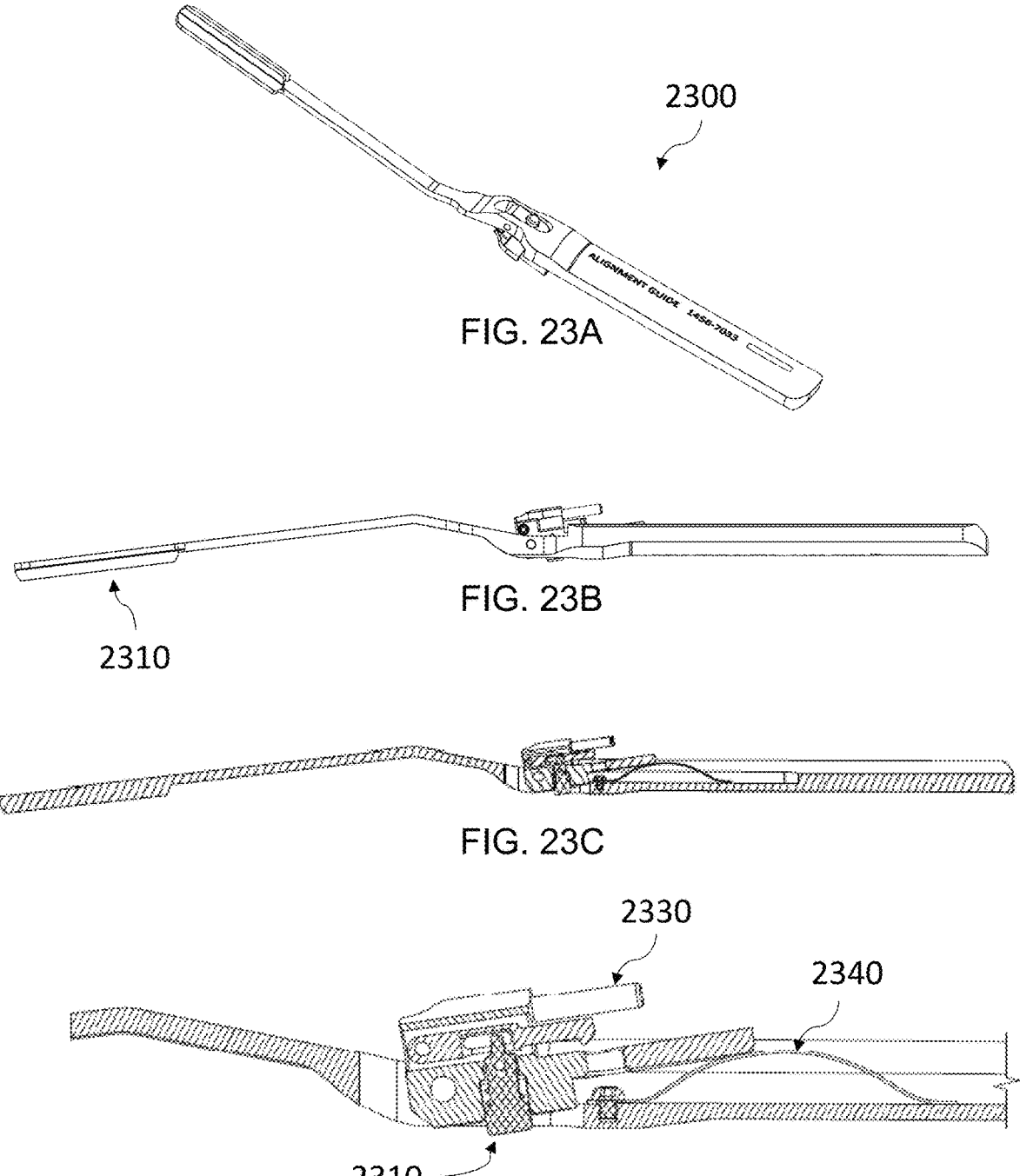
FIGS. 23A-23D depict different views of one embodiment of a keel alignment tool for the method of completing at least one keel channel on the cranial vertebral body.
Figure 24A:
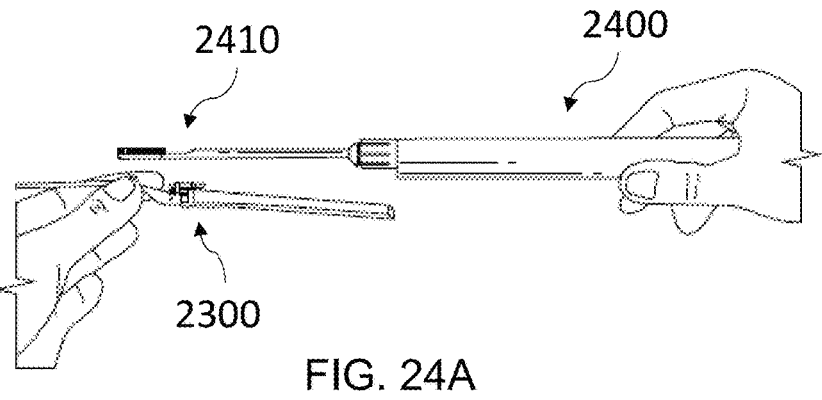
FIGS. 24A-24E depicts different views of a method to assemble a keel alignment tool.
Figure 24B:
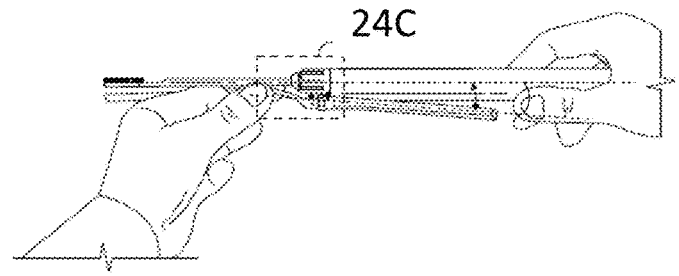
Figure 24C:
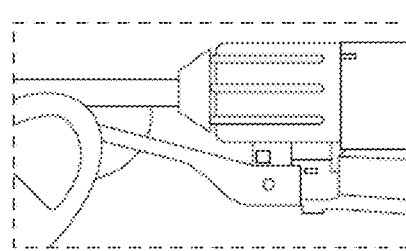
Figure 24D:
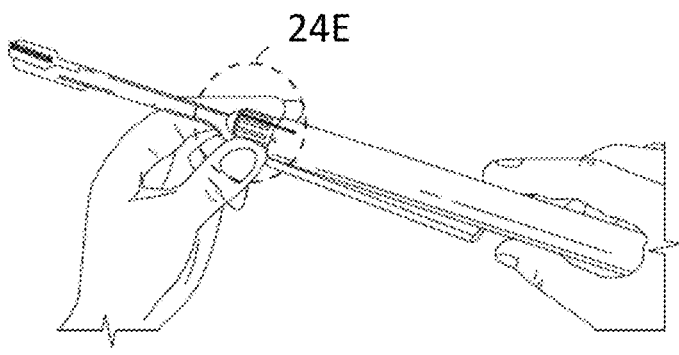
Figure 24E:
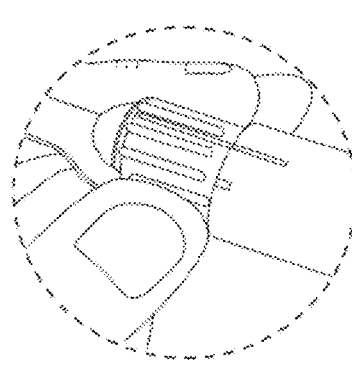

The first cranial keel channel may comprise the same dimensions as the second cranial keel channel. The first cranial keel channel may comprise different dimensions as the second cranial keel channel. The first transverse pedicle angle of the first cranial keel channel may comprise the same angle as the second transverse pedicle angle of the second cranial keel channel. The first spinal implant may comprise the same selected size as the second spinal implant. The first spinal implant may comprise a different selected size as the second spinal implant. The selected sizes may include different lengths or heights. FIGS. 22A-22B depict an isometric sagittal view and a top plan view of one embodiment of a keel rasp 2200 used to form one or more caudal keel channels 2230 into a caudal vertebral body 2210, adjacent to a cranial vertebral body 2220.

In another embodiment, the step of preparing intervertebral space within localized spinal segment for alignment restoration comprises the step of introducing the at least one preparation tool into the prepared intervertebral disc space that aligns with the first caudal keel channel on at least one side, a first side and/or a second side. The step of introducing the at least one preparation tool into the prepared intervertebral disc space that aligns with the first caudal keel channel on at least one side, a first side and/or a second side comprises the steps of assembling the preparation tools; and inserting a portion of the preparation tool(s) into the at least one caudal keel channel, a first caudal keel channel and/or second caudal keel channel to align the at least one cranial keel channel, a first cranial keel channel and/or a second cranial keel channel.

In one embodiment, the surgeon may subsequently prepare and/or assemble the proper preparation tools. The tools may comprise a rasp, a manual handle, and/or a powered system. The tools may further comprise an AO modular connector and/or a keel alignment guide. In one embodiment, the surgeon may use a powered system. The powered system comprises a powered reciprocating system, and a tool, the tool includes a rasp. The rasp may comprise a long or short keel rasp. To use the powered reciprocating system, the surgeon should connect the cables and cord into an outlet allowing the powered reciprocating system to activate. The surgeon may subsequently insert an AO modular connector portion of the short keel rasp into an unlocked powered handpiece and/or insert one end with the AO modular connector into the unlocked powered handpiece. Twist the locking collar on the handpiece to lock the rasp into the powered handpiece.

The surgeon may desirably assemble an alignment guide 2300, if desired and/or necessary, such as shown in FIGS. 23A-23D and 24A-24E. The alignment guide 2300 can include a keel portion 2310, an actuator button 2320, one or more dowel pins 2330 and a leaf spring 2340. In use, the surgeon can desirably align the one or more dowels pins 2330 of the alignment guide into corresponding alignment pin openings of a powered handpiece 2400 or similar device, wherein the alignment guide 2300 can index off the previously created caudal keel to align the keel rasp 2410 for creating a cranial keel in the cranial vertebral body. This arrangement allows the surgeon to rest a portion of the powered handpiece onto a portion and/or the handle of the alignment guide—providing an angle of rest (e.g., the handle of the alignment guide relative to the powered handpiece) as well as a lever and pivot point near the vertebral body to elevate the cranial rasp against and/or into the cranial vertebral body in a controlled manner (e.g., by squeezing the alignment guide handle). If readjustment of the alignment guide is necessary, the surgeon may simply push the button on the bottom of the alignment guide and slide distally until the desired location is reached. The surgeon may operate and/or test operation of the powered system at any time by stepping on the footswitch to activate powered motion. Desirably, the pressure on the footswitch can determine the variable speed to activate and/or reciprocate the rasp.

In another embodiment, the step of introducing the at least one preparation tool into the prepared intervertebral disc space that aligns with the first caudal keel channel on at least one side, a first side and/or a second side comprises the steps inserting a portion of the preparation tool(s) into the at least one caudal keel channel, a first caudal keel channel and/or second caudal keel channel to align the at least one cranial keel channel, a first cranial keel channel and/or a second cranial keel channel.

The surgeon may retract the exiting nerve root and the thecal sac using retractors to protect the neural elements. The surgeon may align and insert or introduce a portion of the alignment guide and/or the keel of the alignment guide with the short keel rasp assembly into at least one of the caudal keel channels, the first caudal keel channel and/or a second caudal keel channel one the at least one side without pressing, squeezing or compressing the handle of the alignment guide relative to the powered handpiece as shown in FIGS. 25A-25D. Alternatively, the surgeon may align and insert or introduce a portion of the alignment guide with the short keel rasp into the at least one keel channel, the first caudal keel channel and/or a second caudal keel channel within the prepared intravertebral disc space that follows, matches and/or substantially matches the pedicle transverse angle (or pedicle axis) on the at least one side without pressing, squeezing or compressing the handle of the alignment guide relative to the powered handpiece as shown in FIG. 25A. The surgeon should avoid contacting the resected surface of the cranial (or superior) vertebral body by accidentally pressing, squeezing or compressing the handle of the alignment guide relative to the powered handpiece. The squeezing or compressing action will cause the short keel rasp to lift superiorly toward the prepared cranial resected surface. The short keel feature of the short keel rasp should be spaced apart from the resected surface of the cranial (or superior) vertebral body. The spacing may include a distance of at least 1 mm. The surgeon should continue to translate the alignment guide and the short keel rasp anteriorly within the at least one caudal keel channels until the alignment guide stops translating. The surgeon should confirm placement, alignment and/or positioning of the tools by acquiring at least one image with at least one imaging technique.

The surgeon may then activate the powered rasp by pressing on the footswitch—a light pressure equals a slow reciprocating speed, and a hard pressure equals a faster reciprocating speed. The surgeon can then prepare and/or create at least one cranial keel channel on a least a portion of the resected surface on the cranial vertebral body by squeezing or compressing the handle of the alignment guide relative to the powered handpiece to lift the short keel rasp superiorly towards at least a portion of the cranial resected or prepared surface until it contacts the at least one resected or prepared surface, a first resected or prepared surface and/or a second resected or prepared surface of the cranial vertebral body on at least one side, a first side and/or a second side as shown in FIG. 25B. The surgeon may initiate the reciprocation of the powered handpiece to create at least a portion of one cranial keel channel on the at least one side (e.g., stamping or inscribing) as shown in FIG. 25C. The surgeon may desirably remove the alignment guide from the powered handpiece to complete the remaining portion of the at least one cranial keel channel on at least one side. Alternatively, the surgeon may initiate the reciprocation of the powered handpiece to create the entirety of one cranial keel channel on the at least one side. The surgeon may slide or translate the powered handpiece with rasp assembly and/or alignment guide posteriorly. The at least one cranial keel channel on the cranial vertebral body extends from the resected surface towards the superior direction. The at least one cranial keel channel comprises a cranial keel channel depth, a width and a length. The cranial keel channel depth, width and length matches or substantially matches a portion of the spinal implant keel length, width and/or depth. The cranial keel channel width matches or substantially matches the widest portion of the spinal implant keel width. Once the keel channel has been created, the surgeon may remove the alignment guide and/or the keel rasp from the prepared intervertebral space.

The surgeon should confirm placement, alignment and/or positioning of the at least one cranial keel channel on the at least one side by acquiring at least one image with at least one imaging technique. The placement, alignment and/or positioning of the at least one cranial keel channel includes longitudinal alignment of the at least one caudal keel channel on the at least one caudal vertebral body relative to the at least one cranial keel channel on the at least one cranial vertebral body. In one embodiment, the at least one side comprises at least one caudal keel channel and at least one cranial keel channel. The at least one caudal keel channel comprises a caudal longitudinal axis and the at least one cranial keel channel comprises a cranial longitudinal axis. The cranial longitudinal axis and the caudal longitudinal axis are parallel and/or substantially parallel. In another embodiment, the at least one caudal keel channel comprises a caudal vertical axis and the at least one cranial keel channel comprises a cranial vertical axis. The cranial vertical axis and the caudal vertical axis are co-axial and/or substantially co-axial. In another embodiment, the cranial longitudinal axis and the caudal longitudinal axis are parallel and/or substantially parallel, and the cranial vertical axis and the caudal vertical axis are co-axial and/or substantially co-axial.

In another embodiment, the surgeon may complete the step of completing and/or creating a first cranial keel channel on a cranial vertebral body on a first side and creating a second cranial keel channel on a cranial vertebral body on a second side. The surgeon may retract the exiting nerve root and the thecal sac using retractors to protect the neural elements. The surgeon may align and insert or introduce a portion of the alignment guide and/or the keel of the alignment guide with the short keel rasp assembly into a first caudal keel channel on the first side and/or into a second caudal keel channel on the second side without pressing, squeezing or compressing the handle of the alignment guide relative to the powered handpiece. Alternatively, surgeon may align and insert or introduce a portion of the alignment guide with the short keel rasp into the first caudal keel channel that follows, matches and/or substantially matches the pedicle transverse angle (or pedicle axis) on the first side and/or into the second caudal keel channel that follows, matches and/or substantially matches the pedicle transverse angle on the second side without pressing, squeezing or compressing the handle of the alignment guide relative to the powered handpiece.

The surgeon should avoid contacting the cranial resected or prepared surface of the cranial (or superior) vertebral body on the first side and/or the second side by accidentally pressing, squeezing or compressing the handle of the alignment guide relative to the powered handpiece. The squeezing or compressing action will cause the short keel rasp to lift superiorly toward the cranial resected or prepared surface and prematurely create channels if the powered handpiece is activated. The short keel feature of the short keel rasp should be spaced apart from the first and/or second cranial resected surface of the cranial (or superior) vertebral body. The spacing may include a distance of at least 1 mm. The surgeon should continue to translate the alignment guide and the short keel rasp anteriorly within the first and/or second caudal keel channels until the alignment guide stops translating. The surgeon should confirm placement, alignment and/or positioning of the tools by acquiring at least one image with at least one imaging technique on a first side and a second side.

In another embodiment, the surgeon may complete the step of preparing and/or creating a first cranial keel channel on a least a portion of the first cranial resected or prepared surface on the cranial vertebral body by squeezing or compressing the handle of the alignment guide relative to the powered handpiece to lift the short keel rasp superiorly towards the first cranial resected or prepared surface until it contacts the first cranial resected or prepared surface on the first side. The surgeon may initiate the reciprocation of the powered handpiece to create at least a portion of the first cranial keel channel on the first side (e.g., stamping or inscribing). The surgeon may desirably remove the alignment guide from the powered handpiece to complete the remaining portion of the first cranial keel channel on the first side. Alternatively, the surgeon may initiate the reciprocation of the powered handpiece to create the entirety of the first cranial keel channel on the first side.

Subsequently, the surgeon may complete the step of preparing and/or creating a second cranial keel channel on a least a portion of the second cranial resected or prepared surface on the cranial vertebral body by squeezing or compressing the handle of the alignment guide relative to the powered handpiece to lift the short keel rasp superiorly towards the second cranial resected or prepared surface until it contacts the second cranial resected or prepared surface on the second side. The surgeon may initiate the reciprocation of the powered handpiece to create at least a portion of the second cranial keel channel on the second side (e.g., stamping or inscribing). The surgeon may desirably remove the alignment guide from the powered handpiece to complete the remaining portion of the second cranial keel channel on the second side. Alternatively, the surgeon may initiate the reciprocation of the powered handpiece to create the entirety of the second cranial keel channel on the second side.

With reference to FIG. 25D, the surgeon may slide or translate the powered handpiece with rasp assembly and/or alignment guide posteriorly within the first and/or side. The first and/or second cranial keel channel on the cranial vertebral body extends from the cranial resected surface towards the superior direction. The first cranial keel channel comprises a first cranial keel channel depth, a width and a length. The second cranial keel channel comprises a second cranial keel channel depth, a width and a length. The first and/or second cranial keel channel depth, width and length matches or substantially matches a portion of the first and/or second spinal implant keel length, width and/or depth. The first and/or second cranial keel channel width matches or substantially matches the widest portion of the first and/or second spinal implant keel width. Once the first and/or second cranial keel channel have been created, the surgeon may remove the alignment guide and/or the keel rasp from the prepared intervertebral space on the first and/or second side.

In another embodiment, the step of completing at least one cranial keel channel, a first cranial keel channel and/or a second cranial keel channel, the surgeon may complete the step of confirming placement, alignment and/or positioning of each of cranial and caudal keel channels. In one embodiment, the step of confirming placement, alignment and/or position includes verifying the different axis of each of the first cranial keel relative to the first caudal keel channel on the first side and the different axis of each of the second cranial keel channel relative to the second caudal keel channel on the second side by acquiring at least one image with at least one imaging technique. The different axis may include longitudinal axis, a vertical axis and/or transverse axis.

Figure 25E:
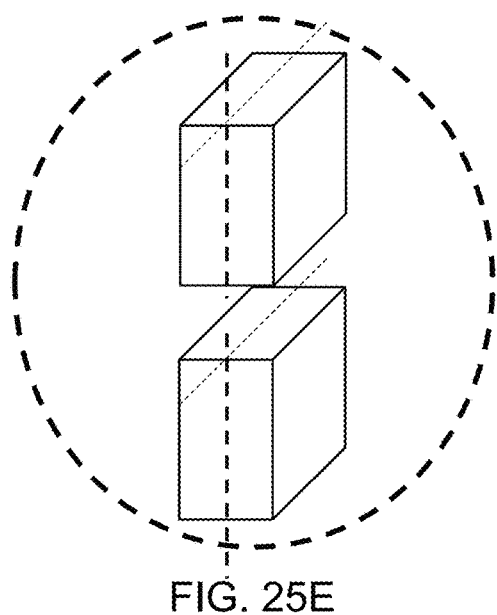
FIG. 25E depicts a magnified view of one embodiment of an aligned caudal keel channel relative to a cranial keel channel.

In another embodiment, the first side includes a first caudal keel channel and a first cranial keel channel as shown in FIGS. 25D-25E. The first caudal keel channel comprises a first caudal longitudinal axis and the first cranial keel channel comprises a cranial longitudinal axis. The first cranial longitudinal axis and the first caudal longitudinal axis are parallel and/or substantially parallel. In another embodiment, the first caudal keel channel comprises a first caudal vertical axis and the first cranial keel channel comprises a first cranial vertical axis. The first cranial vertical axis and the first caudal vertical axis are co-axial and/or substantially co-axial. In another embodiment, the first cranial longitudinal axis and the first caudal longitudinal axis are parallel and/or substantially parallel and the first cranial vertical axis and the first caudal vertical axis are co-axial and/or substantially co-axial.

In another embodiment, the second side includes a second caudal keel channel and a second cranial keel channel. The second caudal keel channel comprises a second caudal longitudinal axis and the second cranial keel channel comprises a cranial longitudinal axis. The second cranial longitudinal axis and the second caudal longitudinal axis are parallel and/or substantially parallel. In another embodiment, the second caudal keel channel comprises a second caudal vertical axis and the second cranial keel channel comprises a second cranial vertical axis. The second cranial vertical axis and the second caudal vertical axis are co-axial and/or substantially co-axial. In another embodiment, the second cranial longitudinal axis and the second caudal longitudinal axis are parallel and/or substantially parallel and the second vertical axis and the second caudal vertical axis are co-axial and/or substantially co-axial.

Surgical Deployment Technique—Implanting a Spinal Implant

Figure 26A:
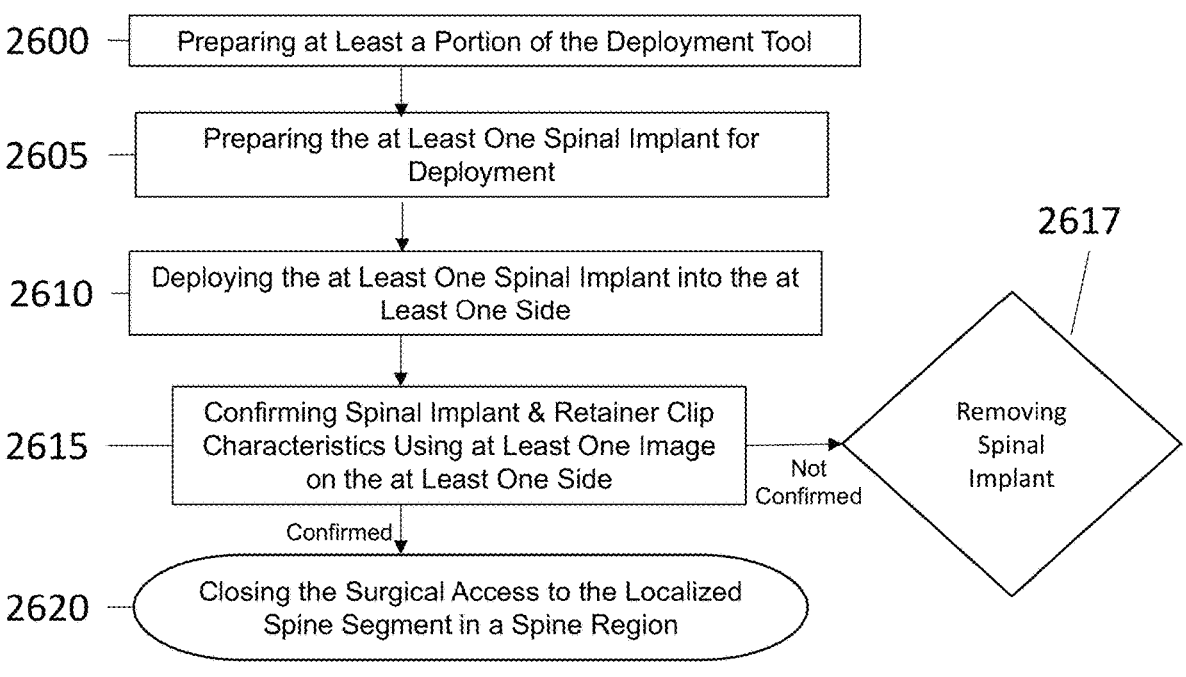

With reference to FIG. 26A, an exemplary intraoperative procedure may comprise the step of implanting a spinal implant within the prepared intervertebral space on the at least one side. The step of implanting a spinal implant on the at least one side can comprise the steps of: preparing at least a portion of the deployment tool 2600; preparing the at least one spinal implant for deployment 2605; deploying the at least one spinal implant to the prepared intravertebral space on the at least one side 2610; confirming the at least one spinal implant characteristics using at least one image with at least one imaging technique 2615. If the at least one spinal implant characteristic fails confirmation, the surgeon may complete the step of removing the at least one spinal implant.

With reference to FIG. 26B, the intraoperative procedure may comprise the step of implanting a first and second spinal implant within the prepared intervertebral space in a first and second side. The step of implanting a first and second spinal implant on the first and second sides comprises the steps of: preparing at least a portion of one or more deployment tools 2625; preparing a first and second spinal implant for deployment 2630; deploying the first spinal implant to the first prepared intravertebral space in the first side and the second spinal implant into the second intravertebral space in the second side 2635; confirming the first and second spinal implant characteristics using at least one image with at least one imaging technique on a first side and a second side 2640. If the first and/or second spinal implant characteristics fail confirmation, the surgeon may complete the step of removing the first and/or second spinal implant 2642.

With reference to FIG. 26C, the intraoperative procedure may comprise the step of implanting a first spinal implant within the first prepared intervertebral space on a first side. The step of implanting a first spinal implant on the first side comprises the steps of: preparing at least a portion of a first deployment tool 2650; preparing the first spinal implant for deployment 2655; deploying the first spinal implant into the first prepared intravertebral space on the first side 2660; confirming the first spinal implant characteristics using at least one image with at least one imaging technique on the first side 2665. If the first spinal implant characteristic fails confirmation, the surgeon may complete the step of removing the first spinal implant. If the first spinal implant characteristics confirmation is successful, the surgeon should proceed with the steps of preparing the intervertebral space within a localized spinal segment for alignment and motion restoration for a second side. The remaining steps include preparing an intervertebral space within a localized spinal segment for alignment and motion restoration for a second side; and implanting a second spinal implant on a second side.

The first spinal implant may comprise the same selected size as the second spinal implant. The first spinal implant may comprise a different selected size as the second spinal implant. The first prepared intervertebral space may comprise the same vertebral localized segment as the second prepared intervertebral space. The first intervertebral space may comprise a different localized segment as the second prepared intervertebral space. The at least one spinal implant, the first spinal implant and/or a second spinal implant characteristics may comprise confirmation of aligned cranial and caudal keel channels, the angle of convergence or transverse pedicle angle, the implant positioning, the proper intervertebral space preparation, the proper implant sizing, and/or any combination thereof.

Figures 27A, 27B, 27C:
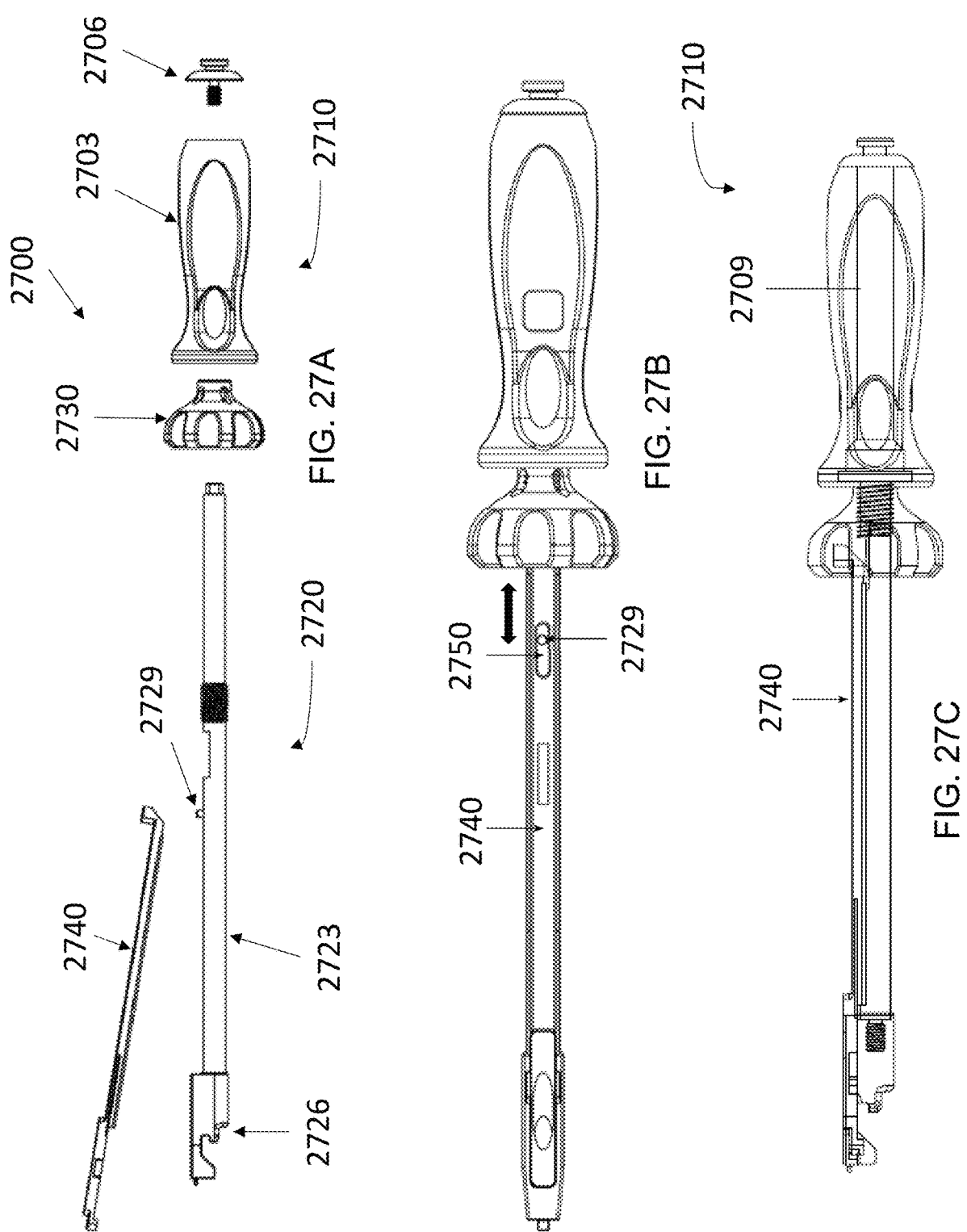
FIGS. 27A-27C depicts different views of one embodiment of a deployment tool.

In one embodiment, a step of preparing at least a portion of the deployment tool, at least a portion of a first deployment tool, and/or at least a portion of a second deployment tool comprises the steps of; acquiring a portion of the deployment tool parts; and assembling at least a portion of the deployment tool. The step of acquiring a portion of the deployment tool parts includes the variety of different parts that create the deployment tool assembly. With reference to FIGS. 27A-27C, the deployment tool assembly 2700 can comprise a deployment handle subassembly 2710; a shaft subassembly 2720; a locking knob 2730; and a draw bar 2740. The deployment handle subassembly 2710 can comprises a handle 2703, an end cap 2706 and a handle core 2709. The shaft subassembly 2720 can comprise a shaft 2723, a grasping tip 2726, and a dowel pin 2729.

The surgeon may dispose the draw bar onto the shaft subassembly. The draw bar comprises a first end, a second end and an opening. The shaft subassembly comprises a first end and a second end. The first end of the shaft subassembly comprises a grasping tip, the grasping tip includes a hook. The surgeon may align an opening 2750 on the draw bar to the dowel pin that extends from the shaft subassembly. The first end of the draw bar may flush or below the first end of the shaft subassembly. The locking knob may be secured onto the shaft subassembly and the draw bar by turning clockwise. The surgeon may desire that the second end of the draw bar may be disposed within the locking knob to secure the draw bar and prevent premature or unwarranted translation. The locking knob that is secured over the draw bar and the shaft subassembly should be coupled and/or secured to the handle subassembly.

In one embodiment, the step of preparing the at least one spinal implant for deployment comprises the steps of: selecting at least one pre-determined spinal implant; and assembling the at least one spinal implant; and securing the at least one spinal implant to the deployment tool. The step of selecting at least one predetermined spinal implant includes a selection of the implant that was pre-determined during the step of selecting a proper spinal implant size on at least one side. As discussed herein, the surgeon will desirably engage in tissue balancing, length trialing and height trialing on at least one side of a spinal region to determine the proper size (e.g., length and height) of the spinal implant that should be deployed into the prepared intervertebral space. The surgeon may acquire the proper size from the 15 different available sizes, if desired.

With reference to FIG. 28A, the surgeon may complete the step of assembling at least one spinal implant 2800 by assembling a selected superior component 2810 and an inferior component 2820 of the least one spinal implant 2800. In one disclosed embodiment, the at least one spinal implant may comprise a superior component 2810, an inferior component 2820, and a fixation screw (not shown). The at least one spinal implant may further comprise a retainer ring or retainer clip 2830. The superior component 2810 can comprise a superior articulation component 2840 which may comprise a socket surface having a concave shape. The inferior component comprises an inferior articulation component 2850 and a bridge 2860. The inferior articulation component may comprise a ball surface comprising a convex or hemi-spherical shape. The socket surface of the superior component desirably contacts and engages the ball surface of the inferior component to create a polyaxial articulation joint. The polyaxial articulation joint is desirably movable in a plurality of different orientations, which can including various combinations of flexion, extension, rotation, lateral flexion; contralateral flexion; and/or any combination thereof. The fixation screw is disposed through the posterior end of the bridge to be secured to inferior or caudal vertebral body. The fixation screw is disposed at an angle. The angle may match or substantially match the sagittal pedicle angle.

The superior component further comprises a superior base 2860 and a superior keel 2865. The superior articulation component is disposed onto the superior base and/or the superior articulation component is coupled to the superior base. The superior base comprises a first material and the superior articulation component can optionally comprise a second material. The first material may comprise the same material as the second material. The first material may comprise a different material than the second material. The materials may comprise a polymer, a metal and/or a ceramic. The polymer may comprise thermoplastics or thermosets. The polymer may further comprise cross-linked polymers. The polymer may comprise polyethylene (PE), high density polyethylene (HDPE), ultra-high molecular weight polyethylene (UHMWPE), and/or any combination thereof. The polymers may further comprise being cross-linked one or more times. The polymers may further comprise antioxidant doped or impregnated polymers. The antioxidants may include Vitamin E or Vitamin C. The metals may comprise stainless steel, titanium, titanium alloys, cobalt chrome, cobalt chrome alloys, and/or any combination thereof.

The inferior component 2820 further comprises an inferior base 2870 and an inferior keel 2875. The inferior articulation component is disposed onto the inferior base and/or the inferior articulation component is coupled to the inferior base. The bridge 2860 is coupled to the posterior end of the inferior base and extends posteriorly or extends in the posterior direction. The inferior base comprises a third material. Each of the first material, second material and/or third material may comprise the same material. Each of the first material, second material and/or the third material may comprise a different material. The materials may comprise a polymer, a metal and/or a ceramic. The polymer may comprise thermoplastics or thermosets. The polymer may further comprise cross-linked polymers. The polymer may comprise polyethylene (PE), high density polyethylene (HDPE), ultra-high molecular weight polyethylene (UHMWPE), and/or any combination thereof. The polymers may further comprise being cross-linked one or more times. The polymers may further comprise antioxidant doped or impregnated polymers. The antioxidants may include Vitamin E or Vitamin C. The metals may comprise stainless steel, titanium, titanium alloys, cobalt chrome, cobalt chrome alloys, and/or any combination thereof.

At least a portion of the bridge, the inferior base and/or the superior base may comprise a coating. Alternatively, the entirety of the bridge, inferior base and/or superior base may comprise a coating. The coatings may include inorganic coatings or organic coatings. The coatings may further include a metal coating, a polymer coating, a composite coating (ceramic-ceramic, polymer-ceramic, metal-ceramic, metal-metal, polymer-metal, etc.), a ceramic coating, an anti-microbial coating, a growth factor coating, a protein coating, a peptide coating, an anti-coagulant coating, an antioxidant coating and/or any combination thereof. The antioxidant coatings may comprise naturally occurring or synthetic compounds. The natural occurring compounds comprises Vitamin E and Vitamin C (tocotrienols and tocopherols, in general), phenolic compounds and carotenoids. Synthetic antioxidant compounds include a-lipoic acid, N-acetyl cysteine, melatonin, gallic acid, captopril, taurine, catechin, and quercetin, and/or any combination thereof. The coatings can be impregnated, applied and/or deposited using a variety of coating techniques. These techniques include sintered coating, electrophoretic coating, electrochemical, plasma spray, laser deposition, flame spray, biomimetic deposition and wet methods such as sol-gel-based spin-and-dip or spray-coating deposition have been used most often for coating implants.

The metal coatings may comprise titanium, titanium alloys, cobalt-chrome alloys, platinum and stainless steel, and/or any combination thereof. More specifically, the metal coating includes titanium and/or cobalt-chrome molybdenum (CoCrMo). The polymer coatings may include thermoplastic or thermoset polymers. The polymers may further include carbon fiber, polyether ether ketone (PEEK), polyethylene (PE), ultra-high molecular weight polyethylene (UHMWPE), polycarbonate (PC), polypropylene (PP) and/or any combination thereof. The ceramic coatings may include alumina ceramics, Zirconia (ZrO2) ceramics, Calcium phosphate or hydroxyapatite (Ca10(PO46(OH)2) ceramics, titanium dioxide (TiO2), silica (SiO2), Zinc Oxide (ZnO) and/or any combination thereof.

Figures 29C, 29D, 29E:
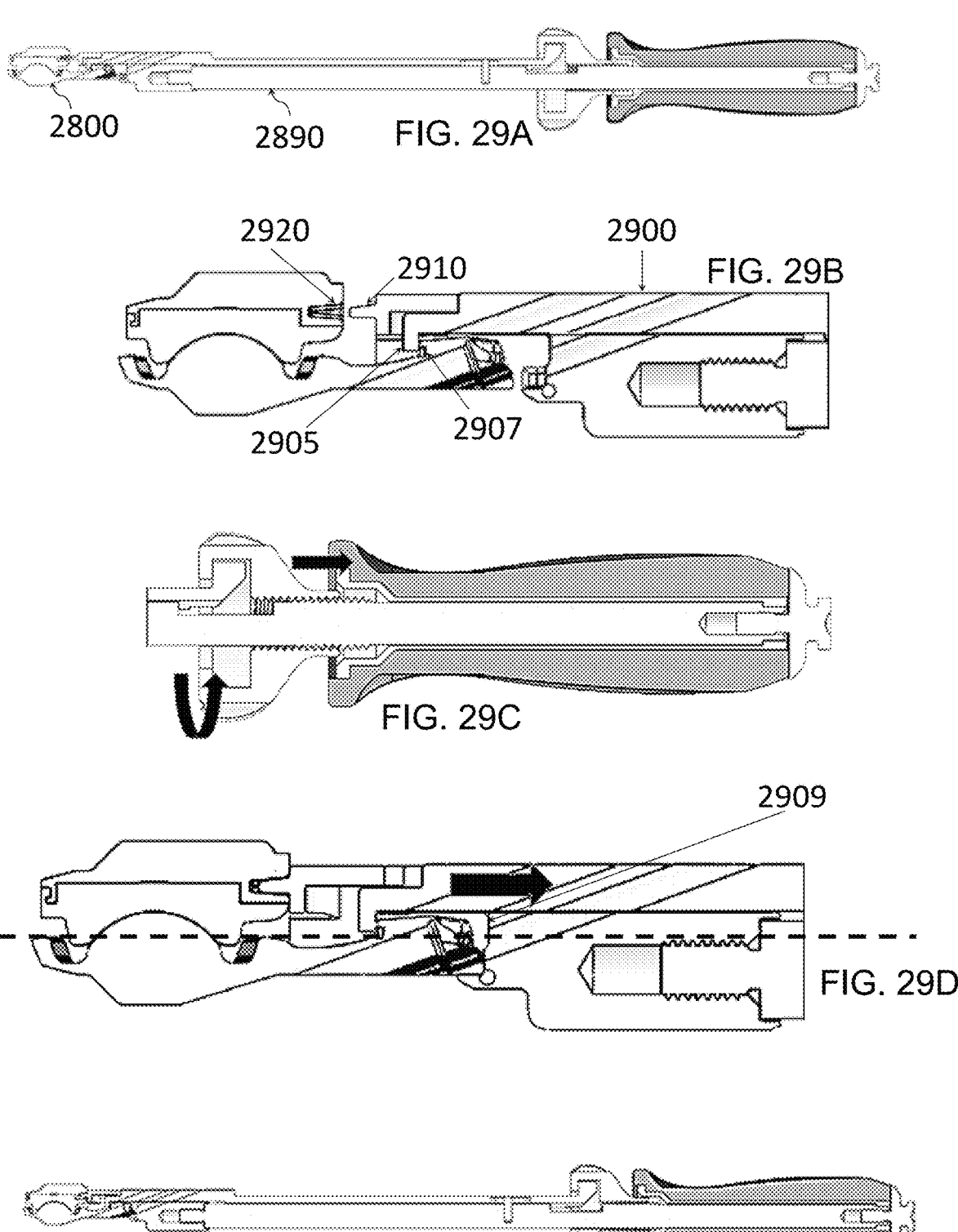

With reference to FIGS. 28B-28D and FIGS. 29A-29D, the surgeon may complete the step of securing the at least one spinal implant 2800, a first spinal implant and/or a second spinal implant to one or more deployment tools 2890. The surgeon may tilt the first end of the assembled deployment tool and insert the posterior end or second end of the implant into the pocket of the grasping tip disposed on the first end of the deployment tool. The surgeon can secure the posterior end or second end of the spinal implant into the hook of the grasping tip disposed on the first end of the deployment tool. More specifically, the surgeon can insert the hook 2905 of the grasping tip to contact or engage with the retainer clip channel 2907 on the posterior end of the bridge of the spinal implant. The locking knob should be rotated (e.g., clockwise or counterclockwise—see FIG. 28D) to translate the at least one spinal implant posteriorly until at least a portion of the at least one spinal implant contacts and/or engages with the stop wall 2909 of the grasping tip and the protrusion 2910 on the draw bar 2900 is inserted into the protrusion socket 2920 or recess, as best seen in FIG. 29B. The protrusion socket or recess is sized and configured to receive at least a portion of the protrusion of the locking arm. The surgeon will desirably experience some force feedback on the locking knob to indicate that contact has been made against the stop wall of the grasping tip. The at least one spinal implant should be in a neutral position and/or aligned with the longitudinal axis of the deployment tool. The at least one spinal implant should be in a neutral position and/or parallel with the longitudinal axis of the deployment tool.

With reference to FIGS. 30A-30E, the surgeon may complete the steps of deploying the at least one spinal implant into the at least one side. The step of deploying the at least one spinal implant into the at least one side comprises the steps of: aligning the each of the superior and/or inferior keels on the spinal implant to each of the caudal and/or cranial keel channels on at least one side; securing fixation screw into the caudal or inferior vertebral body into the at least one side; and releasing or disengaging the deployment tool on the at least one side.

Figures 30A, 30B, 30C, 30D, 30E, 30F:
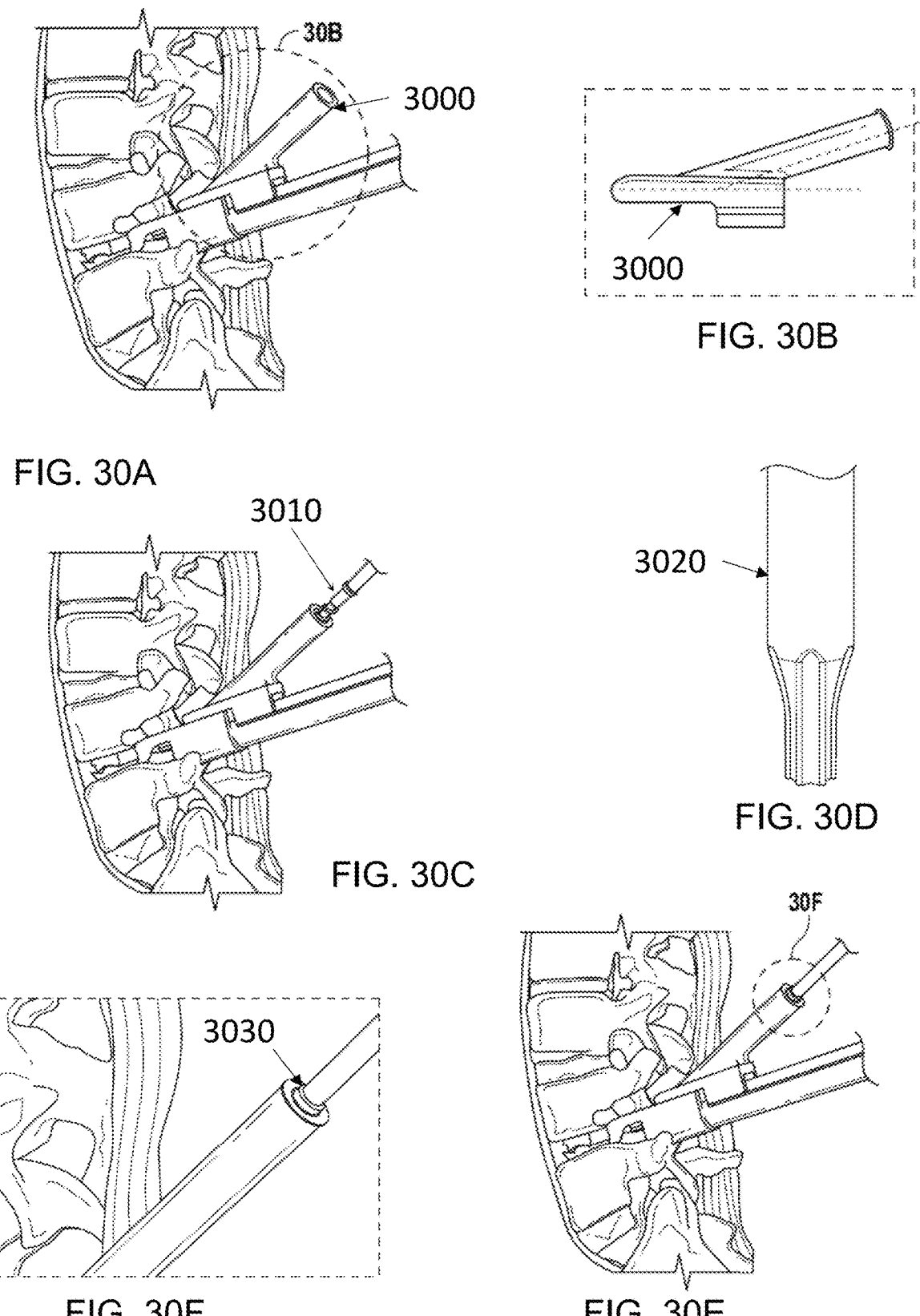
FIGS. 30A-30E depicts different sagittal and exploded views of a method of deploying a spinal implant within the prepared intravertebral space.

With reference to FIG. 30A, the surgeon may complete the step of aligning each of the superior and/or inferior keels on the spinal implant to each of the caudal and/or cranial keel channels on at least one side, a first side and/or a second side. The surgeon should align the superior keel of the at least one spinal implant with the cranial keel channel and the inferior keel of the at least one spinal implant with the caudal keel. The surgeon can then translate and/or push the deployment tool forward until the superior keel and/or the inferior keel of the at least one spinal implant contacts and/or engages with at least one anterior end or anterior surface of the caudal and/or cranial keel channels. The pushing force should be a minimal force. The surgeon should be aware to not over distract prepared intravertebral disc space that what was originally pre-determined during the step of selecting a proper spinal implant size.

With reference to 30B-30F, the surgeon may complete the step of securing the fixation screw to the caudal or inferior vertebral body. The surgeon may desirably attach a screw guide 3000 near and/or proximate to medial and/or lateral rails at the first end of the deployment tool (FIGS. 30A and 30B). The screw guide will be positioned and/or disposed onto a portion of the grasping tip and/or a portion to the shaft subassembly and secured. Alternatively, the screw guide may be attached prior to the step of aligning each of the superior and/or inferior keels to each of the caudal and/or cranial keel channels. The guide barrel or the guide tube of the screw guide can be positioned obliquely and/or at an angle relative the longitudinal axis of the body of the screw guide. Accordingly, the longitudinal axis of the guide barrel or the guide tube is at an angle relative to the longitudinal axis of the body of the screw guide. The surgeon may desirably insert the fixation screw 3010 into the bore (e.g., inner diameter) of the guide barrel or guide tube of the screw guide. A deployment screwdriver 3020 may be utilized to secure the fixation screw into the caudal vertebral body. The deployment screwdriver may be powered and/or manual. The deployment screwdriver is desirably coupled to a quick-connect handle (e.g., a Hudson handle) for manual installation. The surgeon will insert the drive tip or tip into a portion of the drive recess of the fixation screw. The surgeon may begin to rotate the deployment screwdriver clockwise to perforate the cortex using the fixation screw tip until the surgeon receives feedback and/or torque feedback (e.g., tightening). The surgeon should not over-rotate, over-tighten or over-torque the fixation screw into the vertebral body—it may cause changes to positioning, alignment, and/or prepared bone interface.

With reference to FIG. 30E, the surgeon may complete the step of disengaging, disconnecting and/or releasing the at least on spinal implant deployed into the at least one side. Once the fixation screw is secured into the caudal vertebral body, the deployment screwdriver may be removed. The surgeon may slightly release the deployment tool securing force from the at least one spinal implant by turning and/or rotating the locking knob (e.g., counterclockwise or clockwise) of the deployment tool. The deployment screwdriver should be rotated (e.g., counterclockwise or clockwise) until the reference line 3030 on the deployment screwdriver is visible above a top surface of the guide barrel and/or the guide tube. Disconnect and/or disengage the deployment tool from the at least one spinal implant and remove from the prepared intravertebral space.

Figure 31A:
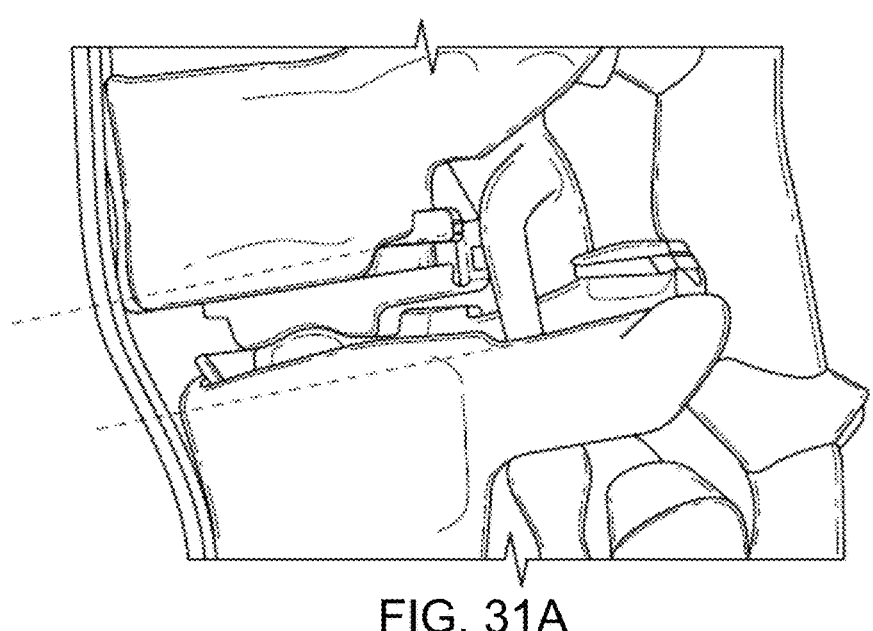
FIGS. 31A-31F depicts different views of one or more characteristics required for confirmation of a deployed spinal implant into the prepared intervertebral space.
Figure 31B:
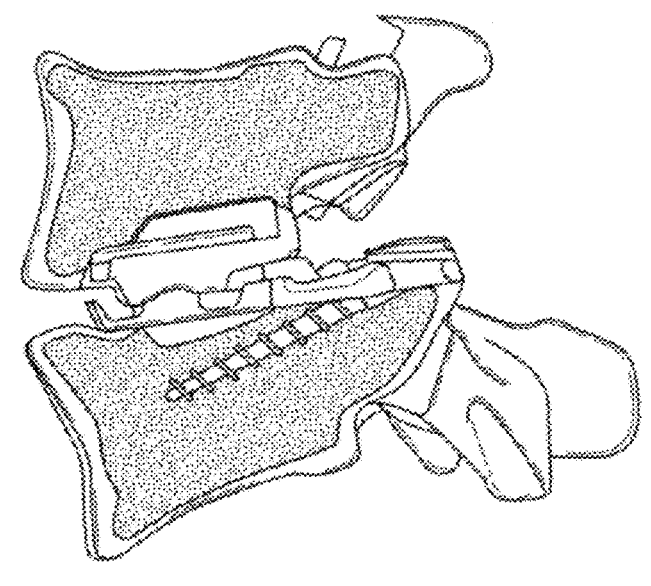
Figure 31C:
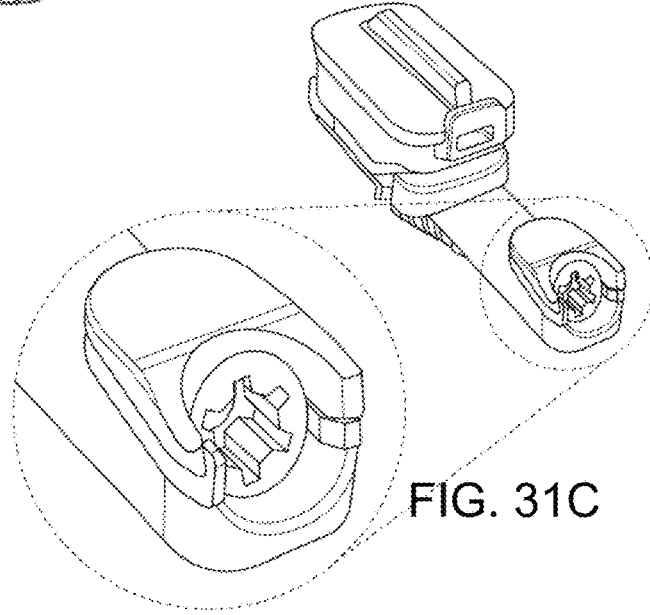
Figure 31D:
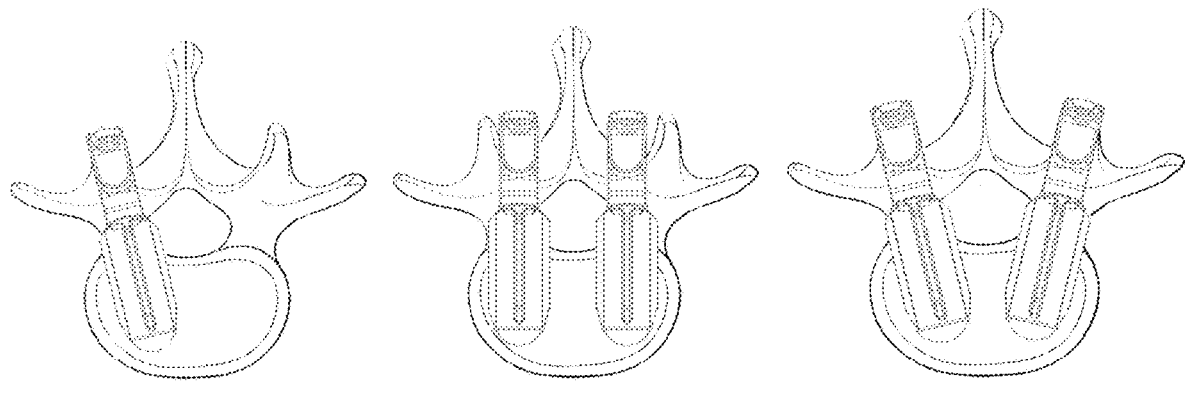
Figure 31E:
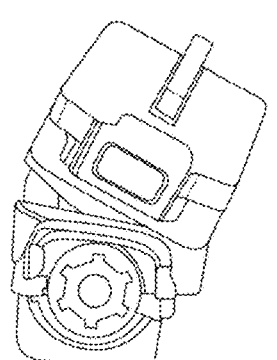
Figure 31F:
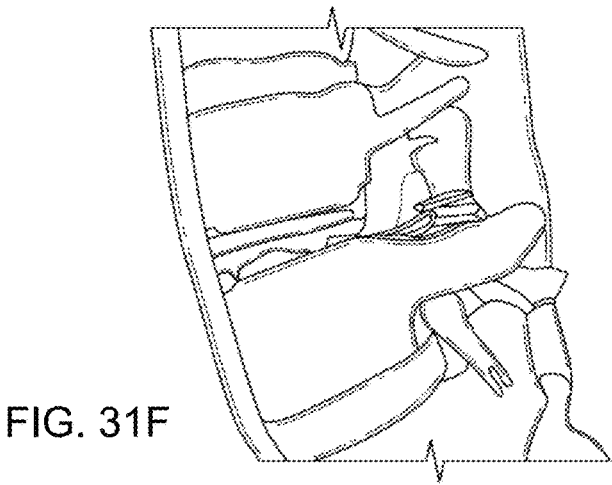

With reference to FIGS. 31A-31C, a surgeon can confirm placement, alignment and/or positioning of the at least one spinal implant (e.g., a first spinal implant and/or a second spinal implant) using at least one image with at least one imaging technique on at least one side, the first side, and/or the second side, to confirm the placement, alignment and/or positioning of the at least one spinal implant within the intervertebral space. The surgeon may verify a plurality of characteristics and/or one or more characteristics, including those shown in FIGS. 31A-31F. The plurality of characteristics may include a desired toe-in angle or convergence angle or transverse pedicle angle for one or both implant pairs and/or the various components thereof, the tensioning of the soft tissues (e.g., desirably ensuring to not over tensioning—see FIG. 31F), the positioning of the retainer clip(s); positioning of the spinal implant components relative to the prepared intervertebral space; alignment of the superior and/or inferior keels relative to the caudal and/or cranial keel channels (See FIG. 31E); alignment of the prepared or resected inferior surface(s) of the cranial or superior vertebral body with relative to the resected superior surface of the caudal or inferior vertebral body. The alignment may comprise ensuring that the alignment is parallel and/or substantially parallel (See FIG. 31A). In another embodiment, the surgeon may verify the cranial or superior vertebral body comprises a parallel or substantially parallel alignment relative to the caudal or inferior vertebral body. In another embodiment, the surgeon may verify the at least one resected surface of the cranial or superior vertebral body comprises a parallel or substantially parallel alignment relative to at least one resected surface of the caudal or inferior vertebral body. Substantially may comprise within ten percent of parallel alignment and/or measurement.

Spinal Implants to Promote Fusion

While much of the present disclosure describes various methods and steps to accomplish restoration of motion to a treated spinal segment or portion thereof, it should be understood that various features of the present disclosure would have equal utility for the planning, treatment and placement of devices to promote arthrodesis and/or fusion of various regions of the patient's spine. In such instances, the restoration of spinal alignment at various spinal levels may significantly reduce undesirable loading of the implanted fusion implant components, which can significantly improve patient comfort and/or surgical outcomes, including improving the durability of the implanted components. Accordingly, the disclosed methods are relevant to the implantation of spinal fusion devices such as those disclosed in co-pending U.S. Provisional Application No. 63/445,954 entitled "Fusion Spinal Implant Systems," filed Feb. 15, 2023, which disclosure is incorporated by reference herein in its entirety.

Surgical Removal Technique

Figure 32:
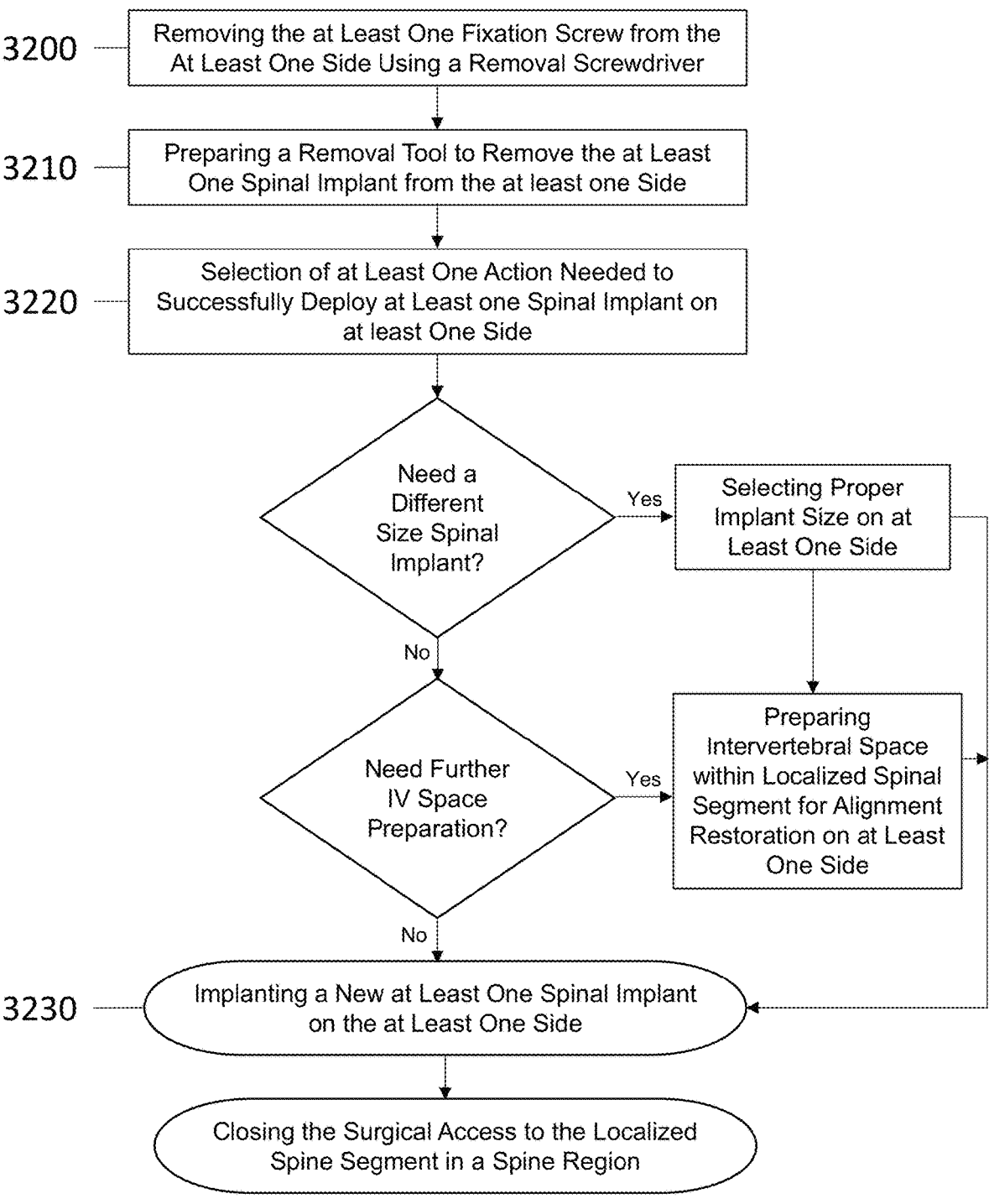
FIG. 32 graphically illustrates one embodiment of a method of removing at least one spinal implant from the prepared intervertebral space.

With reference to FIG. 32, the preoperative procedure may comprise the step of removing at least spinal implant from the at least one side. The step of removing at least one spinal implant may be necessary if the tensioning, alignment, positioning, and/or placement of the at least one spinal implant deployed within the prepared intervertebral space within a spine region is unable to be confirmed as meeting surgeon and implant requirements, or where implant removal is desired for any reason. The step of removing at least one spinal implant from the at least one side comprises the steps of: removing the at least one fixation screw from the at least one spinal implant on the at least one side 3200;

removing the at least one spinal implant from the at least one side 3210; selecting at least one action needed to successfully deploy at least one spinal implant on the at least one side 3220; and implanting a new or subsequent at least one spinal implant on the at least one side 3230.

With reference to FIG. 33A-33B, the surgeon may complete the step of removing the at least one fixation screw from the at least one spinal implant on the at least one side. A removal screwdriver 3300 may be utilized to disengage and remove the fixation screw from the caudal vertebral body. The removal screwdriver may be powered and/or manual. The removal screwdriver can be coupled to a handle (e.g., Hudson handle) for manual operation. The surgeon will desirably insert the drive tip or tip into a portion of the drive recess of the fixation screw. The edge, rim and/or shoulder of the removal screwdriver can desirably force the retainer clip to be movable from the fixed position or closed position, which a portion of the retainer clip contacts or engages a surface on the fixation screw to prevent premature backing out, to a unfixed position or an open position, the at least a portion of retainer clip expanding to allow the removal driver to disengage the fixation screw from the portion of the retainer clip. The surgeon may begin to rotate counterclockwise the deployment screwdriver until the surgeon receives feedback and/or torque feedback (e.g., loosening) and continue rotating until the fixation screw is removed from the at least one spinal implant (See FIG. 33B).

With reference to FIG. 34A-34C, the surgeon may complete the step of removing the at least one spinal implant from the at least one side. The step of removing the at least one spinal implant from the at least one side may comprise the step of assembling a removal tool 3400. The removal tool will desirably include a capture end of hook 3410 at a bent distal tip 3420, which hook 3410 may be utilized to grasp a portion of the at least one spinal implant and remove the at least one spinal implant from the prepared intervertebral space within a spine region (See FIGS. 34B and 34C). The removal tool may be powered and/or manual. The removal tool can be coupled to a handle (e.g., Hudson handle) for manual installation. The removal tool comprises a first end and a second end. The second end may include the handle or quick connect engagement feature. The first end includes a hook.

With reference to FIGS. 33B, the surgeon may complete the step of removing the at least one spinal implant from the at least one side may comprise the step of removing the at least one spinal implant from the at least one side. The surgeon may insert the first end of the removal tool into the prepared intervertebral space. The surgeon should locate the fixation screw bore disposed on the bridge of the inferior component of the at least one spinal implant. The hook disposed in the first end of the removal hook grasps is inserted into the screw bore of the bridge of the inferior component of the spinal implant. The removal tool should translate posteriorly until at least a portion of the hook on the first end of the removal tool contacts or engages with a portion of an inner diameter of the screw bore. Once the removal tool is secured, the surgeon may begin translating or pulling the at least one spinal implant on the at least one side to remove the superior and inferior components of the at least one spinal implant. After the at least one spinal implant is retracted from the prepared interverbal space, the at least one spinal implant may be discarded. Ensure both pieces, superior and/or inferior components, of the spinal implant were removed.

In another embodiment, the surgeon may complete the step of selecting at least one action needed to successfully deploy at least one spinal implant on the at least one side. The selecting of one action may comprise re-selecting a different sized spinal implant or re-preparing the Intervertebral space within a localized spine segment for alignment restoration on at least one side. The action of re-selecting of a different sized spinal implant may be necessary if excessive friction during or excessive tension was noted during deployment of the at least one spinal implant. The surgeon should repeat one or more steps disclosed herein, described as implanting at least a spinal implant on the at least one side. For example, if too much tension and/or too much friction was observed, it may be necessary to decrease the height of the implant.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein. What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

The invention claimed is:

1. A method of restoring spinal alignment and range of motion comprises the steps of:

completing a preoperative imaging protocol to acquire at least one image using one technique to create a first one or more preoperative measurements on a first side and a second one or more preoperative measurements on a second side;

selecting a surgical approach;

positioning the patient properly;

completing an operative imaging protocol to acquire at least one image using one technique to create a first one or more operative measurements on a first side, a second one or more operative measurements on a second side and confirming the first one or more operative measurements on a first side relative to the first one or more preoperative measurements and the second one or more operative measurements on a second side relative to the second one or more preoperative measurements on a second side;
accessing at least one localized spine segment in a spine region;
selecting a spinal implant size on a first side;
preparing a caudal vertebral body on the first side;
preparing a cranial vertebral body on the first side;
completing a first caudal keel channel on the caudal vertebral body on the first side; and
completing a first cranial keel channel on the cranial vertebral body to substantially align with a first toe-in angle of a pedicle of the cranial vertebral body;
implanting the selected spinal implant into the first side;
selecting a spinal implant size on a second side;
preparing an intervertebral space within the at least one localized spine segment in the spine region on the second side; and
implanting the selected spinal implant into the second side.

2. The method of claim 1, wherein the step of preparing the cranial vertebral body on the first side comprises the step of preparing a portion of an endplate on the first side of the cranial vertebral body to create a first cranial resected or cranial prepared surface.

3. The method of claim 1, wherein the step of preparing the cranial vertebral body on the first side further comprises the step of confirming a first alignment of the first cranial resected or prepared surface relative to the first caudal resected surface on the first side.

4. The method of claim 3, wherein the confirming the first alignment comprises confirming parallel or substantially parallel alignment of the first cranial prepared or resected surface relative to the first caudal resected surface.

5. The method of claim 1 wherein the step of completing a first caudal keel channel on the caudal vertebral body on the first side comprises the step of creating the first caudal keel channel extending below the first caudal resected surface on the first side, the first caudal keel channel including a first caudal vertical axis.

6. The method of claim 1, wherein the step of completing a first cranial keel channel on the cranial vertebral body on the first side comprises the step of creating the first cranial keel channel above the first cranial resected or prepared surface of the cranial vertebral body that aligns with the first caudal keel channel, the first cranial keel channel including a first cranial keel channel vertical axis.

7. The method of claim 1, wherein the preoperative imaging protocol comprises one or more static and dynamic patient positions.

8. The method of claim 1, wherein the first one or more preoperative measurements comprises a first angle of correction and/or first center of rotation and the second one or more preoperative measurements comprises a second angle of correction and a second center of rotation.

9. The method of claim 8, wherein the first angle of correction comprises a first sagittal angle and/or a first coronal angle and the second angle of correction comprises a second sagittal angle and/or a second coronal angle.

10. The method of claim 9, wherein the first angle of correction comprises a different angle than the second angle of correction.

11. A method of restoring spinal alignment and range of motion comprises the steps of:
completing a preoperative imaging protocol to acquire at least one image using one technique to create a first one or more preoperative measurements on a first side and a second one or more preoperative measurements on a second side;
selecting a surgical approach;
positioning the patient properly;
completing an operative imaging protocol to acquire at least one image using one technique to create a first one or more operative measurements on a first side, a second one or more operative measurements on a second side and confirming the first one or more operative measurements on a first side relative to the first one or more preoperative measurements and the second one or more operative measurements on a second side relative to the second one or more preoperative measurements on a second side;
accessing at least one localized spine segment in a spine region;
selecting a spinal implant size on a first side;
preparing an intervertebral space within the at least one localized spine segment in the spine region on the first side;
implanting the selected spinal implant into the first side;
selecting a spinal implant size on a second side;
preparing a caudal vertebral body on the second side;
preparing a cranial vertebral body on the second side;
completing a caudal keel channel on the caudal vertebral body on the second side;
completing a cranial keel channel on the cranial vertebral body to substantially align with a second toe-in angle of a second pedicle of the cranial vertebral body; and
implanting the selected spinal implant into the second side.

12. The method of claim 11, wherein the step of preparing the intervertebral space within the at least one localized spine segment in the spine region on the first side comprises the step of preparing a portion of an endplate and a portion of a pedicle on the first side of the caudal vertebral body to create a first caudal resected surface.

13. The method of claim 12, wherein the first caudal resected surface comprises a first sagittal angle, the first sagittal angle matches or substantially matches a first angle of correction obtained from the first one or more preoperative measurements.

14. The method of claim 11, wherein the step of preparing the caudal vertebral body on the second side comprises the step of preparing a portion of an endplate and a portion of a pedicle on the second side of the caudal vertebral body to create a second caudal resected surface.

15. The method of claim 14, wherein the second caudal resected surface comprises a second sagittal angle, the second sagittal angle matches or substantially matches a second angle of correction obtained from the second one or more preoperative measurements.

16. The method of claim 11, wherein the step of preparing the cranial vertebral body on the second side comprises the step of preparing a portion of an endplate on the second side of the cranial vertebral body to create a second cranial resected or cranial prepared surface.

17. The method of claim 11, wherein the step of preparing the cranial vertebral body on the second side further comprises the step of confirming a second alignment of the second cranial resected or prepared surface relative to the second caudal resected surface on the second side.

18. The method of claim 17, wherein the confirming the second alignment comprises confirming parallel or substantially parallel alignment of the second cranial prepared or resected surface relative to the second caudal resected surface.

19. The method of claim 11, wherein the step of completing a second caudal keel channel on the caudal vertebral body on the second side comprises the step of creating the second caudal keel channel extending below the second caudal resected surface on the second side, the second caudal keel channel including a second caudal vertical axis.

20. The method of claim 11, wherein the step of completing a second cranial keel channel on the cranial vertebral body on the second side comprises the step of creating a second cranial keel channel above the second cranial resected or prepared surface of the cranial vertebral body that aligns with the second caudal keel channel, the second cranial keel channel including a second cranial keel channel vertical axis.

* * * * *